(12) United States Patent
Otsubo et al.

(10) Patent No.: US 9,045,464 B2
(45) Date of Patent: Jun. 2, 2015

(54) QUINOLONE COMPOUND AND PHARMACEUTICAL COMPOSITION

(71) Applicant: OTSUKA PHARMACEUTICAL CO., LTD., Tokyo (JP)

(72) Inventors: Kenji Otsubo, Osaka (JP); Yuji Ochi, Osaka (JP); Masami Nakai, Osaka (JP); Atsushi Mori, Osaka (JP)

(73) Assignee: OTSUKA PHARMACEUTICAL CO., LTD., Tokyo (JP)

(*) Notice: Subject to any disclaimer, the term of this patent is extended or adjusted under 35 U.S.C. 154(b) by 0 days.

(21) Appl. No.: 14/147,115

(22) Filed: Jan. 3, 2014

(65) Prior Publication Data

US 2014/0121207 A1    May 1, 2014

Related U.S. Application Data

(63) Continuation of application No. 13/590,227, filed on Aug. 21, 2012, now Pat. No. 8,642,619, which is a continuation of application No. 12/599,003, filed as application No. PCT/JP2008/060804 on Jun. 6, 2008, now Pat. No. 8,269,011.

(30) Foreign Application Priority Data

Jun. 6, 2007  (JP) ................. 2007-150819

(51) Int. Cl.
| | |
|---|---|
| A61K 31/04 | (2006.01) |
| C07D 413/04 | (2006.01) |
| C07D 215/233 | (2006.01) |
| C07D 407/04 | (2006.01) |
| C07D 409/04 | (2006.01) |
| C07D 401/04 | (2006.01) |
| C07D 405/04 | (2006.01) |

(52) U.S. Cl.
CPC .......... *C07D 413/04* (2013.01); *C07D 215/233* (2013.01); *C07D 407/04* (2013.01); *C07D 409/04* (2013.01); *C07D 401/04* (2013.01); *C07D 405/04* (2013.01)

(58) Field of Classification Search
CPC ............................ A01N 12/006; C07D 413/04
USPC .................................... 546/153, 156; 514/312
See application file for complete search history.

(56) References Cited

U.S. PATENT DOCUMENTS

| 6,297,257 | B1 | 10/2001 | Napoletano et al. | |
|---|---|---|---|---|
| 6,645,983 | B1 | 11/2003 | Joseph et al. | |
| 8,034,546 | B2* | 10/2011 | Robinson et al. | 430/325 |
| 8,269,011 | B2* | 9/2012 | Otsubo et al. | 546/153 |
| 8,304,546 | B2 | 11/2012 | Otsubo et al. | |
| 8,642,619 | B2* | 2/2014 | Otsubo et al. | 514/312 |
| 2010/0130546 | A1 | 5/2010 | Otsubo et al. | |
| 2011/0251180 | A1 | 10/2011 | Otsubo et al. | |
| 2011/0269705 | A1 | 11/2011 | Otsubo et al. | |
| 2013/0005675 | A1 | 1/2013 | Otsubo et al. | |

FOREIGN PATENT DOCUMENTS

| EP | 0 163 888 A1 | 12/1985 |
|---|---|---|
| EP | 0 498 723 A1 | 8/1992 |
| EP | 1 886 996 A1 | 2/2008 |
| KR | 2005-0104957 A | 11/2005 |
| WO | 96/20914 A1 | 7/1996 |
| WO | 9817662 A1 | 4/1998 |
| WO | 9848790 A1 | 5/1998 |
| WO | 9932449 A2 | 7/1999 |
| WO | 0042026 A1 | 7/2000 |
| WO | 0062765 A2 | 10/2000 |
| WO | 00/68202 A1 | 11/2000 |

(Continued)

OTHER PUBLICATIONS

Gary Fiskum, et al., "Mitochondrial Mechanisms of Neural Cell Death and Neuroprotective Interventions in Parkinson's Disease", Ann. New York Academy of Sciences, 991: 111-119 (2003).

Guo Hua Jin, et al. "Synthesis of azaisoflavones and their inhibitory activities of NO production in activated microglia", Bioorganic & Medicinal Chemistry Letters, vol. 18, No. 14, Jun. 13, 2008, pp. 4092-4094.

Zhu-Ping Xiao, et al. "Synthesis, Antiproliferative Activity, and Structure-Activity Relationships of 3-Aryl-1 H-quinolin-4-ones", ChemMedChem vol. 3, No. 7, (2008), pp. 1077-1082.

(Continued)

*Primary Examiner* — D M Seaman
(74) *Attorney, Agent, or Firm* — Sughrue Mion, PLLC

(57) ABSTRACT

The present invention provides a quinolone compound represented by General Formula (1)

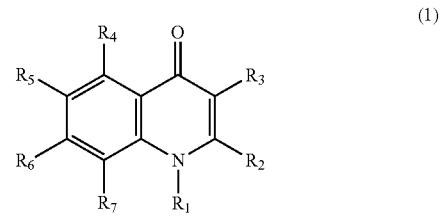

(1)

or a salt thereof, wherein $R_1$ represents a hydrogen atom, etc.; $R_2$ represents a hydrogen atom, etc.; $R_3$ represents a phenyl group optionally being substituted with one or more substituents, etc.; $R_4$ represents a halogen atom; $R_5$ represents a hydrogen atom or halogen atom; $R_6$ represents a hydrogen atom; and $R_7$ represents a hydroxyl group, etc. The quinolone compound have a functional improvement effect, which suppresses progression of neurological dysfunction by inhibiting the chronic progression of Parkinson's disease or protecting dopamine neurons from the disease etiology, thereby prolonging the period before first administration begins.

3 Claims, No Drawings

(56) References Cited

FOREIGN PATENT DOCUMENTS

| WO | 0112607 A2 | 2/2001 |
|---|---|---|
| WO | 0117986 A1 | 3/2001 |
| WO | 0222074 A2 | 3/2002 |
| WO | 0226713 A1 | 4/2002 |
| WO | 0230407 A1 | 4/2002 |
| WO | 02074307 A1 | 9/2002 |
| WO | 03035635 A1 | 1/2003 |
| WO | 2004/007461 A1 | 1/2004 |
| WO | 2004/016255 A1 | 2/2004 |
| WO | 2004/037792 A2 | 5/2004 |
| WO | 2004/087160 A1 | 10/2004 |
| WO | 2004/091485 | 10/2004 |
| WO | 2005/032559 A1 | 4/2005 |
| WO | 2005/034960 A1 | 4/2005 |
| WO | 2005/049008 A1 | 6/2005 |
| WO | 2006/045096 A2 | 4/2006 |
| WO | 2006/096780 A2 | 9/2006 |
| WO | 2008/150029 A1 | 12/2008 |
| WO | 2009/053799 A1 | 4/2009 |

OTHER PUBLICATIONS

Kazutoshi Nakano, et al. "Mitochondria and Cell Death", Journal of Clinical and Experimental Medicine, vol. 225, No. 6, May 10, 2008), pp. 501-507.
Sunitha Bollimuntha, et al. "TRPC1-mediated Inhibition of 1-Methyl-4-phenylpyridinium Ion Neurotoxicity in Human SH-SY5Y Neuroblastoma Cells", The Journal of Biological Chemistry, vol. 280, No. 3, issue of Jan. 21 (2005), pp. 2132-2140.
Tiesong Shang, et al. "Death-associated Protein Kinase as a Sensor of Mitochondrial Membrane Potential", The Journal of Biological Chemistry vol. 280, No. 41, Oct. 14, 2005, pp. 34644-34653.
Masami Nakai, et al. "1-Methyl-4-phenylpyridinum (MPP) Decreases Mitochondrial Oxidation-Reduction (REDOX) Activity and Membrane Potential in Rat Striatum", Experimental Neurology, 179, pp. 103-110 (2003).
Piu Chan, et al. "Rapid ATP Loss Caused by 1-Methyl-4-Phenyl-1,2,3,6-Tetrahydropyridine in Mouse Brain", Journal of Neurochemistry, 51, (1991), pp. 348-351.
Atsushi Mori, et al. "Neural mechanisms underlying motor dysfunction as detected by the tail suspension test in MPTP-treated C57BL/6 mice", Neuroscience Research, 51, (2005), pp. 265-274.
Jin-Inchi Koizumi, M.D., et al. "Experimental studies of ischemic brain edema 1. A new experimental model of cerebral embolism in rats in which recirculation can be introduced in the ischemic area", Japan J. Stroke 8, 1-8, (1986).
Hisashi Kitagawa, et al. "Intracerebral adenosine infusion improves neurological outcome after transient focal ischemia in rats", Neurological Research, vol. 24, Apr. 2002 pp. 317-323.
Wang Xiaoli, et al. "The study on 1H NMR of 5(7)-Chloro-6-Fluro-3-Phenyl-4-(1H)-Quinolinone Derivatives", Chinese Journal of Magnetic Resonance, vol. 15, No. 6, Dec. 1998, pp. 543-546.
Diana Alonso et al., "Marine compounds for the therapeutic treatment of neurological disorders", Expert Opinion on Therapeutic Patents 200510 GB, vol. 15, No. 10, Oct. 2005, pp. 1377-1386. (XP-002571475).
International Search Report mailed Jan. 12, 2010 corresponding to PCT/JP2009/070383.
U.S. Office Action mailed Oct. 29, 2012 in U.S. Appl. No. 13/128,803.
Patani et al, "Bioisosterism: A Rational Approach in Drug Design". Chem. Rev. Dec. 19, 1996; 96(8): 3147-3176.
International Search Report issued Mar. 30, 2012 in Application No. PCT/JP2009/070719.
U.S. Office Action mailed Jan. 31, 2012 in U.S. Appl. No. 12/599,003.
U.S. Office Action issued in U.S. Appl. No. 13/616,740 dated Dec. 18, 2012.
Final Office Action, dated Apr. 9, 2013, issued in U.S. Appl. No. 13/616,740.
Shin Kwak; "Mitochondrial Diseases (Narrow Sense) Itemized Discussion"; An English Translation of pp. 412-416 of Nippon Rinsho Extra Edition No. 4, "Mitochondria and Mitochondrial Diseases"; vol. 60 (Volume Serial No. 800); Apr. 28, 2002.
Maurice Lamant et al., "N° 280—Synthesis of 4-amino quinolines; II.—Use of 2-aryl 3-arylamino crotononitriles to prepare 2-methyl-3-aryl-4-amino quinolines and corresponding 4-hydroxy quinolones," Bulletin de la Societe Chimique de France, 1964, (7), pp. 1606-1610.
Richard B. Silverman, Northwestern University Dept. of Chemistry, "The Organic Chemistry of Drug Design and Drug Action," Elsevier Academic Press, 2004, Second Edition, Chapter 2, pp. 29-32.
Office Action dated Oct. 27, 2014 in co-pending U.S. Appl. No. 13/852,196.

* cited by examiner

QUINOLONE COMPOUND AND PHARMACEUTICAL COMPOSITION

CROSS-REFERENCE TO RELATED APPLICATIONS

This is a continuation of U.S. application Ser. No. 13/590,227, filed Aug. 21, 2012 (now U.S. Pat. No. 8,642,619), which is a continuation of U.S. application Ser. No. 12/599,003 filed Jan. 12, 2010 (now U.S. Pat. No. 8,269,011), which is a 371 National Stage Application of PCT/JP2008/060804 filed Jun. 6, 2008, which claims benefit of Japanese Application No. 2007-150819 filed Jun. 6, 2007. The above applications are incorporated herein by reference in their entirety.

TECHNICAL FIELD

The present invention relates to a quinolone compound and a pharmaceutical composition.

BACKGROUND ART

Parkinson's disease is a chronic, progressive neurodegenerative disease that generally develops after middle age. Initial symptoms include unilateral resting tremor, akinesia and rigidity. The tremors, akinesia, and rigidity are called the three major signs of Parkinson's disease, and each of them are caused by the selective death of dopaminergic neurons projected from the substantia nigra to the striatum. The etiology of the disease is still unknown; however, accumulated evidence suggests that an impaired energy-generating system accompanied by abnormal mitochondrial function of nigrostriatal dopaminergic neurons triggers the neurodegenerative disorder of the disease. The mitochondrial dysfunction has been assumed to subsequently cause oxidative stress and failure of calcium homeostasis, thereby resulting in neurodegeneration (Ann. N.Y. Acad. Sci. 991:111-119 (2003)).

Treatments of Parkinson's disease are roughly classified into medical management (medication) and surgical management (stereotaxic operation). Of these, medication is an established therapy and regarded as a basic treatment. In the medication, a symptomatic therapeutic agent is used to compensate for the nigrostriatal dopaminergic neuronal function denatured by Parkinson's disease. L-dopa exhibits the most remarkable therapeutic effects. It is said that no agent exceeds the effectiveness of L-dopa. Currently, L-dopa is used together with a dopa decarboxylase inhibitor to prevent the metabolism thereof in the periphery, and the desired clinical effects have been obtained.

However, one disadvantage of the L-dopa treatment is that after several years of usage, the decrement of the durability and stability of the drug's efficacy results in the recurrence of movement disorders such as dyskinesia and daily fluctuation. Moreover, digestive side effects such as nausea and vomiting brought on by the excess release of dopamine, circulatory organ problems such as orthostatic hypotension, tachycardia and arrhythmia, and neurological manifestations such as hallucinations, delusions and distractions have been a cause for concern.

Thus, in order to decrease the L-dopa preparation dosage and thereby reducing the side effects, multidrug therapies, in which dopamine receptor agonists, dopamine metabolism enzyme inhibitors, dopamine releaser, central anticholinergic agents and the like are used in combination, are employed. Such therapeutic advances remarkably improve prognoses; even now, however, there is no fundamental cure for Parkinson's disease and other neurodegenerative diseases. Medication must be taken for the rest of the patient's life, and the aforementioned drawbacks—decreased efficacy during long-term administration, side effects, and uncontrollable disease progression—can result from L-dopa monotherapy. In addition, it is difficult to expect dramatic effects, even during the employment of multidrug therapies.

DISCLOSURE OF THE INVENTION

The present invention aims to provide a novel compound that has a functional improvement effect and suppresses of neurological dysfunction by inhibiting the chronic progression of Parkinson's disease or protecting dopamine neurons from the disease etiology, thereby prolonging the period before first L-dopa administration begins.

The present inventors carried out extensive research to accomplish the aforementioned object, and as a result, they succeeded in producing a compound represented by the following General Formula (1), which comprises protecting and improving mitochondrial functional activity, and protecting and repairing neuron activity. The present invention has been accomplished based on the above findings.

The present invention provides a quinolone compound, a pharmaceutical composition comprising said compound, a use of said compound, a method for treating or preventing a disorder, and a process for producing said compound, as described in Item 1 to 11 below.

Item 1. A quinolone compound represented by General Formula (1)

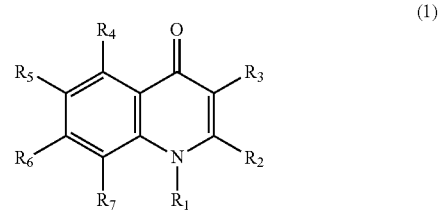

or a salt thereof, wherein $R_1$ represents a hydrogen atom, a lower alkyl group, a cyclo $C_{3-8}$ alkyl lower alkyl group, or a lower alkoxy lower alkyl group;

$R_2$ represents a hydrogen atom, a lower alkyl group, or a halogen-substituted lower alkyl group;

$R_3$ represents a phenyl group, a furyl group, a thienyl group, or a pyridyl group, each of the groups optionally being substituted with one or more groups selected from the group consisting of the following (1) to (16) on the aromatic or heterocyclic ring represented by the above $R_3$:

(1) lower alkyl groups,
(2) lower alkoxy groups,
(3) halogen-substituted lower alkoxy groups,
(4) a phenoxy group,
(5) lower alkylthio groups,
(6) a hydroxy group,
(7) hydroxy lower alkyl groups,
(8) halogen atoms,
(9) lower alkanoyl groups,
(10) lower alkoxycarbonyl groups,
(11) amino groups optionally substituted with one or more lower alkyl groups,
(12) carbamoyl groups optionally substituted with one or more lower alkyl groups,
(13) cyclo $C_{3-8}$ alkyl lower alkoxy groups,

(14) pyrrolidinyl carbonyl groups,
(15) morpholinyl carbonyl groups, and
(16) a carboxyl group;
$R_4$ represents a halogen atom;
$R_5$ represents a hydrogen atom or a halogen atom;
$R_6$ represents a hydrogen atom; and
$R_7$ represents any one of groups (1) to (15) below:
(1) a hydroxy group,
(2) a halogen atom,
(3) a lower alkoxy group,
(4) a halogen-substituted lower alkoxy group,
(5) a hydroxy lower alkoxy group,
(6) a lower alkoxy lower alkoxy group,
(7) an amino group optionally substituted with one or more members selected from the group consisting of lower alkyl groups, lower alkoxy lower alkyl groups, and cyclo $C_{3-8}$ alkyl groups,
(8) an amino lower alkoxy group optionally substituted on the amino group with one or more members selected from the group consisting of lower alkyl groups, lower alkanoyl groups, lower alkyl sulfonyl groups, and carbamoyl groups optionally substituted with one or more lower alkyl groups,
(9) a cyclo $C_{3-8}$ alkyloxy group,
(10) a cyclo $C_{3-8}$ alkyl lower alkoxy group,
(11) a tetrahydrofuryl lower alkoxy group,
(12) a lower alkylthio group,
(13) a heterocyclic group selected from the group consisting of morpholinyl groups, pyrrolidinyl groups, furyl groups, thienyl groups, and benzothienyl groups,
(14) a phenyl lower alkoxy lower alkoxy group, and
(15) a pyrrolidinyl carbonyl group.

Item 2. A quinolone compound of General Formula (1) or a salt thereof according to item 1,
wherein $R_1$ represents a hydrogen atom or a lower alkyl group;
$R_2$ represents a hydrogen atom or a lower alkyl group;
$R_3$ represents a phenyl group or a pyridyl group, each of the groups optionally being substituted with one or two groups selected from the group consisting of the following (1), (2), (6), and (8) on the aromatic or heterocyclic ring represented by the above $R_3$:
(1) lower alkyl groups,
(2) lower alkoxy groups,
(6) a hydroxy group, and
(8) halogen atoms;
$R_4$ represents a halogen atom;
$R_5$ represents a hydrogen atom;
$R_6$ represents a hydrogen atom; and
$R_7$ represents any one of groups (3), (4), and (7) below:
(3) a lower alkoxy group,
(4) a halogen-substituted lower alkoxy group, and
(7) an amino group optionally substituted with one or two lower alkyl groups Item 3. A quinolone compound of General Formula (1) or a salt thereof according to item 2 selected from the group consisting of:
5-fluoro-3-(4-methoxyphenyl)-2-methyl-8-propoxy-1H-quinolin-4-one,
5-fluoro-3-(4-methoxyphenyl)-1-methyl-8-propoxy-1H-quinolin-4-one,
3-(2,4-dimethoxyphenyl)-5-fluoro-8-propoxy-1H-quinolin-4-one,
5-fluoro-8-isopropoxy-3-(4-methoxyphenyl)-1H-quinolin-4-one,
3-(2,4-dichlorophenyl)-5-fluoro-8-propoxy-1H-quinolin-4-one,
8-ethoxy-5-fluoro-3-(4-methoxyphenyl)-1H-quinolin-4-one,
5-fluoro-3-(4-methoxy-2-methylphenyl)-8-propoxy-1H-quinolin-4-one,
5-fluoro-3-(4-methoxyphenyl)-8-propoxy-1H-quinolin-4-one,
5-fluoro-3-(2-fluoro-4-methoxyphenyl)-8-propoxy-1H-quinolin-4-one,
5-fluoro-3-(4-hydroxyphenyl)-8-propoxy-1H-quinolin-4-one,
8-cyclopropylmethoxy-5-fluoro-3-(4-methoxyphenyl)-1H-quinolin-4-one,
5-fluoro-8-propoxy-3-pyridin-4-yl-1H-quinolin-4-one,
5-fluoro-3-(4-methoxyphenyl)-8-(N-methyl-N-propylamino)-1H-quinolin-4-one, and
5-fluoro-3-(4-methoxyphenyl)-8-(4,4,4-trifluorobutoxy)-1H-quinolin-4-one.

Item 4. A pharmaceutical composition comprising a quinolone compound of General Formula (1) or a salt thereof according to item 1 as an active ingredient and a pharmaceutically acceptable carrier.

Item 5. A prophylactic and/or therapeutic agent for neurodegenerative diseases, diseases induced by neurological dysfunction, or diseases induced by deterioration of mitochondrion function, comprising as an active ingredient a quinolone compound of General Formula (1) or a salt thereof according to item 1.

Item 6. A prophylactic and/or therapeutic agent according to item 5, wherein the neurodegenerative disease is selected from the group consisting of Parkinson's disease, Parkinson's syndrome, juvenile parkinsonism, striatonigral degeneration, progressive supranuclear palsy, pure akinesia, Alzheimer's disease, Pick's disease, prion disease, corticobasal degeneration, diffuse Lewy body disease, Huntington's disease, chorea-acanthocytosis, benign hereditary chorea, paroxysmal choreoathetosis, essential tremor, essential myoclonus, Gilles de la Tourette's syndrome, Rett's syndrome, degenerative ballism, dystonia musculorum deformance, athetosis, spasmodic torticollis, Meige syndrome, cerebral palsy, Wilson's disease, Segawa's disease, Hallervorden-Spatz syndrome, neuroaxonal dystrophy, pallidal atrophy, spino-cerebellar degeneration, cerebral cortical atrophy, Holmes-type cerebellar atrophy, olivopontocerebellar atrophy, hereditary olivopontocerebellar atrophy, Joseph disease, dentatorubropallidoluysian atrophy, Gerstmann-Straussler-Scheinker disease, Friedreich's Ataxia, Roussy-Levy syndrome, May-White syndrome, congenital cerebellar ataxia, hereditary episodic ataxia, ataxia telangiectasia, amyotrophic lateral sclerosis, progressive bulbar palsy, spinal progressive muscular atrophy, spinobulbar muscular atrophy, Werdnig-Hoffmann disease, Kugelberg-Welander disease, hereditary spastic paraparesis, syringomyelia, syringobulbia, Arnold-Chiari malformation, Stiffman syndrome, Klippel-Feil syndrome, Fazio-Londe syndrome, lower myelopathy, Dandy-Walker syndrome, spina bifida, Sjogren-Larsson syndrome, radiation myelopathy, age-related macular degeneration, and cerebral apoplexy selected from the group consisting of cerebral infarction and cerebral hemorrhage.

Item 7. A prophylactic and/or therapeutic agent according to item 5, wherein the disease induced by neurological dysfunction is selected from the group consisting of spinal cord injury, chemotherapy-induced neuropathy, diabetic neuropathy, radiation damage, and demyelinating diseases selected from the group consisting of multiple sclerosis, acute disseminated encephalomyelitis, transverse myelitis, progressive multifocal leucoencephalopathy, subacute sclerosing panencephalitis, chronic inflammatory demyelinating polyneuropathy and Guillain-Barre syndrome.

Item 8. A prophylactic and/or therapeutic agent according to item 5, wherein the disease induced by deterioration of mitochondrion function is selected from the group consisting of Pearson's syndrome, diabetes, deafness, malignant migraine, Leber's disease, MELAS, MERRF, MERRF/MELAS overlap syndrome, NARP, pure myopathy, mitochondrial cardiomyopathy, myopathy, dementia, gastrointestinal ataxia, acquired sideroblastic anemia, aminoglycoside-induced hearing loss, complex III deficiency due to inherited variants of cytochrome b, multiple symmetrical lipomatosis, ataxia, myoclonus, retinopathy, MNGIE, ANTI disease, Twinkle disease, POLG disease, recurrent myoglobinuria, SANDO, ARCO, complex I deficiency, complex II deficiency, optic nerve atrophy, fatal infantile complex IV deficiency, mitochondrial DNA deficiency, mitochondrial DNA deficiency syndrome, Leigh's encephalomyelopathy, chronic-progressive-external-ophthalmoplegia syndrome (CPEO), Kearns-Sayre syndrome, encephalopathy, lactacidemia, myoglobinuria, drug-induced mitochondrial diseases, schizophrenia, major depression disorder, bipolar I disorder, bipolar II disorder, mixed episode, dysthymic disorders, atypical depression, seasonal affective disorders, postpartum depression, minor depression, recurrent brief depressive disorder, intractable depression/chronic depression, double depression and acute renal failure.

Item 9. Use of a quinolone compound of General Formula (1) or a salt thereof according to item 1 as a drug.

Item 10. A method for treating or preventing neurodegenerative diseases, diseases induced by neurological dysfunction, or diseases induced by deterioration of mitochondrion function, comprising administering a quinolone compound of General Formula (1) or a salt thereof according to item 1 to a human or an animal.

Item 11. A process for producing a quinolone compound of General Formula (1)

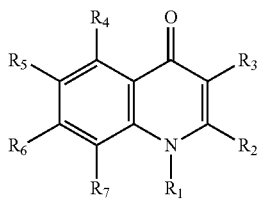

or a salt thereof, wherein $R_1$, $R_2$, $R_3$, $R_4$, $R_5$, $R_6$ and $R_7$ are each defined above in item 1, comprising reacting a compound represented by General Formula (4)

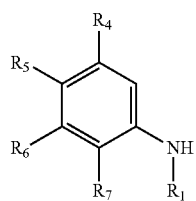

wherein $R_1$, $R_4$, $R_5$, $R_6$ and $R_7$ are each defined above in item 1, with a compound represented by General Formula (5)

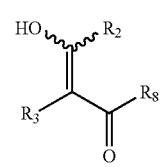

wherein $R_2$ and $R_3$ are each defined above in item 1, and $R_8$ represents a lower alkoxy group, thereby giving an intermediate compound represented by General Formula (6)

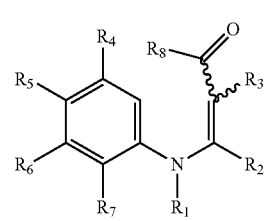

wherein $R_1$, $R_2$, $R_3$, $R_4$, $R_5$, $R_6$, $R_7$ and $R_8$ are each defined above; and subjecting the resulting compound to a cyclization reaction.

Specific examples of groups in General Formula (1) are as follows.

Examples of lower alkyl groups include straight or branched $C_{1-6}$ (preferably $C_{1-4}$) alkyl groups such as methyl, ethyl, n-propyl, isopropyl, n-butyl, isobutyl, tert-butyl, sec-butyl, n-pentyl, 1-ethylpropyl, isopentyl, neopentyl, n-hexyl, 1,2,2-trimethylpropyl, 3,3-dimethylbutyl, 2-ethylbutyl, isohexyl, 3-methylpentyl, etc.

Examples of $C_{3-8}$ cycloalkyl groups include cyclopropyl, cyclobutyl, cyclopentyl, cyclohexyl, cycloheptyl, cyclooctyl, etc.

Examples of cyclo $C_{3-8}$ alkyl lower alkyl groups include the lower alkyl groups substituted with one to three (preferably one) cyclo $C_{3-8}$ alkyl group(s) described above.

Examples of lower alkoxy groups include straight or branched $C_{1-6}$ (preferably $C_{1-4}$) alkoxy groups such as methoxy, ethoxy, n-propoxy, isopropoxy, n-butoxy, isobutoxy, tert-butoxy, sec-butoxy, n-pentyloxy, isopentyloxy, neopentyloxy, n-hexyloxy, isohexyloxy, 3-methylpentyloxy, etc.

Examples of lower alkoxy lower alkyl groups include the lower alkyl groups substituted with one to three (preferably one) lower alkoxy group(s) described above.

Examples of halogen atoms include fluorine, chlorine, bromine, and iodine.

Examples of halogen-substituted lower alkyl groups include the lower alkyl groups substituted with one to seven halogen atom(s), preferably one to three halogen atom(s). Examples thereof include fluoromethyl, difluoromethyl, trifluoromethyl, chloromethyl, dichloromethyl, trichloromethyl, bromomethyl, dibromomethyl, dichlorofluoromethyl, 2,2-difluoroethyl, 2,2,2-trifluoroethyl, pentafluoroethyl, 2-fluoroethyl, 2-chloroethyl, 3,3,3-trifluoropropyl, heptafluoropropyl, 2,2,3,3,3-pentafluoropropyl, heptafluoroisopropyl, 3-chloropropyl, 2-chloropropyl, 3-bromopropyl, 4,4,4-trifluorobutyl, 4,4,4,3,3-pentafluorobutyl, 4-chlorobutyl, 4-bromobutyl, 2-chlorobutyl, 5,5,5-trifluoropentyl, 5-chloropentyl, 6,6,6-trifluorohexyl, 6-chlorohexyl, perfluorohexyl, etc.

Examples of halogen-substituted lower alkoxy groups include the lower alkoxy groups substituted with one to seven halogen atom(s), preferably one to three halogen atom(s).

Examples thereof include fluoromethoxy, difluoromethoxy, trifluoromethoxy, chloromethoxy, dichloromethoxy, trichloromethoxy, bromomethoxy, dibromomethoxy, dichlorofluoromethoxy, 2,2,2-trifluoroethoxy, pentafluoroethoxy, 2-chloroethoxy, 3,3,3-trifluoropropoxy, heptafluoropropoxy, heptafluoroisopropoxy, 3-chloropropoxy, 2-chloropropoxy, 3-bromopropoxy, 4,4,4-trifluorobutoxy, 4,4,4,3,3-pentafluorobutoxy, 4-chlorobutoxy, 4-bromobutoxy, 2-chlorobutoxy, 5,5,5-trifluoropentoxy, 5-chloropentoxy, 6,6,6-trifluorohexyloxy, 6-chlorohexyloxy, etc.

Examples of lower alkylthio groups include alkylthio groups wherein the alkyl moiety is the lower alkyl group mentioned above.

Examples of hydroxy lower alkyl groups include the above-mentioned lower alkyl groups substituted with one to three (preferably one) hydroxy group(s).

Examples of lower alkanoyl groups include straight or branched $C_{1-6}$ (preferably $C_{1-4}$) alkanoyl groups such as formyl, acetyl, propionyl, butyryl, isobutyryl, pentanoyl, tert-butylcarbonyl, hexanoyl, etc.

Examples of lower alkoxycarbonyl groups include alkoxycarbonyl groups wherein the alkoxy moiety is the lower alkoxy group mentioned above.

Examples of amino groups optionally substituted with one or more lower alkyl groups include amino groups optionally substituted with one or two lower alkyl group(s) described above.

Examples of carbamoyl groups optionally substituted with one or more lower alkyl groups include carbamoyl groups optionally substituted with one or two lower alkyl group(s) described above.

Examples of cyclo $C_{3-8}$ alkyl lower alkyl groups include the above-mentioned lower alkyl groups substituted with one to three (preferable one) cyclo $C_{3-8}$ alkyl group(s) described above.

Examples of hydroxy lower alkoxy groups include the above-mentioned lower alkoxy groups substituted with one to three (preferably one) hydroxy group(s).

Examples of lower alkoxy lower alkoxy groups include the above-mentioned lower alkoxy groups substituted with one to three (preferably one) lower alkoxy group(s) described above.

Examples of amino groups optionally substituted with one or more members selected from the group consisting of lower alkyl groups, lower alkoxy lower alkyl groups, and cyclo $C_{3-8}$ alkyl groups include amino groups optionally substituted with one or two members selected from the group consisting of the above-mentioned lower alkyl groups, the above-mentioned lower alkoxy lower alkyl groups, and the above-mentioned cyclo $C_{3-8}$ alkyl groups.

Examples of lower alkyl sulfonyl groups include alkyl sulfonyl groups wherein the alkyl moiety is the lower alkyl group mentioned above.

Examples of amino lower alkoxy groups optionally substituted on an amino group with one or more members selected from the group consisting of lower alkyl groups, lower alkanoyl groups, lower alkyl sulfonyl groups, and carbamoyl groups optionally substituted with one or more lower alkyl groups include the lower alkoxy groups substituted with one to three (preferably one) amino group(s). Here, the amino lower alkoxy group is optionally substituted on an amino group with one or two members selected from the group consisting of the above-mentioned lower alkyl groups, the above-mentioned lower alkanoyl groups, the above-mentioned lower alkyl sulfonyl groups, carbamoyl groups optionally substituted with one or more lower alkyl groups mentioned above.

Examples of cyclo $C_{3-8}$ alkyloxy groups include groups in which the cyclo $C_{3-8}$ alkyl group and an oxygen atom are bonded.

Examples of tetrahydrofuryl lower alkoxy groups include the above-mentioned lower alkoxy groups substituted with one to three (preferably one) tetrahydrofuryl group(s).

Examples of lower alkylthio groups include alkylthio groups wherein the alkyl moiety is the lower alkyl group mentioned above.

Examples of phenyl lower alkoxy groups include the above-mentioned lower alkoxy groups substituted with one to three (preferably one) phenyl group(s).

Examples of phenyl lower alkoxy lower alkoxy groups include the above-mentioned lower alkoxy groups substituted with one to three phenyl lower alkoxy group(s) (preferably one) described above.

The process of producing the compound of the invention is described below in detail.

The quinolone compound represented by General Formula (1) (hereinafter also referred to as Compound (1)) can be produced by various methods; for example, by a method according to the following Reaction Scheme 1 or 2.

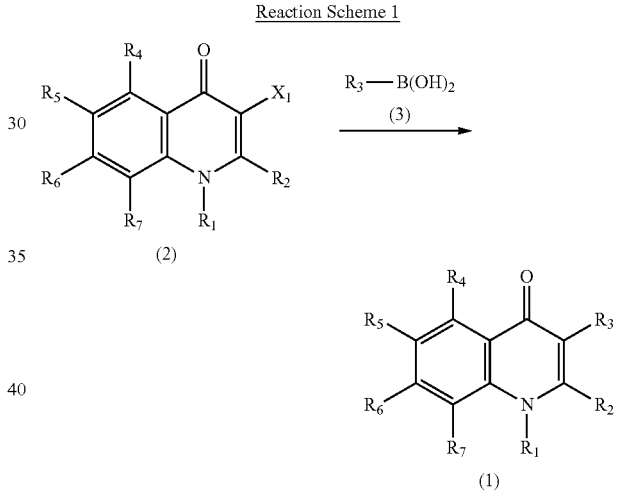

wherein $R_1$, $R_2$, $R_3$, $R_4$, $R_5$, $R_6$, and $R_7$ are as defined above, and $X_1$ represents a halogen atom.

Examples of halogen atoms represented by $X_1$ include fluorine, chlorine, bromine, and iodine.

Preferable leaving groups in the reaction include halogen. Among these, iodine is particularly preferable.

Compound (1) can be prepared by reacting the compound of General Formula (2) and the compound of General Formula (3) in an inert solvent or without using any solvents, in the presence or absence of a basic compound, in the presence of a palladium catalyst.

Examples of inert solvents include water; ether-based solvents such as dioxane, tetrahydrofuran, diethyl ether, 1,2-dimethoxyethane, diethylene glycol dimethyl ether, and ethylene glycol dimethyl ether; aromatic hydrocarbon-based solvents such as benzene, toluene, and xylene; lower alcohol-based solvents such as methanol, ethanol, and isopropanol; ketone-based solvents such as acetone and methyl ethyl ketone; and polar solvents such as N,N-dimethylformamide (DMF), dimethyl sulfoxide (DMSO), hexamethylphosphoric triamide, and acetonitrile. These inert solvents can be used singly or in combinations of two or more.

Palladium compounds used in the reaction are not particularly limited, but include, for example, tetravalent palladium catalysts such as sodium hexachloropalladiumate (IV) tetrahydrate and potassium hexachloropalladiumate (IV); divalent palladium catalysts such as palladium (II) chloride, palladium (II) bromide, palladium (II) acetate, palladium (II) acetylacetonato, dichlorobis(benzonitrile)palladium (II), dichlorobis(acetonitrile)palladium (II), dichlorobis(triphenylphosphine)palladium (II), dichlorotetraammine palladium (II), dichloro(cycloocta-1,5-diene)palladium (II), palladium (II) trifluoroacetate, and 1,1'-bis(diphenylphosphino) ferrocene dichloropalladium (II)-dichloromethane complex; zerovalent palladium catalysts such as tris(dibenzylideneacetone)$_2$ palladium (0), tris(dibenzylideneacetone)$_2$ palladium (0) chloroform complex, and tetrakis(triphenylphosphine) palladium (0), etc. These palladium compounds are used singly or in combinations of two or more.

In the reaction, the amount of the palladium catalyst is not particularly limited, but is typically in the range from 0.000001 to 20 moles in terms of palladium relative to 1 mol of Compound (2). The amount of the palladium catalyst is preferably in the range from 0.0001 to 5 moles in terms of palladium relative to 1 mol of Compound (2).

This reaction advantageously proceeds in the presence of a suitable ligand. Examples of ligands of the palladium catalyst include, for example, 2,2'-bis(diphenylphosphino)-1,1'-binaphthyl(BINAP), tri-o-tolylphosphine, bis(diphenylphosphino)ferrocene, triphenylphosphine, tri-t-butylphosphine, and 9,9-dimethyl-4,5-bis(diphenylphosphino)xanthene (XANTPHOS). These ligands are used singly or in combinations of two or more.

The proportion of the palladium catalyst and ligand is not particularly limited. The amount of the ligand is about 0.1 to about 100 moles per mole of the palladium catalyst, and preferably about 0.5 to about 15 moles per mole of the palladium catalyst.

Various known inorganic and organic bases can be used as basic compounds.

Inorganic bases include, for example, alkali metal hydroxides such as sodium hydroxide, potassium hydroxide, cesium hydroxide, and lithium hydroxide; alkali metal carbonates such as sodium carbonate, potassium carbonate, cesium carbonate, and lithium carbonate; alkali metal hydrogencarbonates such as lithium hydrogencarbonate, sodium hydrogencarbonate, and potassium hydrogencarbonate; alkali metals such as sodium and potassium; phosphates such as sodium phosphate and potassium phosphate; amides such as sodium amide; and alkali metal hydrides such as sodium hydride and potassium hydride.

Organic bases include, for example, alkali metal lower alkoxides such as sodium methoxide, sodium ethoxide, sodium t-butoxide, potassium methoxide, potassium ethoxide, and potassium t-butoxide, and amines such as triethylamine, tripropylamine, pyridine, quinoline, piperidine, imidazole, N-ethyldiisopropylamine, dimethylaminopyridine, trimethylamine, dimethylaniline, N-methylmorpholine, 1,5-diazabicyclo[4.3.0]non-5-ene (DBN), 1,8-diazabicyclo[5.4.0]undec-7-ene (DBU), 1,4-diazabicyclo[2.2.2]octane (DABCO), etc.

Such basic compounds can be used singly or in combinations of two or more. More preferable basic compounds used in the reaction include alkali metal carbonates such as sodium carbonate, potassium carbonate, cesium carbonate, and lithium carbonate.

A basic compound is usually used in an amount of 0.5 to 10 moles per mole of Compound (2), and preferably 0.5 to 6 moles per mole of Compound (2).

Compound (3) is usually used in an amount of at least about 1 mole per mole of Compound (2), and preferably about 1 to about 5 moles per mole of Compound (2).

The reaction can be conducted under normal pressure, under inert gas atmospheres including nitrogen, argon, etc., or under increased pressure.

The reaction proceeds usually at room temperature to 200° C., and preferably at room temperature to 150° C., and is usually completed in about 1 to about 30 hours. The reaction is also achieved by heating at 100 to 200° C. for 5 minutes to 1 hour using a microwave reactor.

The compound represented by General Formula (3), which is used as a starting material in Reaction Scheme 1 is an easily available known compound. The compound represented by General Formula (2) includes a novel compound, and the compound is produced in accordance with Reaction Scheme 6 shown below.

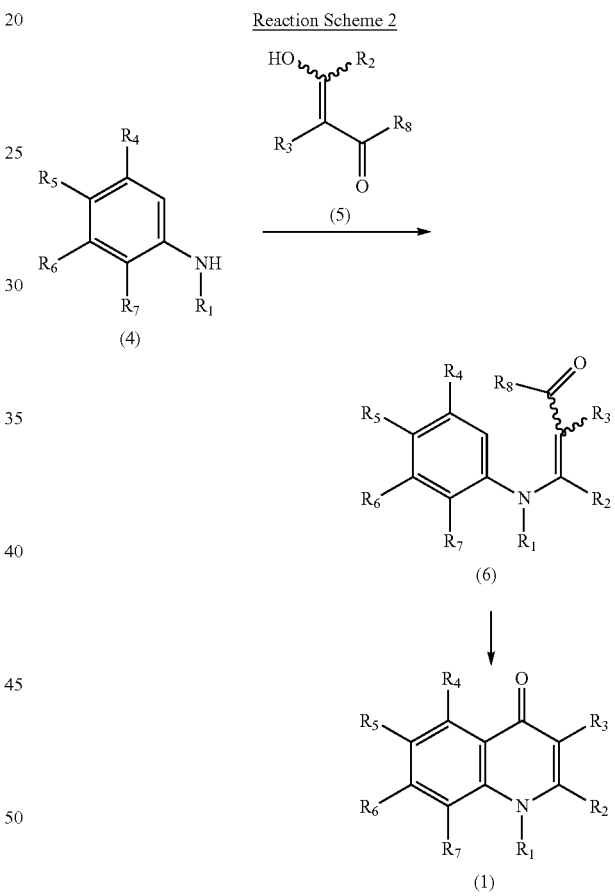

Reaction Scheme 2 wherein $R_1$, $R_2$, $R_3$, $R_4$, $R_5$, $R_6$, and $R_7$ are as defined above, and $R_8$ represents a lower alkoxy group.

The lower alkoxy group represented by $R_8$ in General Formula (5) has the same definition as described above.

The compounds represented by General Formulae (4) and (5) are reacted in an inert solvent or without using any solvents, in the presence or absence of an acid catalyst, thereby giving an intermediate compound represented by General Formula (6). Then, the resulting compound was cyclized to produce the compound represented by General Formula (1).

Examples of inert solvents include water; ether-based solvents such as dioxane, tetrahydrofuran, diethyl ether, 1,2-dimethoxyethane, diethylene glycol dimethyl ether, and ethylene glycol dimethyl ether; aromatic hydrocarbon-based solvents such as benzene, toluene, and xylene; lower alcohol-based solvents such as methanol, ethanol, and isopropanol; and polar solvents such as N,N-dimethylformamide (DMF), dimethyl sulfoxide (DMSO), hexamethylphosphoric triamide, and acetonitrile. These inert solvents can be used singly or in combinations of two or more.

Various kinds of known acid catalysts can be used, including toluenesulfonic acid, methanesulfonic acid, xylene sulfonic acid, sulfuric acid, glacial acetic acid, boron trifluoride, acidic ion exchangers, etc. These acid catalysts can be used singly or in combinations of two or more.

Among such acids, acidic ion exchangers are preferably used. Examples of acidic ion exchangers include polymeric cation exchangers available from the market such as Lewatit S100, Zeo-karb 225, Dowex 50, Amberlite IR120, or Amberlyst 15 and like styrene sulfonic acid polymers; Lewatit PN, Zeo-karb 215 or 315, and like polysulfonic acid condensates; Lewatit CNO, Duolite CS100, and like m-phenolic carboxylic acid resins; or Permutit C, Zeo-karb 226 or Amberlite IRC 50, and like polyacrylates. Of these, Amberlyst 15 is particularly preferred.

An oxide catalyst is usually used in an amount of 0.0001 to 100 moles per mole of Compound (4), and preferably 0.5 to 6 moles per mole of Compound (4).

In Reaction Scheme 2, Compound (5) is usually used in an amount of at least about 1 mole per mole of Compound (4), and preferably about 1 to about 5 moles per mole of Compound (4).

The reaction can be conducted under normal pressure, under inert gas atmospheres including nitrogen, argon, etc., or under increased pressure.

The reaction proceeds usually at room temperature to 200° C., and preferably at room temperature to 150° C. During the reaction, azeotropic removal of water is conducted until the reaction water generation is completed. The reaction is usually finished in about 1 to about 30 hours.

The process of producing the compound of General Formula (1) via a cyclization reaction of the intermediate compound represented by General Formula (6) can be employed by heating the compound in a solvent such as diphenyl ether, or by heating the compound in the absence of a solvent. The reaction is conducted at 150 to 300° C. for 5 minutes to 2 hours.

The compound represented by General Formula (4), used as a starting material in Reaction Scheme 2 described above is a known compound or can be produced easily using a known compound. The compound represented by General Formula (5) includes a novel compound, and the compound is manufactured in accordance with, for example, the methods shown in Reaction Scheme 4 and Reaction Scheme 5 described above.

Reaction Scheme 3

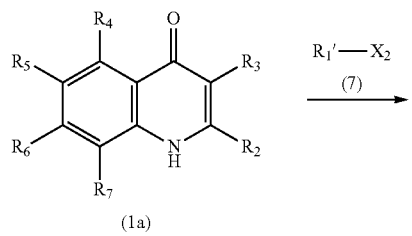

(1a)

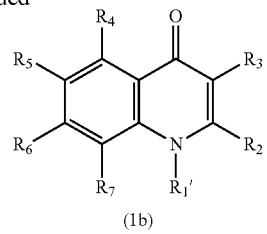

(7)

-continued (1b)

wherein $R_2$, $R_3$, $R_4$, $R_5$, $R_6$, and $R_7$ are as defined above, and $R_1'$ is a group represented by $R_1$ other than hydrogen, and $X_2$ represents a group that undergoes the same substitution reaction as that of a halogen or a halogen atom.

Halogens represented by $X_2$ in General Formula (1a) include the halogen atom described above. Groups that undergo the same substitution reaction as that of the halogen atoms represented by $X_2$ include lower alkyl sulfonyloxy groups, aryl sulfonyloxy groups, aralkyl sulfonyloxy groups, etc.

Examples of lower alkyl sulfonyloxy groups include straight or branched $C_{1-6}$ alkyl sulfonyloxy groups, such as methane sulfonyloxy, ethane sulfonyloxy, n-propane sulfonyloxy, isopropane sulfonyloxy, n-butane sulfonyloxy, tert-butane sulfonyloxy, n-pentane sulfonyloxy, and n-hexane sulfonyloxy.

Examples of aryl sulfonyloxy groups include naphthyl sulfonyloxy and phenyl sulfonyloxy optionally substituted on a phenyl ring with one to three group(s) selected from the group consisting of straight or branched $C_{1-6}$ alkyl groups, straight or branched $C_{1-6}$ alkoxy groups, nitro groups, and halogen atoms as a substituent. Examples of phenyl sulfonyloxy groups optionally substituted with the above substituent(s) include phenyl sulfonyloxy, 4-methylphenyl sulfonyloxy, 2-methylphenyl sulfonyloxy, 4-nitrophenyl sulfonyloxy, 4-methoxyphenyl sulfonyloxy, 2-nitrophenyl sulfonyloxy, 3-chlorophenyl sulfonyloxy, etc. Examples of naphthyl sulfonyloxy groups include α-naphthyl sulfonyloxy, β-naphthyl sulfonyloxy, etc.

Examples of aralkyl sulfonyloxy groups include phenyl-substituted straight or branched $C_{1-6}$ alkyl sulfonyloxy groups that may have, on the phenyl ring, one to three substituent(s) selected from the group consisting of straight or branched $C_{1-6}$ alkyl groups, straight or branched $C_{1-6}$ alkoxy groups, a nitro group and halogen atoms as a substituent, or naphtyl-substituted straight or branched $C_{1-6}$ alkyl sulfonyloxy groups. Examples of alkyl sulfonyloxy groups substituted with the above-mentioned phenyl group(s) include benzyl sulfonyloxy, 2-phenylethyl sulfonyloxy, 4-phenylbutyl sulfonyloxy, 4-methylbenzyl sulfonyloxy, 2-methylbenzyl sulfonyloxy, 4-nitrobenzyl sulfonyloxy, 4-methoxybenzyl sulfonyloxy, 3-chlorobenzyl sulfonyloxy, etc. Examples of alkyl sulfonyloxy groups substituted with the above-mentioned naphthyl group(s) include α-naphthylmethyl sulfonyloxy, β-naphthylmethyl sulfonyloxy, etc.

The compound represented by General Formula (1b) can be produced by the reaction of the compound represented by General Formula (1a) with the compound represented by General Formula (7) in an inert solvent or without using any solvents, in the presence or absence of a basic compound.

Examples of inert solvents include water; ether-based solvents such as dioxane, tetrahydrofuran, diethyl ether, 1,2-dimethoxyethane, diethylene glycol dimethyl ether, and ethylene glycol dimethyl ether; aromatic hydrocarbon-based solvents such as benzene, toluene, and xylene; lower alcohol-based solvents such as methanol, ethanol, and isopropanol; ketone-based solvents such as acetone and methyl ethyl ketone; and polar solvents such as N,N-dimethylformamide (DMF), dimethyl sulfoxide (DMSO), hexamethylphosphoric triamide, and acetonitrile. These inert solvents can be used singly or in combinations of two or more.

As a basic compound, various known inorganic bases and organic bases can be used.

Inorganic bases include, for example, alkali metal hydroxides such as sodium hydroxide, potassium hydroxide, cesium hydroxide, and lithium hydroxide; alkali metal carbonates such as sodium carbonate, potassium carbonate, cesium carbonate, and lithium carbonate; alkali metal hydrogen carbonates such as lithium hydrogen carbonate, sodium hydrogen carbonate, and potassium hydrogen carbonate; alkali metals such as sodium and potassium; amides such as sodium amide; and alkali metal hydrides such as sodium hydride and potassium hydride.

Organic bases include, for example, alkali metal lower alkoxides such as sodium methoxide, sodium ethoxide, sodium t-butoxide, potassium methoxide, potassium ethoxide, and potassium t-butoxide, and amines such as triethylamine, tripropylamine, pyridine, quinoline, piperidine, imidazole, N-ethyl diisopropylamine, dimethylaminopyridine, trimethylamine, dimethylaniline, N-methylmorpholine, 1,5-diazabicyclo[4.3.0]non-5-ene (DBN), 1,8-diazabicyclo[5.4.0]undec-7-ene (DBU), 1,4-diazabicyclo[2.2.2]octane (DABCO), etc.

Such basic compounds can be used singly or in combinations of two or more. More preferable basic compounds used in the reaction include inorganic bases such as sodium hydride and potassium hydride.

A basic compound is usually used in an amount of 0.5 to 10 moles per mole of Compound (1a), and preferably 0.5 to 6 moles per mole of Compound (1a).

In Reaction Scheme 1, Compound (7) usually used in an amount of at least about 1 mole per mole of Compound (1a), and preferably about 1 to about 5 moles per mole of Compound (1a).

The reaction can be conducted under normal pressure, under inert gas atmospheres including nitrogen, argon, etc., or under increased pressure.

The reaction proceeds usually at 0° C. to 200° C., and preferably at room temperature to 150° C., and is usually completed in about 1 to about 30 hours.

The compound represented by General Formula (7), which is used as a starting material in Reaction Scheme 3 is an easily available known compound.

Compound (5) and Compound (2), which are the starting materials of the compound of the invention, include novel compounds, and can be produced by various methods; for example, by methods according to the following Reaction Schemes 4 to 6.

Reaction Scheme 4

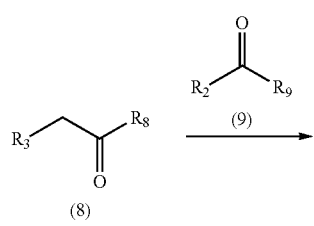

-continued

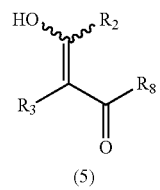

wherein $R_2$, $R_3$, and $R_8$ are as defined above, and $R_9$ represents a lower alkoxy group.

The lower alkoxy group represented by $R_9$ in General Formula (9) has the same definition as described above.

The compound represented by General Formula (5) can be produced by the reaction of the compound represented by General Formula (8) with the compound represented by General Formula (9) in an inert solvent or without using any solvents, in the presence or absence of a basic compound.

Examples of inert solvents include water; ether-based solvents such as dioxane, tetrahydrofuran, diethyl ether, 1,2-dimethoxyethane, diethylene glycol dimethyl ether, and ethylene glycol dimethyl ether; aromatic hydrocarbon-based solvents such as benzene, toluene, and xylene; lower alcohol-based solvents such as methanol, ethanol, and isopropanol; ketone-based solvents such as acetone and methyl ethyl ketone; and polar solvents such as N,N-dimethylformamide (DMF), dimethyl sulfoxide (DMSO), hexamethylphosphoric triamide, and acetonitrile. These inert solvents can be used singly or in combinations of two or more.

As a basic compound, various known inorganic bases and organic bases can be used.

Inorganic bases include, for example, alkali metal hydroxides such as sodium hydroxide, potassium hydroxide, cesium hydroxide, and lithium hydroxide; alkali metal carbonates such as sodium carbonate, potassium carbonate, cesium carbonate, and lithium carbonate; alkali metal hydrogencarbonates such as lithium hydrogencarbonate, sodium hydrogencarbonate, and potassium hydrogencarbonate; alkali metals such as sodium and potassium; amides such as sodium amide; and inorganic bases of alkali metal hydrides such as sodium hydride and potassium hydride.

Organic bases include, for example, alkali metal lower alkoxides such as sodium methoxide, sodium ethoxide, sodium t-butoxide, potassium methoxide, potassium ethoxide, and potassium t-butoxide; and amines such as triethylamine, tripropylamine, pyridine, quinoline, piperidine, imidazole, N-ethyldiisopropylamine, dimethylaminopyridine, trimethylamine, dimethylaniline, N-methylmorpholine, 1,5-diazabicyclo[4.3.0]non-5-ene (DBN), 1,8-diazabicyclo[5.4.0]undec-7-ene (DBU), 1,4-diazabicyclo[2.2.2]octane (DABCO), etc.

Such basic compounds can be used singly or in combinations of two or more. More preferable basic compounds used in the reaction include inorganic bases such as sodium hydride and potassium hydride.

A basic compound is usually used in an amount of about 1 to about 10 moles per mole of Compound (8), and preferably about 1 to about 6 moles per mole of Compound (8)

In Reaction Scheme 4, Compound (9) is usually used in an amount of at least about 1 mole per mole of Compound (8), and preferably about 1 to about 5 moles per mole of Compound (8).

The reaction can be conducted under normal pressure, under inert gas atmospheres including nitrogen, argon, etc., or under increased pressure.

The reaction proceeds usually at room temperature to 200° C., and preferably at room temperature to 150° C., and is usually completed in about 1 to about 30 hours.

The compounds represented by General Formulae (8) and (9), which are used as starting materials in Reaction Scheme 4, are easily available known compounds.

Reaction Scheme 5

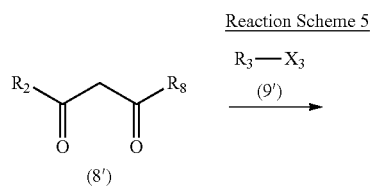

solvents, in the presence of a basic compound such as cesium carbonate and a copper catalyst such as copper iodide.

Examples of inert solvents include polar solvents such as N,N-dimethylformamide (DMF), dimethyl sulfoxide (DMSO), hexamethylphosphoric triamide, and acetonitrile. These inert solvents can be used singly or in combinations of two or more.

The reaction may be conducted in the presence of amino acids such as L-proline.

The reaction can be conducted under normal pressure, under inert gas atmospheres including nitrogen, argon, etc., or under increased pressure.

The reaction proceeds usually at room temperature to 200° C., and preferably at room temperature to 150° C., and is usually completed in about 1 to about 30 hours.

The above reaction is specifically shown in Reference Example 58 below.

The compounds represented by General Formulae (8') and (9') used as starting materials in Reaction Scheme 5 described above are known compounds, or can be produced easily using known compounds.

Reaction Scheme 6

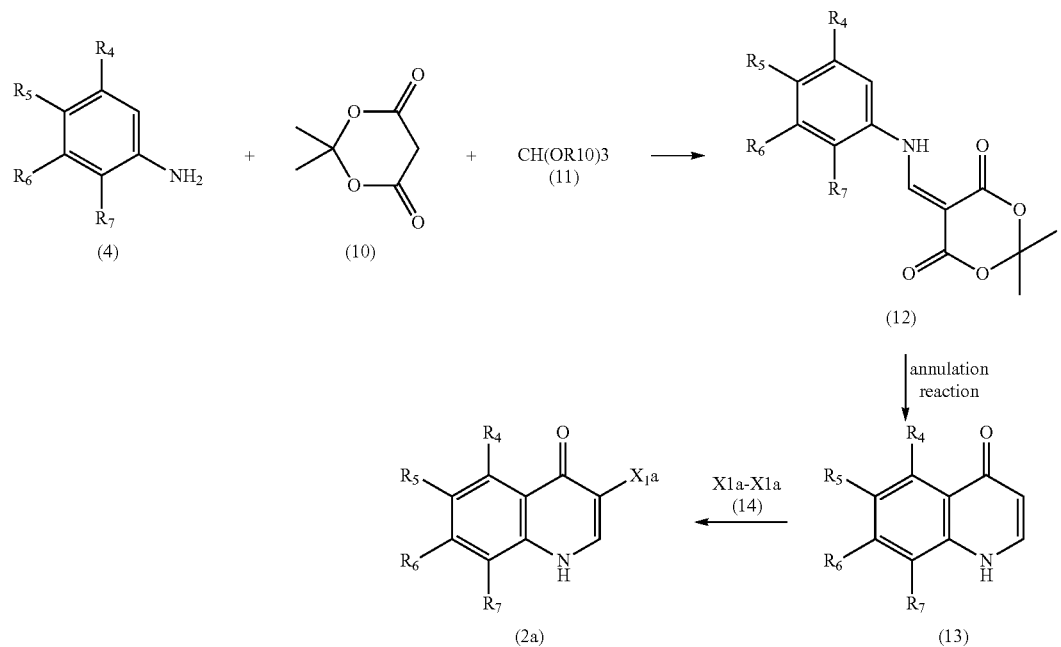

-continued

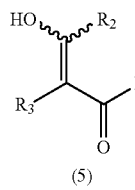

(5)

wherein $R_2$, $R_3$, and $R_8$ are as defined above, and $X_3$ represents a halogen atom.

The halogen atom represented by $X_3$ in General Formula (9') has the same definition as described above.

The compound represented by General Formula (5) can be produced by the reaction of the compound represented by General Formula (8') with the compound represented by General Formula (9') in an inert solvent or without using any wherein $R_4$, $R_5$, $R_6$, and $R_7$ are as defined above, and $X_{1a}$ represents a halogen atom. $R_{10}$ represents a lower alkyl group.

The lower alkyl group represented by $R_{10}$ and a halogen atom represented by $X_{1a}$ have the same definitions as described above.

The compound represented by General Formula (12) can be produced by the condensation reaction of the compounds represented by General Formulae (4), (10), and (11) in an inert solvent or without using any solvents.

Examples of inert solvents include water; ether-based solvents such as dioxane, tetrahydrofuran, diethyl ether, 1,2-dimethoxyethane, diethylene glycol dimethyl ether, and ethylene glycol dimethyl ether; halogenated hydrocarbon-based solvents such as methylene chloride, chloroform, 1,2-dichloroethane, and carbon tetrachloride; aromatic hydrocarbon-based solvents such as benzene, toluene, and xylene; lower alcohol-based solvents such as methanol, ethanol, and isopropanol; and polar solvents such as N,N-dimethylformamide (DMF), dimethyl sulfoxide (DMSO), hexamethylphosphoric triamide, and acetonitrile. The compound represented by General Formula (11) can be used as a solvent in place of the solvents mentioned above. These inert solvents can be used singly or in combinations of two or more.

In Reaction Scheme 6, Compound (10) is usually used in an amount of at least 1 mole per mole of Compound (4), and preferably about 1 to about 5 moles per mole of Compound (4).

An excess amount of Compound (11) is used relative to Compound (10).

The reaction can be conducted under normal pressure, under inert gas atmospheres including nitrogen, argon, etc., or under increased pressure.

The reaction proceeds usually at room temperature to 200° C., and preferably at room temperature to 150° C., and is usually completed in about 1 to about 30 hours.

The compound represented by General Formula (13) can be produced by an annulation reaction of the compound represented by General Formula (12) in an inert solvent or without using any solvents.

Examples of inert solvents include ether-based solvents such as diphenyl ether.

The reaction can be conducted under normal pressure, under inert gas atmospheres including nitrogen, argon, etc., or under increased pressure.

The reaction proceeds usually at room temperature to 300° C., and preferably at 150 to 300° C., and is usually completed in about 1 to about 30 hours.

The compound represented by General Formula (2a) can be produced by the reaction of the compound represented by General Formula (13) with the compound represented by General Formula (14) in an inert solvent or without using any solvents, in the presence or absence of a basic compound.

Examples of inert solvents include water; ether-based solvents such as dioxane, tetrahydrofuran, diethyl ether, 1,2-dimethoxyethane, diethylene-glycol dimethyl ether, and ethylene glycol dimethyl ether; aromatic hydrocarbon-based solvents such as benzene, toluene, and xylene; lower alcohol-based solvents such as methanol, ethanol, and isopropanol; ketone-based solvents such as acetone and methyl ethyl ketone; polar solvents such as N,N-dimethylformamide (DMF), dimethyl sulfoxide (DMSO), hexamethylphosphoric triamide, and acetonitrile. These inert solvents can be used singly or in combinations of two or more.

As a basic compound, various known inorganic bases and organic bases can be used.

Inorganic bases include, for example, alkali metal hydroxides such as sodium hydroxide, potassium hydroxide, cesium hydroxide, and lithium hydroxide; alkali metal carbonates such as sodium carbonate, potassium carbonate, cesium carbonate, and lithium carbonate; alkali metal hydrogencarbonates such as lithium hydrogencarbonate, sodium hydrogencarbonate, and potassium hydrogencarbonate; alkali metals such as sodium and potassium; amides such as sodium amide; and alkali metal hydrides such as sodium hydride and potassium hydride Organic bases include, for example, alkali metal alkoxide-based solvents such as sodium methoxide, sodium ethoxide, sodium t-butoxide, potassium methoxide, potassium ethoxide, and potassium t-butoxide; and amines such as triethylamine, tripropylamine, pyridine, quinoline, piperidine, imidazole, N-ethyldiisopropylamine, dimethylaminopyridine, trimethylamine, dimethylaniline, N-methylmorpholine, 1,5-diazabicyclo[4.3.0]non-5-ene (DBN), 1,8-diazabicyclo[5.4.0]undec-7-ene (DBU), 1,4-diazabicyclo[2.2.2]octane (DABCO), etc.

Such basic compounds can be used singly or in combinations of two or more. More preferable basic compounds used in the reaction include alkali metal carbonates such as sodium carbonate, potassium carbonate, cesium carbonate, and lithium carbonate, etc.

A basic compound is usually used in an amount of 0.5 to 10 moles per mole of Compound (13), and preferably 0.5 to 6 moles per mole of Compound (13).

In Reaction Scheme 6, Compound (14) is usually used in an amount of at least 0.5 moles per mole of Compound (13), and preferably about 0.5 to about 5 moles per mole of Compound (13).

The reaction can be conducted under normal pressure, under inert gas atmospheres including nitrogen, argon, etc., or under increased pressure.

The reaction proceeds usually at room temperature to 200° C., and preferably at room temperature to 150° C., and is usually completed in about 1 to about 30 hours.

The compounds represented by General Formulae (10), (11) and (14), which are used as starting materials in Reaction Scheme 6, are easily available known compounds.

The raw material compounds used in each of the reaction schemes described above may include suitable salts, and the objective compounds obtained via each of the reactions may form suitable salts. These preferable salts include the following preferable salts of Compound (1).

Suitable salts of Compound (1) are pharmacologically allowable salts, including metal salts such as alkali metal salts (e.g., sodium salts, potassium salts, and the like); alkaline earth metal salts (e.g., calcium salts, magnesium salts, and the like); ammonium salts; salts of inorganic bases such as alkali metal carbonates (e.g., lithium carbonate, potassium carbonate, sodium carbonate, cesium carbonate, and the like); alkali metal hydrogencarbonates (e.g., lithium hydrogencarbonate, sodium hydrogencarbonate, potassium hydrogencarbonate, and the like); alkali metal hydroxides (e.g., lithium hydroxide, sodium hydroxide, potassium hydroxide, cesium hydroxide, etc.); salts of organic bases such as tri(lower)alkylamine (e.g., trimethylamine, triethylamine, N-ethyldiisopropylamine, and the like), pyridine, quinoline, piperidine, imidazole, picoline, dimethylaminopyridine, dimethylaniline, N-(lower)alkyl-morpholine (e.g., N-methylmorpholine, etc.), 1,5-diazabicyclo[4.3.0]non-5-ene (DBN), 1,8-diazabicyclo[5.4.0]undec-7-ene (DBU), and 1,4-diazabicyclo[2.2.2]octane (DABCO); inorganic acid salts such as hydrochloride, hydrobromide, hydroiodide, sulfate, nitrate, and phosphate; and organic acid salts such as formate, acetate, propionate, oxalate, malonate, succinate, fumarate, maleate, lactate, malate, citrate, tartrate, carbonate, picrate, methanesulfonate, ethanesulfonate, p-toluenesulfonate, and glutamate.

In addition, compounds in the form in which solvate (for example, hydrate, ethanolate, etc.) was added to the starting materials and objective compound shown in each of the reaction schemes are included in each of the general formulae. Preferable solvates include hydrate.

Each of the objective compounds obtained according to the above reaction schemes can be isolated and purified from the reaction mixture by, for example, after cooling the reaction mixture, performing an isolation procedure such as filtration, concentration, extraction, etc., to separate a crude reaction product, and then subjecting the crude reaction product to a usual purification procedure such as column chromatography, recrystallization, etc.

The compound of Formula (1) according to the present invention naturally includes geometrical isomers, stereoisomers, optical isomers, and like isomers.

The following points should be noted regarding the compound of General Formula (1) shown above. When $R_1$ of General Formula (1) represents a hydrogen atom, the compound includes a tautomer of the quinolone ring. That is, when $R_1$ represents a hydrogen atom (1') in the quinolone compound of General Formula (1),

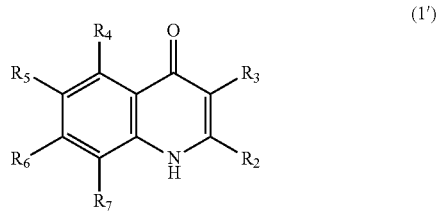

(1')

wherein $R_2$, $R_3$, $R_4$, $R_5$, $R_6$, and $R_7$ are as defined above, the compound of the tautomer can be represented by Formula (1''),

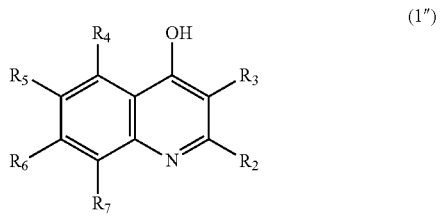

(1'')

wherein $R_2$, $R_3$, $R_4$, $R_5$, $R_6$, and $R_7$ are as defined above.

That is, both of the compounds represented by Formulae (1') and (1'') are in the tautomeric equilibrium state represented by the following balance formula.

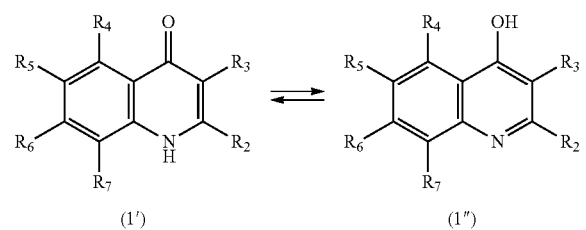

wherein $R_2$, $R_3$, $R_4$, $R_5$, $R_6$, and $R_7$ are as defined above.

Such tautomerism between a 4-quinolone compound and a 4-hydroxyquinoline compound is technically known, and it is obvious for a person skilled in the art that both of the above-described tautomers are balanced and mutually exchangeable.

Therefore, Compound (1) naturally includes the tautomers as mentioned above.

In the specification, the constitutional formula of a 4-quinolone compound is suitably used as a constitutional formula of the objective or starting material including compounds of such tautomers.

The compound of General Formula (1) and the salt thereof are used in the form of general pharmaceutical preparations. The preparations are obtained using typically employed diluents or excipients such as fillers, extenders, binders, wetting agents, disintegrators, surfactants, lubricants, etc. The form of such pharmaceutical preparations can be selected according to the purpose of the therapy. Typical examples include tablets, pills, powders, solutions, suspensions, emulsions, granules, capsules, suppositories, injections (solutions, suspensions, etc.) and the like.

To form tablets, any of various carriers conventionally known in this field can be used. Examples thereof include lactose, white sugar, sodium chloride, glucose, urea, starch, calcium carbonate, kaolin, crystalline cellulose, silicic acid, and other excipients; water, ethanol, propanol, simple syrup, glucose solutions, starch solutions, gelatin solutions, carboxymethylcellulose, shellac, methylcellulose, potassium phosphate, polyvinylpyrrolidone and other binders; dry starch, sodium alginate, agar powder, laminarin powder, sodium hydrogen carbonate, calcium carbonate, fatty acid esters of polyoxyethylene sorbitan, sodium lauryl sulfate, stearic acid monoglycerides, starch, lactose and other disintegrators; white sugar, stearin, cacao butter, hydrogenated oils and other disintegration inhibitors; quaternary ammonium bases, sodium lauryl sulfate and other absorption promoters; glycerol, starch and other wetting agents; starch, lactose, kaolin, bentonite, colloidal silicic acid and other adsorbents; purified talc, stearates, boric acid powder, polyethylene glycol and other lubricants; etc. Further, such tablets may be coated with typical coating materials as required, to prepare, for example, sugar-coated tablets, gelatin-coated tablets, enteric-coated tablets, film-coated tablets, double- or multi-layered tablets, etc.

To form pills, any of various carriers conventionally known in this field can be used. Examples thereof include glucose, lactose, starch, cacao butter, hydrogenated vegetable oils, kaolin, talc and other excipients; gum arabic powder, tragacanth powder, gelatin, ethanol and other binders; laminarin, agar and other disintegrators; etc.

To form suppositories, any of various carriers conventionally known in this field can be used. Examples thereof include polyethylene glycol, cacao butter, higher alcohols, esters of higher alcohols, gelatin, semi synthetic glycerides, etc.

Capsules can be prepared by mixing the active principal compound with the above-mentioned carriers to enclose the former in a hard gelatin capsule, soft gelatin capsule or the like.

To form an injection, a solution, emulsion or suspension is sterilized and preferably made isotonic to blood. Any of the diluents widely used for such forms in this field can be employed to form the injection. Examples of such diluents include water, ethyl alcohol, macrogol, propylene glycol, ethoxylated isostearyl alcohol, polyoxylated isostearyl alcohol, fatty acid esters of polyoxyethylene sorbitan, etc.

In this case, the pharmaceutical preparation may contain sodium chloride, glucose or glycerol in an amount sufficient to prepare an isotonic solution, and may contain typical solubilizers, buffers, analgesic agents, etc. Further, if necessary, the pharmaceutical preparation may contain coloring agents, preservatives, flavors, sweetening agents, etc., and/or other medicines.

The amount of the compound represented by the General Formula (1) and the salt thereof included in the pharmaceutical preparation of the present invention is not limited, and can be suitably selected from a wide range. The proportion is generally about 0.1 to about 70 wt. %, preferably about 0.1 to about 30 wt. % of the pharmaceutical preparation.

The route of administration of the pharmaceutical preparation of the present invention is not particularly limited, and the preparation is administered by a route suitable to the form of the preparation, patient's age, sex and other conditions, and the status of the disease. For example, tablets, pills, solutions, suspensions, emulsions, granules and capsules are administered orally. Injections are intravenously administered singly or as mixed with typical injection transfusions such as glucose solutions, amino acid solutions or the like, or singly administered intramuscularly, intracutaneously, subcutaneously or intraperitoneally, as required. Suppositories are administered intrarectally.

The dosage of the pharmaceutical preparation of the invention is suitably selected according to the method of use, patient's age, sex and other conditions, and severity of the disease. The amount of active principal compound is usually about 0.1 to about 10 mg/kg body weight/day. Further, it is desirable that the pharmaceutical preparation in each unit of the administration form contains the active principal compound in an amount of about 1 to about 200 mg.

The use of the compound of the present invention in combination with L-dopa preparations, dopamine receptor agonists, dopamine metabolism enzyme inhibitors, dopamine release-rate-promoting preparations, central anticholinergic agents, and the like can achieve effects such as dosage reduction, improvement of side effects, increased therapeutic efficacy, etc., which were not attained by known therapies.

Effect of the Invention

The compound of the present invention has protecting and improving mitochondrial functional activity and protecting and repairing neuron activity, etc., and thus is effective in the treatment and prevention of neurodegenerative diseases, diseases relating to neurodegenerative disorder, and diseases relating to mitochondrial dysfunction.

Neurodegenerative diseases include Parkinson's disease, Parkinson's syndrome, juvenile parkinsonism, striatonigral degeneration, progressive supranuclear palsy, pure akinesia, Alzheimer's disease, Pick's disease, prion disease, corticobasal degeneration, diffuse Lewy body disease, Huntington's disease, chorea-acanthocytosis, benign hereditary chorea, paroxysmal choreoathetosis, essential tremor, essential myoclonus, Gilles de la Tourette's syndrome, Rett's syndrome, degenerative ballism, dystonia musculorum deformance, athetosis, spasmodic torticollis, Meige syndrome, cerebral palsy, Wilson's disease, Segawa's disease, Hallervorden-Spatz syndrome, neuroaxonal dystrophy, pallidal atrophy, spino-cerebellar degeneration, cerebral cortical atrophy, Holmes-type cerebellar atrophy, olivopontocerebellar atrophy, hereditary olivopontocerebellar atrophy, Joseph disease, dentatorubropallidoluysian atrophy, Gerstmann-Straussler-Scheinker disease, Friedreich's Ataxia, Roussy-Levy syndrome, May-White syndrome, congenital cerebellar ataxia, hereditary episodic ataxia, ataxia telangiectasia, amyotrophic lateral sclerosis, progressive bulbar palsy, spinal progressive muscular atrophy, spinobulbar muscular atrophy, Werdnig-Hoffmann disease, Kugelberg-Welander disease, hereditary spastic paraparesis, syringomyelia, syringobulbia, Arnold-Chiari malformation, Stiffman syndrome, Klippel-Feil syndrome, Fazio-Londe syndrome, lower myelopathy, Dandy-Walker syndrome, spina bifida, Sjogren-Larsson syndrome, radiation myelopathy, age-related macular degeneration and cerebral apoplexy (e.g., cerebral infarction, cerebral hemorrhage, etc.).

Diseases induced by neurological dysfunction include spinal cord injury, chemotherapy-induced neuropathy, diabetic neuropathy, radiation damage and demyelinating diseases (e.g., multiple sclerosis, acute disseminated encephalomyelitis, transverse myelitis, progressive multifocal leucoencephalopathy, subacute sclerosing panencephalitis, chronic inflammatory demyelinating polyneuropathy, Guillain-Barre syndrome, etc.)

Diseases induced by deterioration of mitochondrion function include Pearson's syndrome, diabetes, deafness, malignant migraine, Leber's disease, MELAS, MERRF, MERRF/MELAS overlap syndrome, NARP, pure myopathy, mitochondrial cardiomyopathy, myopathy, dementia, gastrointestinal ataxia, acquired sideroblastic anemia, aminoglycoside-induced hearing loss, complex III deficiency due to inherited variants of cytochrome b, multiple symmetrical lipomatosis, ataxia, myoclonus, retinopathy, MNGIE, ANTI disease, Twinkle disease, POLG disease, recurrent myoglobinuria, SANDO, ARCO, complex I deficiency, complex II deficiency, optic nerve atrophy, fatal infantile complex IV deficiency, mitochondrial DNA deficiency, mitochondrial DNA deficiency syndrome, Leigh's encephalomyelopathy, chronic-progressive-external-ophthalmoplegia syndrome (CPEO), Kearns-Sayre syndrome, encephalopathy, lactacidemia, myoglobinuria, drug-induced mitochondrial diseases, schizophrenia, major depression disorder, bipolar I disorder, bipolar II disorder, mixed episode, dysthymic disorders, atypical depression, seasonal affective disorders, postpartum depression, minor depression, recurrent brief depressive disorder, intractable depression/chronic depression, double depression, acute renal failure.

BEST MODE FOR CARRYING OUT THE INVENTION

Hereinafter, the present invention is described in more detail with reference to Reference Examples, Examples and Pharmacological Test Examples.

REFERENCE EXAMPLE 1

N-Cyclohexyl-4-fluoro-2-nitro-N-methylaniline

Potassium carbonate (6.0 g, 43.5 mmol) and N-methylcyclohexylamine (4.6 g, 40.6 mmol) were added to a N-methylpyrolidone (NMP) solution (20 ml) of 2,5-difluoronitrobenzene (5.0 g, 31.4 mmol), and stirred at 100° C. for 3 hours. The reaction mixture was cooled to room temperature, water was added, and the resulting mixture was extracted with ethyl acetate. The organic layer was washed with water, and then dried over anhydrous magnesium sulfate. The resulting dry product was concentrated under reduced pressure to thereby obtain 7.0 g of oily yellow N-cyclohexyl-4-fluoro-2-nitro-N-methylaniline (yield: 89%).

$^1$H-NMR (CDCl$_3$) δppm:
1.12-1.80 (10H, m), 2.67 (3H, s), 3.00-3.09 (1H, m), 7.07-7.20 (2H, m), 7.42-7.47 (1H, m)

The compounds of the following Reference Examples 2 to 5 were prepared in the same manner as in the above Reference Example 1, using corresponding starting materials.

REFERENCE EXAMPLE 2

4-Fluoro-N-(2-methoxyethyl)-N-methyl-2-nitroaniline $^1$H-NMR (CDCl$_3$) δppm:
2.85 (3H, s), 3.25-3.31 (5H, m), 3.52 (2H, t, J=5.6 Hz), 7.16-7.20 (2H, m), 7.43-7.47 (1H, m)

REFERENCE EXAMPLE 3

4-Fluoro-N-isobutyl-N-methyl-2-nitroaniline $^1$H-NMR (CDCl$_3$) δppm:
0.89 (3H, s), 0.91 (3H, s), 1.89-1.98 (1H, m), 2.81 (3H, s), 2.92 (2H, d, J=7.5 Hz), 7.15-7.20 (2H, m), 7.42-7.46 (1H, m)

REFERENCE EXAMPLE 4

4-Fluoro-N-isopropyl-N-methyl-2-nitroaniline $^1$H-NMR (CDCl$_3$) δppm:
1.16 (3H, s), 1.19 (3H, s), 2.67 (3H, s), 3.50-3.61 (1H, m), 7.15-7.20 (2H, m), 7.43-7.46 (1H, m)

REFERENCE EXAMPLE 5

4-Fluoro-N-methyl-2-nitro-N-propylaniline $^1$H-NMR (CDCl$_3$) δppm:
0.84 (3H, t, J=7.5 Hz), 1.51-1.66 (2H, m), 2.77 (3H, s), 3.00 (2H, t, J=7.5 Hz), 7.05-7.20 (2H, m), 7.44 (1H, dd, J=2.75 Hz, J=8.0 Hz)

REFERENCE EXAMPLE 6

4-Fluoro-2-nitro-1-propylsulfanylbenzene

Potassium carbonate (5.0 g, 36.2 mmol) and 1-propanethiol (2.7 g, 35.5 mmol) were added to a N-methylpyrolidone (NMP) solution (15 ml) of 2,5-difluoronitrobenzene (5.0 g, 31.4 mmol), and the mixture obtained was stirred at 90° C. for 2 hours. After the reaction mixture was cooled to room temperature, water (50 ml) was added, and the reaction product was extracted with ethyl acetate (100 ml). The organic layer was washed with water, and then dried over anhydrous magnesium sulfate. The resulting dry product was concentrated under reduced pressure to thereby obtain 6.7 g of powdery yellow 4-fluoro-2-nitro-1-propylsulfanylbenzene (yield: 99%).

$^1$H-NMR (CDCl$_3$) δppm:
1.06 (3H, t, J=7.5 Hz), 1.68-1.83 (2H, m), 2.89 (2H, t, 7.5 Hz), 7.27-7.42 (2H, m), 7.89 (2H, dd, J=2.75 Hz, J=8.5 Hz)

REFERENCE EXAMPLE 7

1-tert-Butoxy-4-fluoro-2-nitrobenzene

A tetrahydrofuran (THF) solution (20 ml) of potassium tert-butoxide (3.55 g, 31.6 mmol) was cooled in an methanol-ice bath, and 4.2 g of 2,5-difluoronitrobenzene (26.4 mmol) was further added. The mixture was heated to room temperature, stirred for 96 hours, and further stirred at 60° C. for 1 hour. Water (2 ml) and 2N-hydrochloric acid (2 ml) were added to the reaction mixture while cooling with an ice water bath, and subsequently water was added. The resulting mixture was extracted with ethyl acetate. The organic layer was concentrated under reduced pressure, and the residue was then purified using silica gel column chromatography (n-hexane:ethyl acetate=19:1). The purified product was concentrated under reduced pressure to thereby obtain 4.5 g of oily orange 1-tert-butoxy-4-fluoro-2-nitrobenzene (yield: 80%).

$^1$H-NMR (CDCl$_3$) δppm:
1.38 (9H, s), 7.18-7.20 (2H, m), 7.47 (1H, d, J=7.1 Hz)

REFERENCE EXAMPLE 8

4-Fluoro-2-nitro-1-propoxybenzene

A N,N-dimethylformamide (DMF) solution (3 ml) of potassium carbonate (3.48 g, 25.2 mmol) and 1-iodopropane (3.95 g, 23.2 mmol) was added to a DMF solution (7 ml) of 4-fluoro-2-nitrophenol (3.3 g, 21.0 mmol). The mixture was stirred at room temperature for 48 hours. Water was added to the reaction mixture, and the resulting mixture was extracted with ethyl acetate. The organic layer was washed with a saturated sodium chloride solution twice, and concentrated under reduced pressure. The residue was purified using silica gel column chromatography (n-hexane:ethyl acetate=9:1). The purified product was concentrated under reduced pressure to thereby obtain 4.03 g of oily yellow 4-fluoro-2-nitro-1-propoxybenzene (yield: 96%).

$^1$H-NMR (CDCl$_3$) δppm:
1.06 (3H, t, J=7.4 Hz), 1.78-1.92 (2H, m), 4.04 (2H, t, J=6.4 Hz), 7.04 (1H, dd, J=4.3 Hz, J=9.2 Hz), 7.21-7.29 (1H, m), 7.58 (1H, dd, J=3.1 Hz, J=7.8 Hz)

The compounds of the following Reference Examples 9 to 16 were prepared in the same manner as the above Reference Examples 7 to 8, using corresponding starting materials.

REFERENCE EXAMPLE 9

4-Fluoro-1-isopropoxy-2-nitrobenzene $^1$H-NMR (CDCl$_3$) δppm:
1.36 (3H, s), 4.54-4.63 (1H, m), 7.02-7.05 (1H, m), 7.18-7.26 (1H, m), 7.49 (1H, dd, J=3.0 Hz, J=7.5 Hz)

REFERENCE EXAMPLE 10

1-Ethoxy-4-fluoro-2-nitrobenzene $^1$H-NMR (CDCl$_3$) δppm:
1.44 (3H, t, J=7.0 Hz), 4.08 (2H, q, J=7.0 Hz), 7.02 (1H, dd, J=4.25 Hz, J=9.25 Hz), 7.22-7.30 (1H, m), 7.56 (1H, dd, J=3.25 Hz, J=7.75 Hz)

REFERENCE EXAMPLE 11

1-Cyclopropylmethoxy-4-fluoro-2-nitrobenzene $^1$H-NMR (CDCl$_3$) δppm:
0.36-0.41 (2H, m), 0.61-0.69 (2H, m), 1.22-1.28 (1H, m), 3.95 (2H, d, J=6.8 Hz), 7.04 (1H, dd, J=4.4 Hz, J=9.2 Hz), 7.20-7.27 (1H, m), 7.57 (1H, dd, J=3.1 Hz, J=7.8 Hz)

REFERENCE EXAMPLE 12

4-Fluoro-2-nitro-1-(4,4,4-trifluorobutoxy)benzene $^1$H-NMR (CDCl$_3$) δppm:
2.04-2.16 (2H, m), 2.31-2.44 (2H, m), 4.14 (2H, t, J=5.9 Hz), 7.04 (1H, dd, J=4.3 Hz, J=9.2 Hz), 7.24-7.32 (1H, m), 7.61 (1H, dd, J=3.2 Hz, J=7.8 Hz)

REFERENCE EXAMPLE 13

4-Fluoro-1-(2-methoxyethoxy)-2-nitrobenzene $^1$H-NMR (CDCl$_3$) δppm:
3.45 (3H, s), 3.78 (2H, t, J=4.8 Hz), 4.24 (2H, t, J=4.8 Hz), 7.12 (1H, dd, J=4.4 Hz, J=9.2 Hz), 7.23-7.30 (1H, m), 7.59 (1H, dd, J=3.1 Hz, J=7.8 Hz)

REFERENCE EXAMPLE 14

1-Cyclopentyloxy-4-fluoro-2-nitrobenzene $^1$H-NMR (CDCl$_3$) δppm:
1.62-1.66 (2H, m), 1.83-1.94 (6H, m), 4.82-4.86 (1H, m), 7.04 (1H, dd, J=4.4 Hz, J=9.3 Hz), 7.19-7.27 (1H, m), 7.54 (1H, dd, J=3.2 Hz, J=7.8 Hz)

REFERENCE EXAMPLE 15

1-Cyclobutylmethoxy-4-fluoro-2-nitrobenzene $^1$H-NMR (CDCl$_3$) δppm:
1.90-2.02 (4H, m), 2.08-2.15 (2H, m), 2.77-2.81 (1H, m), 4.03 (2H, d, J=6.2 Hz), 7.04 (1H, dd, J=4.3 Hz, J=9.2 Hz), 7.21-7.28 (1H, m), 7.58 (1H, dd, J=3.1 Hz, J=7.8 Hz)

REFERENCE EXAMPLE 16

2-(4-Fluoro-2-nitrophenoxymethyl)tetrahydrofuran $^1$H-NMR (CDCl$_3$) δppm:
1.88-2.12 (4H, m), 3.80-3.94 (2H, m), 4.11 (2H, d, J=4.0 Hz), 4.27-4.32 (1H, m), 7.10 (1H, dd, J=4.4 Hz, J=9.3 Hz), 7.22-7.30 (1H, m), 7.59 (1H, dd, J=3.1 Hz, J=7.8 Hz)

REFERENCE EXAMPLE 17

2-[3-(4-Fluoro-2-nitrophenoxy)propyl]isoindole-1,3-dione

Potassium carbonate (10.8 g, 78.1 mmol) and N-(3-bromopropyl)phthalimide (12.1 g, 45.1 mmol) were added to a N,N-dimethylformamide (DMF) solution (80 ml) of 4-fluoro-2-nitrophenol (6.0 g, 38.2 mmol), and the mixture was stirred at 60° C. for 4 hours. After the reaction mixture was cooled to room temperature, water (200 ml) was added, and the reaction mixture was then cooled with ice. The precipitated insoluble matter was collected by filtration. After being washed with water (50 ml×3), the substance remaining in the filter was air-dried, giving 13.2 g of powdery pale yellow 2-[3-(4-fluoro-2-nitrophenoxy)propyl]isoindole-1,3-dione (yield: 100%).

$^1$H-NMR (CDCl$_3$) δppm:
2.18-2.28 (2H, m), 3.93 (2H, t, J=6.5 Hz), 4.15 (2H, t, J=6.0 Hz), 7.04 (1H, dd, J=4.3 Hz, J=9.2 Hz), 7.23-7.28 (1H, m), 7.58 (1H, dd, J=3.1 Hz, J=7.8 Hz), 7.69-7.74 (2H, m), 7.81-7.85 (2H, m)

REFERENCE EXAMPLE 18

3-(4-Fluoro-2-nitrophenoxy)propylamine 6.5 g of 2-[3-(4-fluoro-2-nitrophenoxy)propyl]isoindole-1,3-dione was suspended in ethanol (140 ml), and hydrazine hydrate (3.0 ml) was added to the resulting suspension. The mixture was stirred for 3.5 hours while heating under reflux. The reaction mixture was cooled to room temperature, and concentrated under reduced pressure. 13 ml of 5N sodium hydroxide aqueous solution was added to the residue, and the resulting mixture was extracted with dichloromethane. The organic layer was washed with a saturated sodium chloride solution, and then dried over anhydrous magnesium sulfate. The resulting dry product was concentrated under reduced pressure to thereby obtain 4.03 g of oily red orange 3-(4-fluoro-2-nitrophenoxy)propylamine (yield: 100%).

$^1$H-NMR (CDCl$_3$) δppm:
1.92-2.02 (2H, m), 2.94 (2H, t, J=6.5 Hz), 4.19 (2H, t, J=5.9 Hz), 7.07 (1H, dd, J=4.3 Hz, J=9.2 Hz), 7.22-7.30 (1H, m), 7.59 (1H, dd, J=3.1 Hz, J=7.8 Hz)

REFERENCE EXAMPLE 19

N-[3-(4-Fluoro-2-nitrophenoxy)propyl]acetamide

Pyridine (1.5 ml, 18.6 mmol) and acetic anhydride (0.97 g, 10.3 mmol) were added to a dichloromethane solution of 3-(4-fluoro-2-nitrophenoxy)propylamine (2.0 g, 9.33 mmol), while being cooled with ice, and then dichloromethane (4 ml) was further added. The resulting mixture was stirred at room temperature for 15 hours. 2N-hydrochloric acid (9.5 ml) was added to the reaction mixture, and the mixture was stirred. Water was added to the mixture, and the resulting mixture was extracted with dichloromethane. After being washed with a saturated sodium chloride aqueous solution, the organic layer was concentrated under reduced pressure. The residue was then purified by silica gel column chromatography (dichloromethane:methanol=30:1→20:1). The purified product was concentrated under reduced pressure to thereby obtain 2.13 g of oily yellow N-[3-(4-fluoro-2-nitrophenoxy)propyl]acetamide (yield: 89%).

$^1$H-NMR (CDCl$_3$) δppm:
2.04 (3H, s), 2.03-2.12 (2H, m), 3.48-3.55 (2H, m), 4.20 (2H, t, J=5.5 Hz), 6.56 (1H, brs), 7.08 (1H, dd, J=4.3 Hz, J=9.3 Hz), 7.26-7.36 (1H, m), 7.70 (1H, dd, J=3.2 Hz, J=7.8 Hz)

REFERENCE EXAMPLE 20

N-[3-(4-Fluoro-2-nitrophenoxy)propyl]methanesulfonamide

Pyridine (1.5 ml, 18.6 mmol) and methanesulfonyl chloride (0.8 ml, 10.3 mmol) were added, while being cooled with ice, to a dichloromethane solution of 3-(4-fluoro-2-nitrophenoxy)propylamine (2.0 g, 9.33 mmol), and dichloromethane (4 ml) was further added. The resulting mixture was stirred at room temperature for 24 hours, and methanesulfonyl chloride (0.12 ml, 1.5 mmol) was further added thereto, and then the mixture was stirred at room temperature for 15 hours. 2N hydrochloric acid (9.5 ml) was added to the reaction mixture, and the mixture was stirred. Water was added to the mixture, and the resulting mixture was extracted with dichloromethane. After being washed with a saturated sodium chloride aqueous solution, the organic layer was concentrated under reduced pressure, and the residue was then purified by silica gel column chromatography (n-hexane:ethyl acetate=4:1→1:1). The purified product was concentrated under reduced pressure to thereby obtain 1.2 g of oily yellow orange N-[3-(4-fluoro-2-nitrophenoxy)propyl]methansulfonamide (yield: 44%).

$^1$H-NMR (CDCl$_3$) δppm:
2.09-2.18 (2H, m), 3.00 (3H, s), 3.39-3.46 (2H, m), 4.23 (2H, t, J=5.6 Hz), 5.00 (1H, brs), 7.09 (1H, dd, J=4.3 Hz, J=9.2 Hz), 7.26-7.35 (1H, m), 7.66 (1H, dd, J=3.1 Hz, J=7.8 Hz)

REFERENCE EXAMPLE 21

Phenyl [3-(4-Fluoro-2-nitrophenoxy)propyl]carbamate

Triethylamine (2.90 ml, 21.4 mmol) and phenyl chlorocarbonate (2.52 ml, 20.0 mmol) were added to a dioxane solution (43 ml) of 3-(4-fluoro-2-nitrophenoxy)propylamine (4.03 g, 18.8 mmol), while being cooled with ice, and the mixture was stirred at room temperature for 0.5 hours. The reaction mixture was concentrated under reduced pressure, and the residue was then purified by silica gel column chromatography (dichloromethane:ethyl acetate=30:1). The purified product was concentrated to dryness under reduced pressure to thereby obtain 5.92 g of powdery yellow phenyl [3-(4-fluoro-2-nitrophenoxy)propyl]carbamate (yield: 94%).
$^1$H-NMR (CDCl$_3$) δppm:
2.09-2.18 (2H, m), 3.48-3.56 (2H, m), 4.21 (2H, t, J=5.7 Hz), 5.69 (1H, brs), 7.05-7.20 (4H, m), 7.26-7.37 (3H, m), 7.65 (1H, dd, J=3.1 Hz, J=7.8 Hz)

REFERENCE EXAMPLE 22

3-[3-(4-Fluoro-2-nitrophenoxy)propyl]-1,1-dimethyl urea

A 50% dimethylamine aqueous solution (2.5 ml) was added to a DMF solution (25 ml) of phenyl [3-(4-fluoro-2-nitrophenoxy)propyl]carbamate (5.89 g, 17.6 mmol), and the mixture was stirred at room temperature for 24 hours. Water was added to the reaction mixture, and the resulting mixture was extracted with ethyl acetate. The organic layer was washed with a saturated sodium chloride aqueous solution twice, and concentrated under reduced pressure. The residue was then purified by silica gel column chromatography (dichloromethane:ethyl acetate=19:1→4:1→2:1). The purified product was concentrated to dryness under reduced pressure to thereby obtain 4.10 g of oily pale yellow 3-[3-(4-fluoro-2-nitrophenoxy)propyl]-1-dimethyl urea (yield: 82%).
$^1$H-NMR (CDCl$_3$) δppm:
2.03-2.12 (2H, m), 2.89 (6H, s), 3.42-3.49 (2H, m), 4.17 (2H, t, J=5.8 Hz), 4.85 (1H, brs), 7.09 (1H, dd, J=4.3 Hz, J=9.3 Hz), 7.24-7.32 (1H, m), 7.61 (1H, dd, J=3.2 Hz, J=7.8 Hz)

REFERENCE EXAMPLE 23

1-[3-(4-Fluoro-2-nitrophenoxy)propyl]-1,3,3-trimethylurea

Sodium hydride (55% in oil) (396 mg, 9.1 mmol) was added, while being cooled with ice, to a DMF solution (9 ml) of 2.0 g of 3-[3-(4-fluoro-2-nitrophenoxy)propyl]-1,1-dimethyl urea (7.0 mmol) and the mixture was stirred at room temperature for 5 minutes. Methyl iodide (0.735 ml, 11.8 mmol) was added to the mixture and the resulting mixture was stirred at room temperature for 48 hours. Water was added to the reaction mixture and extraction with ethyl acetate was performed. After being washed with a saturated sodium chloride aqueous solution, the organic layer was concentrated under reduced pressure. The residue was purified by silica gel column chromatography (dichloromethane:ethyl acetate=9:1→6:1). The purified product was concentrated under reduced pressure to thereby obtain 0.83 g of oily pale yellow 1-[3-(4-fluoro-2-nitrophenoxy)propyl]-1,3,3-trimethylurea (yield: 40%).
$^1$H-NMR (CDCl$_3$) δppm:
2.04-2.14 (2H, m), 2.76 (6H, s), 2.83 (3H, s), 3.38 (2H, t, J=6.9 Hz), 4.09 (2H, t, J=5.9 Hz), 7.04 (1H, dd, J=4.3 Hz, J=9.3 Hz), 7.22-7.30 (1H, m), 7.60 (1H, dd, J=3.1 Hz, J=7.7 Hz)

REFERENCE EXAMPLE 24

5-Fluoro-2-propoxyaniline

4-Fluoro-2-nitro-1-propoxybenzene (2.0 g, 10.0 mmol) and 5% palladium carbon (750 mg) were added to ethanol (30 ml). Catalytic reduction was conducted at room temperature and atmospheric pressure (normal pressure). The catalyst was removed by celite filtration, and the filtrate was concentrated under reduced pressure. The residue was dissolved in dichloromethane, and dried over anhydrous magnesium sulfate. The resulting dry product was concentrated under reduced pressure to thereby obtain 1.45 g of oily red orange 5-fluoro-2-propoxyaniline (yield: 86%).
$^1$H-NMR (CDCl$_3$) δppm:
1.04 (3H, t, J=7.4 Hz), 1.74-1.88 (2H, m), 3.89 (2H, brs), 3.90 (2H, t, J=6.5 Hz), 6.31-6.46 (2H, m), 6.66 (1H, dd, J=5.1 Hz, J=8.7 Hz)

The compounds of the following Reference Examples 25 to were prepared in the same manner as the above Reference Example 24, using corresponding starting materials.

REFERENCE EXAMPLE 25

5-Fluoro-2-isopropoxyaniline $^1$H-NMR (CDCl$_3$) δppm:
1.32 (3H, s), 1.35 (3H, s), 3.88 (2H, brs), 4.38-4.48 (1H, m), 6.31-6.46 (2H, m), 6.68-6.73 (1H, m)

REFERENCE EXAMPLE 26

2-Ethoxy-5-fluoroaniline $^1$H-NMR (CDCl$_3$) δppm:
1.39 (3H, t, J=7.0 Hz), 3.90 (2H, brs), 3.97 (2H, q, J=7.0 Hz), 6.31-6.46 (2H, m), 6.63-6.68 (1H, m)

REFERENCE EXAMPLE 27

5-Fluoro-2-morpholin-4-ylaniline $^1$H-NMR (CDCl$_3$) δppm:
2.83 (4H, t, J=4.6 Hz), 3.81 (4H, t, J=4.6 Hz), 4.13 (2H, brs), 6.38-6.45 (2H, m), 6.93-6.97 (1H, m)

REFERENCE EXAMPLE 28

5-Fluoro-2-pyrrolidin-1-ylaniline $^1$H-NMR (CDCl$_3$) δppm:
1.88-1.94 (4H, m), 2.94-3.00 (4H, m), 4.03 (2H, brs), 6.35-6.46 (2H, m), 6.90-6.95 (1H, m)

REFERENCE EXAMPLE 29

2-Cyclopropylmethoxy-5-fluoroaniline $^1$H-NMR (CDCl$_3$) δppm:
0.29-0.35 (2H, m), 0.58-0.65 (2H, m), 1.22-1.29 (1H, m), 3.77 (2H, d, J=6.9 Hz), 3.94 (2H, brs), 6.29-6.46 (2H, m), 6.64 (1H, dd, J=5.1 Hz, J=8.8 Hz)

REFERENCE EXAMPLE 30

N$^1$-Cyclohexyl-4-fluoro-N$^1$-methylbenzene-1,2-diamine $^1$H-NMR (CDCl$_3$) δppm:
1.11-1.31 (4H, m), 1.55-1.82 (6H, m), 2.57-2.68 (4H, m), 4.18 (2H, brs), 6.33-6.44 (2H, m), 6.92-6.98 (1H, m)

REFERENCE EXAMPLE 31

4-Fluoro-N$^1$-(2-methoxyethyl)-N$^1$-methylbenzene-1,2-diamine $^1$H-NMR (CDCl$_3$) δppm:
2.70 (3H, s), 2.96 (2H, t, J=5.4 Hz), 3.39 (3H, s), 3.45 (2H, t, J=5.4 Hz), 4.38 (2H, brs), 6.33-6.43 (2H, m), 6.93-6.99 (1H, m)

REFERENCE EXAMPLE 32

4-Fluoro-N$^1$-isobutyl-N$^1$-methylbenzene-1,2-diamine $^1$H-NMR (CDCl$_3$) δppm:
0.92 (3H, s), 0.94 (3H, s), 1.62-1.83 (1H, m), 2.54-2.60 (5H, m), 6.30-6.49 (2H, m), 6.82-6.93 (1H, m)

REFERENCE EXAMPLE 33

4-Fluoro-N$^1$-isopropyl-N$^1$-methylbenzene-1,2-diamine $^1$H-NMR (CDCl$_3$) δppm:
1.05 (3H, s), 1.07 (3H, s), 2.55 (3H, s), 3.06-3.17 (1H, m), 4.16 (2H, brs), 6.34-6.45 (2H, m), 6.91-6.97 (1H, m)

REFERENCE EXAMPLE 34

4-Fluoro-N$^1$-methyl-N$^1$-propylbenzene-1,2-diamine $^1$H-NMR (CDCl$_3$) δppm: 0.86 (3H, t, J=7.4 Hz), 1.41-1.56 (2H, m), 2.57 (3H, s), 2.72 (2H, t, J=7.25 Hz), 4.18 (2H, brs), 6.35-6.44 (2H, m), 6.91-6.97 (1H, m)

REFERENCE EXAMPLE 35

N-[3-(2-Amino-4-fluorophenoxy)propyl]acetamide $^1$H-NMR (CDCl$_3$) δppm:
1.95-2.05 (2H, m), 1.97 (3H, s), 3.42-3.50 (2H, m), 3.92 (2H, brs), 4.02 (2H, t, J=5.9 Hz), 5.83 (1H, brs), 6.32-6.47 (2H, m), 6.68 (1H, dd, J=5.0 Hz, J=8.8 Hz)

REFERENCE EXAMPLE 36

N-[3-(2-Amino-4-fluorophenoxy)propyl]methanesulfonamide $^1$H-NMR (CDCl$_3$) δppm:
2.02-2.11 (2H, m), 2.94 (3H, s), 3.33-3.40 (2H, m), 3.91 (2H, brs), 4.07 (2H, t, J=5.7 Hz), 4.76 (1H, brs), 6.32-6.46 (2H, m), 6.68 (1H, dd, J=5.0 Hz, J=8.8 Hz)

REFERENCE EXAMPLE 37

5-Fluoro-2-(4,4,4-trifluorobutoxy)aniline $^1$H-NMR (CDCl$_3$) δppm:
2.01-2.12 (2H, m), 2.22-2.41 (2H, m), 3.87 (2H, brs), 4.01 (2H, t, J=6.0 Hz), 6.32-6.47 (2H, m), 6.65 (1H, dd, J=5.0 Hz, J=8.8 Hz)

REFERENCE EXAMPLE 38

1-[3-(2-Amino-4-fluorophenoxy)propyl]-1,3,3-trimethylurea $^1$H-NMR (CDCl$_3$) δppm:
1.99-2.10 (2H, m), 2.78 (6H, s), 2.84 (3H, s), 3.37 (2H, t, J=6.9 Hz), 3.94 (2H, brs), 3.97 (2H, t, J=6.1 Hz), 6.30-6.45 (2H, m), 6.65 (1H, dd, J=5.1 Hz, J=8.8 Hz)

REFERENCE EXAMPLE 39

5-Fluoro-2-(2-methoxyethoxy)aniline $^1$H-NMR (CDCl$_3$) δppm:
3.43 (3H, s), 3.70-3.73 (2H, m), 3.99 (2H, brs), 4.07-4.10 (2H, m), 6.30-6.45 (2H, m), 6.72 (1H, dd, J=5.1 Hz, J=8.7 Hz)

REFERENCE EXAMPLE 40

2-Cyclopentyloxy-5-fluoroaniline $^1$H-NMR (CDCl$_3$) δppm:
1.56-1.66 (2H, m), 1.75-1.87 (6H, m), 3.85 (2H, brs), 4.69-4.72 (1H, m), 6.30-6.45 (2H, m), 6.66 (1H, dd, J=5.1 Hz, J=8.8 Hz)

REFERENCE EXAMPLE 41

2-Cyclobutylmethoxy-5-fluoroaniline $^1$H-NMR (CDCl$_3$) δppm:
1.86-1.96 (4H, m), 2.08-2.16 (2H, m), 2.74-2.80 (1H, m), 3.90 (2H, brs), 3.91 (2H, d, J=6.7 Hz), 6.31-6.45 (2H, m), 6.66 (1H, dd, J=5.1 Hz, J=8.8 Hz)

REFERENCE EXAMPLE 42

2-tert-Butoxy-5-fluoroaniline $^1$H-NMR (CDCl$_3$) δppm:
1.37 (9H, s), 3.87 (2H, brs), 6.27-6.45 (2H, m), 6.85 (1H, dd, J=5.6 Hz, J=8.8 Hz)

REFERENCE EXAMPLE 43

5-Fluoro-2-propylsulfanylaniline

4-Fluoro-2-nitro-1-propylsulfanylbenzene (6.7 g, 31.1 mmol) was dissolved in a mixed solvent of ethanol (40 ml) and water (4 ml). Ammonium chloride (17 g, 0.32 mol) was added to the resulting mixture, and zinc powder (20 g, 0.31 mol) were added little by little. The resulting mixture was then stirred at room temperature for 1 hour. Insoluble matter was removed by filtration, and the filtrate was concentrated under reduced pressure to thereby obtain 5.8 g of oily brown 5-fluoro-2-propylsulfanylaniline (yield: 93%).

$^1$H-NMR (CDCl$_3$) δppm:
0.96 (3H, t, J=7.3 Hz), 1.49-1.64 (2H, m), 2.62 (2H, t, J=7.4 Hz), 4.51 (2H, brs), 6.35-6.47 (2H, m), 7.32-7.38 (1H, m)

REFERENCE EXAMPLE 44

4,5-Difluoro-2-propoxyaniline

A toluene solution (20 ml) of benzophenone imine (2.38 g, 13.1 mmol), tris(dibenzylidene acetone)dipalladium (275 mg, 0.3 mmol), 9,9-dimethyl-4,5-bis(diphenylphosphino)xanthene (XANTPHOS) (347 mg, 0.6 mmol) and cesium carbonate (5.83 g, 17.9 mmol) were added to a toluene solution (60 ml) of 1-bromo-4,5-difluoro-2-propoxybenzene (3.0 g, 11.9 mmol). The mixture was stirred under a nitrogen atmosphere at 100° C. for 23 hours. After the reaction mixture was cooled to room temperature, water and a saturated ammonium chloride aqueous solution were added. The resulting mixture was extracted with ethyl acetate. The organic layer was dried over anhydrous magnesium sulfate, and then concentrated under reduced pressure. The residue was dissolved with diethyl ether (60 ml), and concentrated hydrochloric acid (10 ml) was added to the resulting solution, which was then stirred for 2 hours. A 5N sodium hydroxide aqueous solution (24 ml) was added to the reaction mixture to get a pH=11, and concentrated under reduced pressure. The residue was dissolved in dichloromethane and washed with a saturated sodium chloride aqueous solution. The organic layer was concentrated under reduced pressure. The residue was then purified by silica gel column chromatography (n-hexane:ethyl acetate=9:1). The purified product was concentrated under reduced pressure to thereby obtain 850 mg of oily dark brown 4,5-difluoro-2-propoxyaniline (yield: 38%).

$^1$H-NMR (CDCl$_3$) δppm:
1.04 (3H, t, J=7.4 Hz), 1.75-1.86 (2H, m), 3.71 (2H, brs), 3.88 (2H, t, J=6.5 Hz), 6.51 (1H, dd, J=8.0 Hz, 11.5 Hz), 6.60 (1H, dd, J=7.3 Hz, J=11.8 Hz)

REFERENCE EXAMPLE 45

1-(2-Amino-4-fluorobenzoyl)pyrrolidine

A DMF solution (4 ml) of pyrrolidine (1.93 g, 27.1 mmol), a DMF solution (4 ml) of triethylamine (3.79 g, 37.5 mmol), 1-hydroxybenzotriazole (HOBt) (3.11 g, 23.0 mmol), and 1-(3-dimethylaminopropyl)-3-ethylcarbodiimide hydrochloride (WSC) (3.91 g, 20.4 mmol) were added to a DMF solution (4 ml) of 4-fluoroanthranilic acid (2.0 g, 12.8 mmol) in that order. The mixture was stirred at room temperature for 14 hours. Water was added to the reaction mixture and the resulting mixture was extracted with ethyl acetate. The organic layer was washed with a saturated sodium chloride aqueous solution, and then concentrated under reduced pressure. The residue was then purified by silica gel column chromatography (dichloromethane:methanol=30:1). The purified product was concentrated under reduced pressure to thereby obtain 1.65 g of oily orange 1-(2-amino-4-fluorobenzoyl)pyrrolidine (yield: 62%).

$^1$H-NMR (CDCl$_3$) δppm:
1.75-2.00 (4H, m), 3.40-3.75 (4H, m), 4.85 (2H, brs), 6.33-6.40 (2H, m), 7.14-7.21 (1H, m)

REFERENCE EXAMPLE 46

Ethyl α-(hydroxymethylene)-4-methoxyphenyl acetate

Sodium hydride (60% in oil) (467 mg, 11.7 mmol) was added to a benzene solution (10 ml) of ethyl 4-methoxyphenyl acetate (2.0 g, 10.3 mmol), while being cooled with ice. The mixture was stirred at room temperature for 5 minutes. The stirred mixture was cooled with ice again; ethyl formate (1.02 ml, 12.6 mmol) was added thereto, and stirred at room temperature for 3 hours. While being cooled with ice, water and ethyl acetate were added to the reaction mixture, and then 2N hydrochloric acid (6 ml) was added to separate the reaction mixture into two layers. The organic layer was concentrated under reduced pressure, and the residue was then purified by silica gel column chromatography (n-hexane:ethyl acetate=4:1). The purified product was concentrated under reduced pressure to thereby obtain 1.97 g of oily slightly reddish-brown ethyl α-(hydroxymethylene)-4-methoxyphenyl acetate (yield: 86%). The resultant compound undergoes nitrogen substitution, and was stored in a freezer.

$^1$H-NMR (CDCl$_3$) δppm:
1.28 (3H, t, J=7.1 Hz), 3.81 (3H, s), 4.28 (2H, q, J=7.1 Hz), 6.87 (2H, d, J=8.8 Hz), 7.16-7.26 (3H, m), 12.02 (1H, d, J=12.5 Hz)

The compounds of the following Reference Examples 47 to 57 were prepared in the same manner as the above Reference Example 46, using corresponding starting materials.

REFERENCE EXAMPLE 47

Ethyl 2,4-dimethoxy-α-(hydroxymethylene)phenyl acetate $^1$H-NMR (CDCl$_3$) δppm:
1.21 (3H, t, J=7.1 Hz), 3.76 (3H, s), 3.81 (3H, s), 4.22 (2H, q, J=7.1 Hz), 6.43-6.49 (2H, m), 7.00 (1H, d, J=8.9 Hz), 7.12 (1H, d, J=12.6 Hz), 11.89 (1H, d, J=12.6 Hz)

REFERENCE EXAMPLE 48

Ethyl 2,4-dichloro-α-(hydroxymethylene)phenyl acetate $^1$H-NMR (CDCl$_3$) δppm:
1.15 (3H, t, J=7.2 Hz), 4.22 (2H, q, J=7.2 Hz), 7.11-7.26 (3H, m), 7.40-7.43 (1H, m), 12.00 (1H, d, J=12.2 Hz)

REFERENCE EXAMPLE 49

Ethyl α-(hydroxymethylene)-2-methoxyphenyl acetate $^1$H-NMR (CDCl$_3$) δppm:
1.19 (3H, t, J=7.1 Hz), 3.79 (3H, s), 4.21 (2H, q, J=7.1 Hz), 6.86-7.68 (5H, m), 11.91 (1H, d, J=12.3 Hz)

REFERENCE EXAMPLE 50

Ethyl α-(hydroxymethylene)-2-isopropoxy-4-methoxyphenyl acetate $^1$H-NMR (CDCl$_3$) δppm:
1.20-1.31 (9H, m), 3.80 (3H, s), 4.17 (2H, q, J=7.1 Hz), 4.43-4.47 (1H, m), 6.42-6.46 (2H, m), 6.90-7.12 (2H, m), 11.85 (1H, d, J=12.6 Hz)

REFERENCE EXAMPLE 51

Ethyl α-(hydroxymethylene)-4-methoxy-2-methylphenyl acetate $^1$H-NMR (CDCl$_3$) δppm:
1.20 (3H, t, J=7.2 Hz), 2.19 (3H, s), 3.80 (3H, s), 4.22 (2H, q, J=7.2 Hz), 6.54-6.75 (2H, m), 7.02-7.26 (2H, m), 11.94 (1H, d, J=12.7 Hz)

REFERENCE EXAMPLE 52

Ethyl 2-fluoro-α-(hydroxymethylene)-4-methoxyphenyl acetate $^1$H-NMR (CDCl$_3$) δppm:
1.22 (3H, t, J=7.1 Hz), 3.80 (3H, s), 4.21 (2H, q, J=7.1 Hz), 6.61-6.69 (2H, m), 7.03-7.26 (2H, m), 12.05 (1H, d, J=12.3 Hz)

REFERENCE EXAMPLE 53

Ethyl 4-ethoxy-α-(hydroxymethylene)-2-methoxyphenyl acetate

¹H-NMR (CDCl₃) δppm:
1.19-1.45 (6H, m), 3.75 (3H, s), 4.00-4.26 (4H, m), 6.42-6.48 (2H, m), 6.97-7.26 (2H, m), 11.86 (1H, d, J=12.3 Hz)

REFERENCE EXAMPLE 54

Ethyl α-(hydroxymethylene)-4-isopropoxy-2-methoxyphenyl acetate

¹H-NMR (CDCl₃) δppm:
1.20-1.31 (9H, m), 3.75 (3H, s), 4.16 (2H, q, J=7.2 Hz), 4.43-4.47 (1H, m), 6.43-6.48 (2H, m), 6.99-7.22 (2H, m), 11.87 (1H, d, J=12.3 Hz)

REFERENCE EXAMPLE 55

Ethyl 4-cyclopropylmethoxy-α-(hydroxymethylene)phenyl acetate

¹H-NMR (CDCl₃) δppm:
0.35-0.37 (4H, m), 1.24 (3H, t, J=7.1 Hz), 3.81-3.83 (2H, m), 4.25 (2H, q, J=7.1 Hz), 6.85-6.91 (2H, m), 7.16-7.27 (3H, m), 12.02 (1H, d, J=12.5 Hz)

REFERENCE EXAMPLE 56

Ethyl α-(hydroxymethylene)-4-methylsulfanylphenyl acetate

¹H-NMR (CDCl₃) δppm:
1.22 (3H, t, J=7.1 Hz), 2.47 (3H, s), 4.09 (2H, q, J=7.1 Hz), 6.85-6.94 (2H, m), 7.16-7.26 (3H, m), 11.99 (1H, d, J=12.3 Hz)

REFERENCE EXAMPLE 57

Ethyl 4-ethoxy-α-(hydroxymethylene)phenyl acetate

¹H-NMR (CDCl₃) δppm:
1.23-1.47 (6H, m), 4.00-4.32 (4H, m), 6.85-6.88 (2H, m), 7.15-7.27 (3H, m), 12.00 (1H, d, J=12.5 Hz)

REFERENCE EXAMPLE 58

Ethyl 4-methoxy-α-propionylphenyl acetate

L-Proline (980 mg, 8.52 mmol), copper (I) iodide (810 mg, 4.26 mmol), and cesium carbonate (27.7 g, 85.2 mmol) were added to a dimethylsulfoxide (DMSO) solution (40 ml) of ethyl propionyl acetate (3.8 g, 26.3 mmol) and 4-iodoanisole (5.0 g, 21.3 mmol) in that order. The mixture was stirred under a nitrogen atmosphere at 40 to 45° C. for 27 hours. The reaction mixture was cooled to room temperature, and then water and ammonium chloride aqueous solution were added. The resulting mixture was extracted with ethyl acetate. The organic layer was washed with a saturated sodium chloride aqueous solution twice, and concentrated under reduced pressure. The residue was then purified by silica gel column chromatography (n-hexane:ethyl acetate=19:1→8:1). The purified product was concentrated under reduced pressure to thereby obtain 2.97 g of oily yellow ethyl 4-methoxy-α-propionylphenyl acetate (yield: 56%).

¹H-NMR (CDCl₃) δppm:
1.01-1.11 (3H, m), 1.18-1.31 (3H, m), 2.52-2.61 (2H, m), 3.80 and 3.82 (3H, s), 4.15-4.24 (2H, m), 4.65 (0.6H, s), 6.84-7.28 (4H, m), 13.13 (0.4H, s)

The compound of the following Reference Example 59 was prepared in the same manner as the above Reference Example 58, using corresponding starting materials.

REFERENCE EXAMPLE 59

Ethyl α-acetyl-4-methoxyphenyl acetate

¹H-NMR (CDCl₃) δppm:
1.16-1.29 (3H, m), 1.85 (1.4H, s), 2.17 (1.6H, s), 3.80 and 3.82 (1.4 and 1.6H, s), 4.13-4.25 (2H, m), 4.62 (0.6H, s), 6.85-7.28 (4H, m), 13.09 (0.4H, s)

REFERENCE EXAMPLE 60

5-[(5-Fluoro-2-propoxyphenylamino)methylene]-2,2-dimethyl-[1,3]dioxane-4,6-dione Meldrum's acid (5.29 g, 36.7 mmol) was added to methyl orthoformate (31 ml), and the mixture was stirred for 2 hours while heating under reflux. The resulting mixture was cooled to 50° C., and 5-fluoro-2-propoxyaniline (4.28 g, 25.3 mmol) and methyl orthoformate (3 ml) were added thereto. The resulting mixture was stirred for 6 hours while heating under reflux. The resulting reaction mixture was then cooled to room temperature, and concentrated under reduced pressure. The residue was recrystallized from methanol to thereby obtain 7.61 g of powdery pale brown 5-[(5-fluoro-2-propoxyphenylamino)methylene]-2,2-dimethyl-[1,3]dioxane-4,6-dione (yield: 93%).

¹H-NMR (CDCl₃) δppm:
1.12 (3H, t, J=7.4 Hz), 1.75 (6H, s), 1.85-1.98 (2H, m), 4.02 (2H, t, J=6.3 Hz), 6.86-6.91 (2H, m), 7.06-7.10 (1H, m), 8.60 (1H, d, J=14.6 Hz), 11.68 (1H, d, J=14.8 Hz)

The compound of the following Reference Example 61 was prepared in the same manner as the above Reference Example 60, using corresponding starting materials.

REFERENCE EXAMPLE 61

5-[(2-Cyclopropylmethoxy-5-fluorophenylamino)methylene]-2,2-dimethyl-[1,3]dioxane-4,6-dione ¹H-NMR (CDCl₃) δppm:
0.39-0.43 (2H, m), 0.65-0.73 (2H, m), 1.31-1.37 (1H, m), 1.75 (6H, s), 3.92 (2H, d, J=6.9 Hz), 6.86-6.91 (2H, m), 7.07-7.11 (1H, m), 8.60 (1H, d, J=14.5 Hz), 11.69 (1H, d, J=14.3 Hz)

REFERENCE EXAMPLE 62

5-Fluoro-8-propoxy-1H-quinolin-4-one

5-[(5-Fluoro-2-propoxyphenylamino)methylene]-2,2-dimethyl-[1,3]dioxane-4,6-dione (7.6 g, 23.5 mmol) was added to diphenyl ether (15 ml), and the mixture was heated using a mantle heater, and then kept under reflux for 2 hours. After the reaction mixture was cooled to room temperature, ethyl acetate (5 ml) and n-hexane (10 ml) were added. The resulting mixture was stirred and the resultant insoluble matter was collected by filtration. The filtrate was recrystallized from an ethyl acetate-n-hexane mixed solvent to thereby obtain 3.15 g of powdery dark brown 5-fluoro-8-propoxy-1H-quinolin-4-one (yield: 61%).

$^1$H-NMR (DMSO-d$_6$) δppm:
1.03 (3H, t, J=7.3 Hz), 1.74-1.88 (2H, m), 4.07 (2H, t, J=6.4 Hz), 5.97 (1H, d, J=7.4 Hz), 6.87 (1H, dd, J=8.8 Hz, 11.9 Hz), 7.13 (1H, dd, J=4.0 Hz, J=8.8 Hz), 7.70 (1H, t, J=7.2 Hz), 11.07 (1H, brs)

The compound of the following Reference Example 63 was prepared in the same manner as the above Reference Example 62, using corresponding starting materials.

REFERENCE EXAMPLE 63

8-Cyclopropylmethoxy-5-fluoro-1H-quinolin-4-one $^1$H-NMR (DMSO-d$_6$) δppm:
0.34-0.40 (2H, m), 0.55-0.61 (2H, m), 1.27-1.33 (1H, m), 3.98 (2H, d, J=7.0 Hz), 5.97 (1H, d, J=7.4 Hz), 6.86 (1H, dd, J=8.8 Hz, J=11.9 Hz), 7.13 (1H, dd, J=4.0 Hz, J=8.8 Hz), 7.71 (1H, t, J=7.4 Hz), 11.10 (1H, brs)

REFERENCE EXAMPLE 64

5-Fluoro-2-methyl-8-propoxy-1H-quinolin-4-one

Amberlyst 15 (1.0 g, a product of Sigma Aldrich Corp.) was added to a benzene solution (200 ml) of 5-fluoro-2-propoxyaniline (10 g, 59 mmol) and ethyl acetoacetate (7.7 g, 59 mmol). The mixture was stirred while heating under reflux for 6 hours and using a Dean-Stark trap. The reaction mixture was cooled to room temperature, the resin was removed by filtration, and the filtrate was concentrated under reduced pressure. Diphenyl ether (20 ml) was added to the residue. The mixture was heated using a mantle heater and stirred under reflux for 2 hours. After the reaction mixture was cooled to room temperature, insoluble matter obtained by the addition of n-hexane-ethyl acetate (2:1) was collected by filtration. The substance remaining on the filter was washed with n-hexane-ethyl acetate (2:1), and dried to thereby obtain 6.0 g of powdery pale yellow 5-fluoro-2-methyl-8-propoxy-1H-quinolin-4-one (yield: 43%).

$^1$H-NMR (DMSO-d$_6$) δppm:
0.97 (3H, t, J=7.3 Hz), 1.77-1.87 (2H, m), 2.34 (3H, s), 4.08 (2H, t, J=6.4 Hz), 5.84 (1H, s), 6.79-6.88 (1H, m), 7.10-7.14 (1H, m), 10.58 (1H, brs)

REFERENCE EXAMPLE 65

5-Fluoro-3-iodo-8-propoxy-1H-quinolin-4-one

5-Fluoro-8-propoxy-1H-quinolin-4-one (1.0 g, 4.52 mmol) was suspended in DMF (11 ml), and potassium carbonate (0.7 g, 5.06 mmol) and iodide (1.27 g, 5.00 mmol) were added to the suspension. The resulting mixture was stirred at room temperature for 3 hours. The reaction mixture was poured into a sodium thiosulfate (3.94 g, 25 mmol) aqueous solution (45 ml). The mixture was stirred for 5 minutes. Ethyl acetate was added to the resulting reaction mixture and stirred, thereby collecting insoluble matter by filtration. The filtrate was separated, and the organic layer was washed with a saturated sodium chloride aqueous solution, and then concentrated under reduced pressure. The residue and the collected insoluble matter were combined, and then purified by silica gel column chromatography (dichloromethane:methanol=50:1→40:1). The purified product was concentrated to dryness under reduced pressure to thereby obtain 1.25 g of powdery pale dark brown 5-fluoro-3-iode-8-propoxy-1H-quinolin-4-one (yield: 80%).

$^1$H-NMR (DMSO-d$_6$) δppm:
1.02 (3H, t, J=7.4 Hz), 1.78-1.86 (2H, m), 4.09 (2H, t, J=6.5 Hz), 6.97 (1H, dd, J=8.8 Hz, J=11.9 Hz), 7.19 (1H, dd, J=4.0 Hz, J=8.8 Hz), 8.19 (1H, s), 11.44 (1H, brs)

The compounds of the following Reference Examples 66 and 67 were prepared in the same manner as the above Reference Example 65, using corresponding starting materials.

REFERENCE EXAMPLE 66

5-Fluoro-3-iodo-2-methyl-8-propoxy-1H-quinolin-4-one $^1$H-NMR (CDCl$_3$) δppm:
0.97 (3H, t, J=7.4 Hz), 1.78-1.88 (2H, m), 2.70 (3H, s), 6.92-7.00 (1H, m), 7.17-7.22 (1H, m)

REFERENCE EXAMPLE 67

8-Cyclopropylmethoxy-5-fluoro-3-iodo-1H-quinolin-4-one $^1$H-NMR (DMSO-d$_6$) δppm:
0.36-0.40 (2H, m), 0.56-0.63 (2H, m), 1.28-1.31 (1H, m), 3.99 (2H, d, J=7.0 Hz), 6.97 (1H, dd, J=8.8 Hz, J=11.9 Hz), 7.19 (1H, dd, J=4.0 Hz, J=8.8 Hz), 8.19 (1H, s), 11.48 (1H, brs)

REFERENCE EXAMPLE 68

8-Cyclopropylmethoxy-1-ethyl-5-fluoro-3-iodo-1H-quinolin-4-one

Potassium carbonate (450 mg, 3.26 mmol) was added to a DMF solution (5 ml) of 8-cyclopropylmethoxy-5-fluoro-3-iodo-1H-quinolin-4-one (910 mg, 2.53 mmol). The mixture was stirred for 15 minutes at room temperature. Ethyl iodide (0.31 ml, 3.87 mmol) was added thereto, and the resulting mixture was stirred at 60° C. for 2 hours. After the reaction mixture was cooled to room temperature, water was added, and the resulting mixture was extracted with ethyl acetate. The organic layer was concentrated under reduced pressure and the residue was then purified by silica gel column chromatography (dichloromethane:ethyl acetate=40:1→15:1). The purified product was concentrated to dryness under reduced pressure to thereby obtain 750 mg of powdery pale dark brown 8-cyclopropylmethoxy-1-ethyl-5-fluoro-3-iodo-1H-quinolin-4-one (yield: 77%).

$^1$H-NMR (DMSO-d$_6$) δppm:
0.34-0.38 (2H, m), 0.57-0.64 (2H, m), 1.26-1.36 (4H, m), 3.93 (2H, d, J=7.3 Hz), 4.56 (2H, q, J=7.0 Hz), 7.05 (1H, dd, J=8.9 Hz, J=11.4 Hz), 7.24 (1H, dd, J=4.6 Hz, J=9.0 Hz), 8.45 (1H, s)

REFERENCE EXAMPLE 69

2,2,2-Trifluoro-N-(5-fluoro-2-propoxyphenyl)acetamide

A dichloromethane solution (60 ml) of 5-fluoro-2-propoxyaniline (10.0 g, 59.1 mmol) was cooled with ice, and triethylamine (16.5 ml) was added thereto. Then, trifluoroacetic anhydride (14.8 g, 70.5 mmol) was added, and the resulting mixture was stirred at room temperature for 1 hour. Water was added to the reaction mixture, and the resulting mixture was extracted with dichloromethane. The organic layer was washed with water, and dried over anhydrous sodium sulfate. The resulting dry product was concentrated under reduced pressure, and the residue was then purified by silica gel column chromatography (n-hexane:ethyl acetate=10:1). The purified product was concentrated to dryness under reduced pressure to thereby obtain 15.83 g of powdery white 2,2,2-trifluoro-N-(5-fluoro-2-propoxyphenyl)acetamide (yield: 99%).

$^1$H-NMR (CDCl$_3$) δppm:
1.03 (3H, t, J=7.5 Hz), 1.79-1.93 (2H, m), 3.98 (2H, t, J=6.5 Hz), 6.80-6.86 (2H, m), 8.10-8.12 (1H, m), 8.64 (1H, brs)

REFERENCE EXAMPLE 70

Ethyl ester of 4,4,4-trifluoro-3-(5-fluoro-2-propoxyphenylamino)buta-2-enoic acid Carboethoxymethylene triphenylphosphorane (41.52 g, 119.2 mmol) was added to a toluene solution (100 ml) of 2,2,2-trifluoro-N-(5-fluoro-2-propoxyphenyl)acetamide (15.83 g, 59.1 mmol). The mixture was stirred under a nitrogen atmosphere while heating under reflux for 4 hours. The reaction mixture was cooled to room temperature, concentrated under reduced pressure, and the residue was then purified by silica gel column chromatography (n-hexane:ethyl acetate=10:1). The purified product was concentrated under reduced pressure to thereby obtain 19.7 g of oily yellow ethyl ester of 4,4,4-trifluoro-3-(5-fluoro-2-propoxyphenylamino)buta-2-enoic acid (yield: 99%).

$^1$H-NMR (CDCl$_3$) δppm:
1.02 (3H, t, J=7.5 Hz), 1.28 (3H, t, 7.0 Hz), 1.74-1.88 (2H, m), 3.85 (2H, t, J=6.5 Hz), 4.17 (2H, q, J=7.0 Hz), 5.41 (1H, s), 6.77-6.97 (3H, m), 9.77 (1H, brs)

REFERENCE EXAMPLE 71

5-Fluoro-8-propoxy-2-trifluoromethyl-1H-quinolin-4-one

Diphenyl ether (15 ml) was added to ethyl ester of 4,4,4-trifluoro-3-(5-fluoro-2-propoxyphenylamino)buta-2-enoic acid (19.7 g, 59.0 mmol), and the mixture was stirred for 1.5 hours while heating under reflux. The reaction mixture was cooled to room temperature, n-hexane was added, and the precipitate was collected by filtration. The substance remaining on the filter was washed with n-hexane, and dried to thereby obtain 16.2 g of powdery white 5-fluoro-8-propoxy-2-trifluoromethyl-1H-quinolin-4-one (yield: 94%).

$^1$H-NMR (DMSO-d$_6$) δppm:
1.00 (3H, t, J=7.5 Hz), 1.76-1.90 (2H, m), 4.07 (2H, t, J=6.5 Hz), 7.18-7.32 (3H, m), 12.26 (1H, brs)

REFERENCE EXAMPLE 72

5-Fluoro-3-iodo-8-propoxy-2-trifluoromethyl-1H-quinolin-4-one

Potassium carbonate (3.73 g, 27 mmol) and iodide (6.85 g, 27 mmol) were added to a DMF solution (20 ml) of 5-fluoro-8-propoxy-2-trifluoromethyl-1H-quinolin-4-one (6.0 g, 20.7 mmol) in that order, and the resulting mixture was stirred at room temperature for 1.5 hours. A saturated sodium sulfite aqueous solution (20 ml) and ethyl acetate were added to the reaction mixture, and the precipitated solid was collected by filtration. The filtrate was washed with water, and then dried over anhydrous sodium sulfate. The dried filtrate was concentrated under reduced pressure. The residue and the substance collected by the advance filtration were combined, and dissolved in ethanol, and then concentrated. The residue was recrystallized from an ethyl acetate-n-hexane mixed solvent to thereby obtain 4.7 g of powdery white 5-fluoro-3-iodo-8-propoxy-2-trifluoromethyl-1H-quinolin-4-one (yield: 55%).

$^1$H-NMR (DMSO-d$_6$) δppm:
0.96 (3H, t, J=7.5 Hz), 1.70-1.80 (2H, m), 3.95 (2H, t, J=6.5 Hz), 6.64-6.85 (2H, m), 12.02 (1H, brs)

REFERENCE EXAMPLE 73

1-(5-Bromo-2-cyclopentyloxyphenyl)ethanone

Potassium carbonate (6.55 g, 47.4 mmol), cyclopentyl bromide (8.25 g, 55.3 mmol) and DMF (5 ml) were added to a DMF solution (10 ml) of 5'-bromo-2'-hydroxyacetophenone (8.5 g, 39.5 mmol), and the resulting mixture was stirred at 60° C. for 4.5 hours. Potassium carbonate (3.0 g, 21.7 mmol) and cyclopentyl bromide (2.0 g, 13.4 mmol) were added to the resultant mixture, and stirred at 60° C. for 9 hours. After the reaction mixture was cooled to room temperature, water was added, and the resulting mixture was extracted with ethyl acetate. The organic layer was washed with a saturated sodium chloride aqueous solution, and then concentrated under reduced pressure. The residue was then purified by silica gel column chromatography (n-hexane:ethyl acetate=9:1). The purified product was concentrated under reduced pressure to thereby obtain 11.3 g of oily pale yellow 1-(5-bromo-2-cyclopentyloxyphenyl)ethanone (yield: 100%).

$^1$H-NMR (CDCl$_3$) δppm:
1.68-1.95 (8H, m), 2.58 (3H, s), 4.83-4.87 (1H, m), 6.83 (1H, d, J=8.9 Hz), 7.49 (1H, dd, J=2.6 Hz, 8.9 Hz), 7.82 (1H, d, J=2.6 Hz)

REFERENCE EXAMPLE 74

1-(5-Bromo-2-cyclopentyloxyphenyl)ethanone oxime 1-(5-Bromo-2-cyclopentyloxyphenyl)ethanone (5.0 g, 17.65 mmol) was dissolved in a mixed solvent of chloroform (18 ml) and methanol (70 ml). Hydroxylamine hydrochloride (1.88 g, 27.0 mmol) and pyridine (4.36 ml, 54.1 mmol) were added to the resulting solution, and the mixture was stirred for 6 hours while heating under reflux. The reaction mixture was cooled to room temperature, and then concentrated under reduced pressure. 2N Hydrochloric acid (13.9 ml) was added to the residue, and the resulting mixture was extracted with dichloromethane. The organic layer was washed with a saturated sodium chloride aqueous solution, dried over magnesium sulfate, and concentrated to dryness under reduced pressure. The residue was washed with n-hexane and dried to thereby obtain 4.6 g of powdery white 1-(5-bromo-2-cyclopentyloxyphenyl)ethanone oxime (yield: 87%).

$^1$H-NMR (CDCl$_3$) δppm:
1.65-1.90 (8H, m), 2.17 (3H, s), 4.72-4.76 (1H, m), 6.76 (1H, d, J=8.4 Hz), 7.35-7.41 (2H, m), 7.99 (1H, brs)

REFERENCE EXAMPLE 75

N-(5-Bromo-2-cyclopentyloxyphenyl)acetamide 1-(5-Bromo-2-cyclopentyloxyphenyl)ethanone oxime (4.56 g, 15.3 mmol) was suspended in acetonitrile (100 ml). Indium (III) chloride (507 mg, 2.29 mmol) was added thereto, and the resultant was heated under reflux for 2 hours under a nitrogen atmosphere. The reaction mixture was cooled to room temperature, and then concentrated under reduced pressure. The residue was extracted with dichloromethane. The organic layer was washed with a saturated sodium chloride aqueous solution, and then concentrated under reduced pressure. The residue was then purified by silica gel column chromatography (n-hexane:ethyl acetate=8:1→4:1). The purified product was concentrated under reduced pressure to thereby obtain 3.41 g of oily pale yellow N-(5-bromo-2-cyclopentyloxyphenyl)acetamide (yield: 75%).

$^1$H-NMR (CDCl$_3$) δppm:
1.67-1.94 (8H, m), 2.18 (3H, s), 4.75-4.81 (1H, m), 6.72 (1H, d, J=8.7 Hz), 7.10 (1H, dd, J=2.3 Hz, 8.7 Hz), 7.67 (1H, brs), 8.55 (1H, d, J=2.3 Hz)

REFERENCE EXAMPLE 76

5-Bromo-2-cyclopentyloxyaniline

Concentrated hydrochloric acid (5.8 ml) was added to an ethanol solution (100 ml) of N-(5-bromo-2-cyclopentyloxyphenyl)acetamide (3.4 g, 11.4 mmol), and the resulting mixture was stirred for 3 hours while heating under reflux. After the reaction mixture was cooled to room temperature, a 5N sodium hydroxide solution (14.2 ml) was added to obtain a pH of 11. The resulting mixture was then extracted with dichloromethane. The organic layer was washed with a saturated sodium chloride aqueous solution, and then concentrated under reduced pressure. The residue was then purified by silica gel column chromatography (n-hexane:ethyl acetate=4:1). The purified product was concentrated under reduced pressure to thereby obtain 2.97 g of oily pale yellow 5-bromo-2-cyclopentyloxyaniline (yield: 100%).

$^1$H-NMR (CDCl$_3$) δppm:
1.62-1.89 (8H, m), 3.80 (2H, brs), 4.71-4.75 (1H, m), 6.61 (1H, d, J=8.4 Hz), 6.75-6.81 (2H, m)

EXAMPLE 1

5-Fluoro-3-furan-3-yl-8-propoxy-1H-quinolin-4-one

5-Fluoro-3-iodo-8-propoxy-1H-quinolin-4-one (780 mg, 2.24 mmol) was suspended in a mixed solvent of toluene (10 ml) and methanol (1.6 ml), and furan-3-boronic acid (752 mg), tetrakis triphenylphosphine palladium (130 mg, 0.11 mmol), and a 2N sodium carbonate aqueous solution (2.25 ml) were added thereto in that order. The mixture was stirred under a nitrogen atmosphere at 110° C. for 20 hours. After the reaction mixture was cooled to room temperature, water was added, and the resulting mixture was extracted with dichloromethane. The organic layer was concentrated under reduced pressure, the residue was then purified by silica gel column chromatography (dichloromethane:methanol=60: 1→50:1). The purified product was concentrated under reduced pressure and was recrystallized from ethanol to thereby obtain 180 mg of powdery pale yellow 5-fluoro-3-furan-3-yl-8-propoxy-1H-quinolin-4-one (yield: 58%). Melting point 214-215° C.

$^1$H-NMR (DMSO-d$_6$) δppm:
1.02 (3H, J=7.3 Hz), 1.78-1.87 (2H, m), 4.09 (2H, t, J=6.4 Hz), 6.87-6.95 (2H, m), 7.13 (1H, dd, J=3.8 Hz, J=8.8 Hz), 7.67 (1H, s), 8.11 (1H, s), 8.51 (1H, s), 11.50 (1H, brs)

The compounds of the following Examples 2 to 5 were prepared in the same manner as the above Example 1, using corresponding starting materials.

EXAMPLE 2

5-Fluoro-3-(3-fluoro-4-methoxyphenyl)-8-propoxy-1H-quinolin-4-one

Gray powder (ethanol)
Melting point 194-195° C.
$^1$H-NMR (DMSO-d$_6$) δppm:
1.03 (3H, t, J=7.3 Hz), 1.79-1.87 (2H, m), 3.84 (3H, s), 4.09 (2H, t, J=6.4 Hz), 6.90 (1H, dd, J=8.7 Hz, J=12.1 Hz), 7.12-7.19 (2H, m), 7.35-7.39 (1H, m), 7.56 (1H, dd, J=2.0 Hz, J=13.5 Hz), 7.87 (1H, s), 11.40 (1H, brs)

EXAMPLE 3

5-Fluoro-8-propoxy-3-thiophen-3-yl-1H-quinolin-4-one

Pale brown powder (ethanol)
Melting point 208-210° C.
$^1$H-NMR (DMSO-d$_6$) δppm:
1.02 (3H, t, J=7.4 Hz), 1.75-1.89 (2H, m), 4.08 (2H, t, J=6.4 Hz), 6.90 (1H, dd, J=8.7 Hz, J=12.1 Hz), 7.13 (1H, dd, J=3.9 Hz, J=8.8 Hz), 7.50-7.57 (2H, m), 8.14 (1H, s), 8.19-8.21 (1H, m), 11.42 (1H, brs)

EXAMPLE 4

3-(3-Chloro-4-methoxyphenyl)-5-fluoro-8-propoxy-1H-quinolin-4-one

Pale yellow powder (ethanol)
Melting point 217-218° C.
$^1$H-NMR (DMSO-d$_6$) δppm:
1.02 (3H, t, J=7.3 Hz), 1.78-1.86 (2H, m), 3.85 (3H, s), 4.08 (2H, t, J=6.4 Hz), 6.90 (1H, dd, J=8.8 Hz, J=12.0 Hz), 7.10-7.15 (2H, m), 7.51 (1H, dd, J=2.1 Hz, J=8.5 Hz), 7.74 (1H, d, J=2.1 Hz), 7.87 (1H, s), 11.45 (1H, brs)

EXAMPLE 5

5-Fluoro-8-propoxy-3-(4-trifluoromethoxyphenyl)-1H-quinolin-4-one

Pale gray powder (ethanol)
Melting point 212-214° C.
$^1$H-NMR (DMSO-d$_6$) δppm:
1.03 (3H, t, J=7.3 Hz), 1.79-1.87 (2H, m), 4.09 (2H, t, J=6.4 Hz), 6.92 (1H, dd, J=8.8 Hz, J=12.0 Hz), 7.16 (1H, dd, J=3.9 Hz, J=8.8 Hz), 7.35 (2H, d, J=8.5 Hz), 7.73 (2H, d, J=8.7 Hz), 7.91 (1H, s), 11.45 (1H, brs)

EXAMPLE 6

5-Fluoro-3-(4-methoxyphenyl)-8-propoxy-1H-quinolin-4-one

Amberlyst 15 (1.0 g, a product of Sigma Aldrich Corp.) was added to a benzene solution (150 ml) of 5-fluoro-2-propoxyaniline (16.25 g, 96.0 mmol) and ethyl α-(hydroxymethylene)-4-methoxyphenyl acetate (21.34 g, 96.0 mmol). The mixture was heated under reflux for 14 hours while using a Dean-Stark trap and being stirred. The reaction mixture was cooled to room temperature, the resin was removed by filtration, and the filtrate was concentrated under reduced pressure. Diphenyl ether (40 ml) was added to the residue, and the mixture was heated using a mantle heater and stirred under reflux for 2 hours. The reaction mixture was cooled to room temperature and purified directly by silica gel column chromatography (dichloromethane:methanol=100:0→30:1→20:1). The purified product was concentrated under reduced pressure, and the residue was recrystallized from ethanol to thereby obtain 5.28 g of powdery pale yellow 5-fluoro-3-(4-methoxyphenyl)-8-propoxy-1H-quinolin-4-one (yield: 17%).
Melting point 196-197° C.
$^1$H-NMR (DMSO-$d_6$) δppm:
1.02 (3H, t, J=7.3 Hz), 1.78-1.86 (2H, m), 3.75 (3H, s), 4.07 (2H, t, J=6.4 Hz), 6.83-6.96 (3H, m), 7.11 (1H, dd, J=3.9 Hz, J=8.8 Hz), 7.53 (2H, d, J=8.8 Hz), 7.81 (1H, s), 11.50 (1H, brs)

The compounds of the following Examples 7 to 46 were prepared in the same manner as the above Example 6, using corresponding starting materials.

EXAMPLE 7

5-Fluoro-3-(2-methoxyphenyl)-8-propoxy-1H-quinolin-4-one

White powder (ethyl acetate)
Melting point 193-195° C.
$^1$H-NMR (CDCl$_3$) δppm:
1.05 (3H, t, J=7.5 Hz), 1.82-1.97 (2H, m), 3.77 (3H, s), 4.05 (2H, t, J=6.3 Hz), 6.77-7.02 (4H, m), 7.26-7.29 (1H, m), 7.42-7.45 (1H, m), 7.72-7.74 (1H, m), 8.83 (1H, brs)

EXAMPLE 8

3-(2,4-Dimethoxyphenyl)-5-fluoro-8-propoxy-1H-quinolin-4-one

Pale yellow powder (ethyl acetate)
Melting point 116-118° C.
$^1$H-NMR (CDCl$_3$) δppm:
1.07 (3H, t, J=7.5 Hz), 1.84-1.98 (2H, m), 3.76 (3H, s), 3.84 (3H, s), 4.06 (2H, t, J=7.5 Hz), 6.54-6.58 (2H, m), 6.77-6.92 (2H, m), 7.38-7.42 (1H, m), 7.72-7.75 (1H, m), 8.79 (1H, brs)

EXAMPLE 9

5-Fluoro-8-isopropoxy-3-(4-methoxyphenyl)-1H-quinolin-4-one

White powder (ethyl acetate)
Melting point 193-194° C.
$^1$H-NMR (CDCl$_3$) δppm:
1.39 (6H, d, J=5.0 Hz), 3.79 (3H, s), 4.58 (1H, q, J=5.0 Hz), 6.79-6.92 (4H, m), 7.54-7.57 (2H, m), 7.68-7.71 (1H, m), 8.80 (1H, brs)

EXAMPLE 10

3-(2,4-Dichlorophenyl)-5-fluoro-8-propoxy-1H-quinolin-4-one

White powder (ethyl acetate)
Melting point 256-259° C.
$^1$H-NMR (DMSO-$d_6$) δppm:
1.01 (3H, t, J=7.5 Hz), 1.79-1.87 (2H, m), 4.08 (2H, t, J=6.3 Hz), 6.88-6.98 (1H, m), 6.96-7.72 (1H, m), 7.37-7.47 (2H, m), 7.65-7.67 (1H, m), 7.75-7.77 (1H, m), 11.42 (1H, brs)

EXAMPLE 11

8-Ethoxy-5-fluoro-3-(4-methoxyphenyl)-1H-quinolin-4-one

Pale yellow powder (ethyl acetate)
Melting point 155-156° C.
$^1$H-NMR (CDCl$_3$) δppm: 1.46 (3H, t, J=7.5 Hz), 3.81 (3H, s), 4.14 (2H, q, J=7.5 Hz), 6.77-6.94 (4H, m), 7.54-7.60 (2H, m), 7.71-7.73 (1H, m), 9.02 (1H, brs)

EXAMPLE 12

3-(2,4-Dimethoxyphenyl)-8-ethoxy-5-fluoro-1H-quinolin-4-one

Pale yellow powder (ethyl acetate)
Melting point 154-155° C.
$^1$H-NMR (CDCl$_3$) δppm:
1.44 (3H, t, J=7.5 Hz), 3.73 (3H, s), 3.81 (3H, s), 4.12 (2H, q, J=7.5 Hz), 6.50-6.53 (2H, m), 6.54-6.89 (2H, m), 7.35-7.39 (1H, m), 7.69-7.72 (1H, m), 8.97 (1H, brs)

EXAMPLE 13

3-(2,4-Dichlorophenyl)-8-ethoxy-5-fluoro-1H-quinolin-4-one

Pale yellow powder (ethyl acetate)
Melting point 236-237° C.
$^1$H-NMR (DMSO-$d_6$) δppm:
1.40 (3H, t, J=7.5 Hz), 4.17 (2H, q, J=7.5 Hz), 6.88-7.00 (1H, m), 7.22-7.32 (1H, m), 7.38-7.45 (2H, m), 7.64-7.65 (1H, m), 7.74-7.75 (1H, m), 11.40 (1H, brs)

EXAMPLE 14

5-Fluoro-3-(4-methoxyphenyl)-8-morpholin-4-yl-1H-quinolin-4-one

Pale yellow powder (ethyl acetate)
Melting point 249-251° C.
$^1$H-NMR (CDCl$_3$) δppm:
2.75-3.22 (4H, m), 3.65-4.15 (4H, m), 6.85-6.93 (3H, m), 7.34-7.40 (1H, m), 7.54-7.58 (2H, m), 7.74-7.77 (1H, m), 10.02 (1H, brs)

EXAMPLE 15

5-Fluoro-3-(2-isopropoxy-4-methoxyphenyl)-8-propoxy-1H-quinolin-4-one

White powder (ethyl acetate)
Melting point 204-206° C.
$^1$H-NMR (CDCl$_3$) δppm:
1.09 (3H, t, J=6.3 Hz), 1.23 (3H, s), 1.26 (3H, s), 1.87-2.01 (2H, m), 3.83 (3H, s), 4.08 (2H, t, J=6.3 Hz), 4.34-4.50 (1H, m), 6.55-6.60 (2H, m), 6.78-6.93 (2H, m), 7.50 (1H, d, J=7.5 Hz), 7.80 (1H, d, J=7.5 Hz), 8.73 (1H, brs)

EXAMPLE 16

5-Fluoro-3-(4-methoxy-2-methylphenyl)-8-propoxy-1H-quinolin-4-one

White powder (ethyl acetate)
Melting point 197-199° C.

¹H-NMR (CDCl₃) δppm:
1.06 (3H, t, J=6.3 Hz), 1.80-2.00 (2H, m), 2.24 (3H, s), 3.80 (3H, s), 4.07 (2H, t, J=6.3 Hz), 6.70-6.94 (4H, m), 7.07 (1H, d, J=7.5 Hz), 7.54 (1H, d, J=7.5 Hz), 8.80 (1H, brs)

EXAMPLE 17

5-Fluoro-3-(2-fluoro-4-methoxyphenyl)-8-propoxy-1H-quinolin-4-one

White powder (ethyl acetate-ethanol)
Melting point 230-232° C.
¹H-NMR (CDCl₃) δppm:
1.05 (3H, t, J=7.5 Hz), 1.80-2.00 (2H, m), 3.80 (3H, s), 4.06 (2H, t, J=7.5 Hz), 6.64-6.93 (4H, m), 7.53-7.60 (1H, m), 7.74-7.78 (1H, m), 8.86 (1H, brs)

EXAMPLE 18

5-Fluoro-3-(4-methoxyphenyl)-8-pyrrolidin-1-yl-1H-quinolin-4-one

Pale brown powder (ethyl acetate-n-hexane)
Melting point 100-105° C.
¹H-NMR (CDCl₃) δppm:
1.90-2.08 (4H, m), 3.01-3.20 (4H, m), 3.81 (3H, s), 6.81-6.94 (3H, m), 7.29-7.34 (1H, m), 7.55-7.60 (2H, m), 7.74-7.76 (1H, m), 9.41 (1H, brs)

EXAMPLE 19

3-(4-Ethoxy-2-methoxyphenyl)-5-fluoro-8-propoxy-1H-quinolin-4-one

Pale brown powder (ethyl acetate)
Melting point 118-120° C.
¹H-NMR (CDCl₃) δppm:
1.06 (3H, t, J=7.5 Hz), 1.39 (3H, t, J=7.5 Hz), 1.83-1.98 (2H, m), 3.75 (3H, s), 4.00-4.14 (4H, m), 6.51-6.55 (2H, m), 6.76-6.91 (2H, m), 7.38 (1H, d, J=6.2 Hz), 7.72 (1H, d, J=6.2 Hz), 8.65 (1H, brs)

EXAMPLE 20

5-Fluoro-3-(4-isopropoxy-2-methoxyphenyl)-8-propoxy-1H-quinolin-4-one

White powder (ethyl acetate-n-hexane)
Melting point 113-115° C.
¹H-NMR (CDCl₃) δppm:
1.04 (3H, t, J=7.5 Hz), 1.33 (3H, s), 1.36 (3H, s), 1.80-1.95 (2H, m), 3.72 (3H, s), 4.03 (2H, t, J=7.5 Hz), 4.50-4.71 (1H, m), 6.49-6.53 (2H, m), 6.78-6.86 (2H, m), 7.34-7.38 (1H, m), 7.42-7.74 (1H, m), 8.82 (1H, brs)

EXAMPLE 21

5,6-Difluoro-3-(4-methoxyphenyl)-8-propoxy-1H-quinolin-4-one

Pale brown powder (ethyl acetate-n-hexane)
Melting point 198-200° C.
¹H-NMR (DMSO-d₆) δppm:
1.02 (3H, t, J=7.3 Hz), 1.78-1.86 (2H, m), 3.75 (3H, s), 4.11 (2H, t, J=6.4 Hz), 6.93 (2H, d, J=8.8 Hz), 7.38 (1H, dd, J=6.5 Hz, J=12.3 Hz), 7.54 (2H, d, J=8.8 Hz), 7.81 (1H, s), 11.50 (1H, brs)

EXAMPLE 22

8-Bromo-5-fluoro-3-(4-methoxyphenyl)-1H-quinolin-4-one

Pale yellow powder (ethyl acetate)
Melting point 134-135° C.
¹H-NMR (DMSO-d₆) δppm:
3.78 (3H, s), 6.94-7.02 (3H, m), 7.52 (2H, d, J=6.3 Hz), 7.84 (1H, s), 7.89-8.00 (1H, m), 11.20 (1H, brs)

EXAMPLE 23

5-Fluoro-3-(4-methoxyphenyl)-8-(pyrrolidin-1-carbonyl)-1H-quinolin-4-one

Orange powder (ethyl acetate)
Melting point 236-237° C.
¹H-NMR (DMSO-d₆) δppm:
1.77-1.91 (4H, m), 3.29-3.34 (2H, m), 3.54-3.59 (2H, m), 3.76 (3H, s), 6.94 (2H, d, J=8.7 Hz), 7.02 (1H, dd, J=8.3 Hz, J=11.8 Hz), 7.53 (2H, d, J=8.7 Hz), 7.71 (1H, dd, J=5.1 Hz, J=8.3 Hz), 7.88 (1H, s), 11.26 (1H, s)

EXAMPLE 24

8-Cyclopropylmethoxy-5-fluoro-3-(4-methoxyphenyl)-1H-quinolin-4-one

Pale yellow powder (ethyl acetate-ethanol)
Melting point 190-191° C.
¹H-NMR (DMSO-d₆) δppm:
0.33-0.39 (2H, m), 0.55-0.62 (2H, m), 1.26-1.34 (1H, m), 3.75 (3H, s), 3.99 (2H, d, J=7.0 Hz), 6.83-6.95 (3H, m), 7.12 (1H, dd, J=3.8 Hz, J=8.8 Hz), 7.53 (2H, d, J=8.6 Hz), 7.82 (1H, s), 11.34 (1H, brs)

EXAMPLE 25

8-(N-Cyclohexyl-N-methylamino)-5-fluoro-3-(4-methoxyphenyl)-1H-quinolin-4-one

Pale yellow powder (ethyl acetate)
Melting point 224-225° C.
¹H-NMR (DMSO-d₆) δppm:
1.00-1.24 (5H, m), 1.53-1.99 (5H, m), 2.65 (3H, s), 3.78 (3H, s), 6.92-6.99 (3H, m), 7.50-7.57 (3H, s), 7.87 (1H, s), 10.93 (1H, brs)

EXAMPLE 26

N-{3-[5-Fluoro-3-(4-methoxyphenyl)-4-oxo-1,4-dihydroquinolin-8-yloxy]propyl}acetamide Pale brown powder (ethanol)
Melting point 229-231° C.
¹H-NMR (DMSO-d₆) δppm:
1.80 (3H, s), 1.91-1.96 (2H, m), 3.24-3.31 (2H, m), 3.74 (3H, s), 4.12 (2H, t, J=5.6 Hz), 6.84-7.13 (4H, m), 7.53 (2H, d, J=8.6 Hz), 7.83 (1H, s), 8.01 (1H, brs), 11.40 (1H, brs)

EXAMPLE 27

N-{3-[5-Fluoro-3-(4-methoxyphenyl)-4-oxo-1,4-dihydroquinolin-8-yloxy]propyl}methanesulfonamide Pale brown powder (ethanol)
Melting point 120-121° C.

$^1$H-NMR (DMSO-d$_6$) δppm:
1.96-2.06 (2H, m), 2.88 (3H, s), 3.10-3.30 (2H, m), 3.75 (3H, s), 4.18 (2H, t, J=5.9 Hz), 6.85-6.95 (3H, m), 7.00-7.16 (2H, m), 7.54 (2H, d, J=8.7 Hz), 7.82 (1H, s), 11.34 (1H, brs)

EXAMPLE 28

5-Fluoro-8-(N-isobutyl-N-methylamino)-3-(4-methoxyphenyl)-1H-quinolin-4-one

White powder (ethyl acetate)
Melting point 144-145° C.
$^1$H-NMR (DMSO-d$_6$) δppm:
0.86 (3H, s), 0.91 (3H, s), 1.61-1.67 (1H, m), 2.61 (3H, s), 2.80 (2H, d, J=6.75 Hz), 3.79 (3H, s), 6.91-6.99 (3H, m), 7.46-7.57 (3H, m), 7.88 (1H, s), 11.02 (1H, brs)

EXAMPLE 29

5-Fluoro-8-(N-isopropyl-N-methylamino)-3-(4-methoxyphenyl)-1H-quinolin-4-one

White powder (ethyl acetate)
Melting point 267-269° C.
$^1$H-NMR (DMSO-d$_6$) δppm:
1.04 (3H, s), 1.06 (3H, s), 2.62 (3H, s), 3.10-3.18 (1H, m), 3.76 (3H, s), 6.90-6.98 (3H, m), 7.47-7.55 (3H, m), 7.85 (1H, s), 10.94 (1H, brs)

EXAMPLE 30

5-Fluoro-3-(4-methoxyphenyl)-8-(N-methyl-N-propylamino)-1H-quinolin-4-one

Pale yellow powder (ethyl acetate)
Melting point 145-146° C.
$^1$H-NMR (DMSO-d$_6$) δppm:
0.79 (3H, t, J=7.5 Hz), 1.31-1.45 (2H, m), 2.63 (3H, s), 2.85 (2H, t, J=7.5 Hz), 3.76 (3H, s), 6.89-6.97 (3H, m), 7.43-7.54 (3H, m), 7.82 (1H, s), 11.07 (1H, brs)

EXAMPLE 31

5-Fluoro-3-(4-methoxyphenyl)-8-(4,4,4-trifluorobutoxy)-1H-quinolin-4-one

White powder (ethyl acetate)
Melting point 171-172° C.
$^1$H-NMR (DMSO-d$_6$) δppm:
1.99-2.08 (2H, m), 2.48-2.61 (2H, m), 3.74 (3H, s), 4.17 (2H, t, J=5.9 Hz), 6.84-6.94 (3H, m), 7.11 (1H, dd, J=3.8 Hz, J=8.8 Hz), 7.53 (2H, d, J=8.7 Hz), 7.82 (1H, s), 11.40 (1H, brs)

EXAMPLE 32

1-{3-[5-fluoro-3-(4-methoxyphenyl)-4-oxo-1,4-dihydroquinolin-8-yloxy]propyl}-1,3,3-trimethyl urea Brown amorphous solid (diethyl ether)
$^1$H-NMR (DMSO-d$_6$) δppm:
2.00-2.05 (2H, m), 2.63 (6H, s), 2.74 (3H, s), 3.20-3.40 (2H, m), 3.76 (3H, s), 4.12 (2H, t, J=6.0 Hz), 6.85-6.96 (3H, m), 7.14 (1H, dd, J=3.9 Hz, J=8.8 Hz), 7.55 (2H, d, J=8.7 Hz), 7.81 (1H, s), 11.40 (1H, brs)

EXAMPLE 33

3-(4-Ethoxyphenyl)-5-fluoro-8-propoxy-1H-quinolin-4-one

Pale yellow powder (ethyl acetate)
Melting point 203-205° C.
$^1$H-NMR (DMSO-d$_6$) δppm:
1.02 (3H, t, J=7.3 Hz), 1.13 (3H, t, J=7.0 Hz), 1.76-1.91 (2H, m), 3.99-4.13 (4H, m), 6.84-6.94 (3H, m), 7.12-7.17 (1H, m), 7.50 (2H, d, J=7.5 Hz), 7.79 (1H, s), 11.25 (1H, brs)

EXAMPLE 34

5-Fluoro-8-[N-(2-methoxyethyl)-N-methylamino]-3-(4-methoxyphenyl)-1H-quinolin-4-one hydrochloride Pale yellow powder (ethyl acetate)
Melting point 100-101° C.
$^1$H-NMR (DMSO-d$_6$) δppm:
2.78 (3H, s), 3.08 (2H, t, J=5.3 Hz), 3.33 (3H, s), 3.49 (2H, t, J=5.3 Hz), 3.81 (3H, s), 6.94-7.02 (3H, m), 7.50-7.62 (3H, m), 8.00 (1H, s), 11.16 (1H, brs)

EXAMPLE 35

3-(4-Cyclopropylmethoxyphenyl)-5-fluoro-8-propoxy-1H-quinolin-4-one

White powder (ethyl acetate)
Melting point 162-163° C.
$^1$H-NMR (DMSO-d$_6$) δppm:
0.30-0.35 (2H, m), 0.54-0.58 (2H, m), 1.01 (3H, t, J=7.5 Hz), 1.10-1.30 (1H, m), 1.72-1.91 (2H, m), 3.80 (2H, d, J=7.0 Hz), 4.07 (2H, t, J=6.4 Hz), 6.84-6.93 (3H, m), 7.11-7.16 (1H, m), 7.50 (2H, d, J=8.8 Hz), 7.79 (1H, s), 11.25 (1H, brs)

EXAMPLE 36

5-Fluoro-8-(2-methoxyethoxy)-3-(4-methoxyphenyl)-1H-quinolin-4-one

Pale yellow powder (ethyl acetate)
Melting point 142-144° C.
$^1$H-NMR (DMSO-d$_6$) δppm:
3.31 (3H, s), 3.70-3.80 (2H, m), 3.75 (3H, s), 4.20-4.30 (2H, m), 6.84-6.94 (3H, m), 7.16 (1H, dd, J=3.6 Hz, J=8.7 Hz), 7.53 (2H, d, J=8.4 Hz), 7.82 (1H, s), 11.10 (1H, brs)

EXAMPLE 37

8-Cyclopentyloxy-5-fluoro-3-(4-methoxyphenyl)-1H-quinolin-4-one

Pale yellow powder (ethyl acetate)
Melting point 213-215° C.
$^1$H-NMR (DMSO-d$_6$) δppm:
1.50-1.70 (2H, m), 1.71-2.00 (6H, m), 3.75 (3H, s), 4.92-4.95 (1H, m), 6.83-6.95 (3H, m), 7.09 (1H, dd, J=3.9 Hz, J=8.8 Hz), 7.53 (2H, d, J=8.6 Hz), 7.80 (1H, s), 11.20 (1H, brs)

EXAMPLE 38

5-Fluoro-3-(4-methylsulfanylphenyl)-8-propoxy-1H-quinolin-4-one

Pale yellow powder (ethyl acetate)
Melting point 198-199° C.

¹H-NMR (CDCl₃) δppm:
1.07 (3H, t, J=7.4 Hz), 1.85-2.04 (2H, m), 2.50 (3H, s), 4.07 (2H, t, J=6.6 Hz), 6.80-6.94 (2H, m), 7.27-7.31 (2H, m), 7.56 (2H, d, J=8.4 Hz), 7.74 (1H, d, J=8.2 Hz), 8.81 (1H, brs)

EXAMPLE 39

5-Fluoro-3-(4-methoxyphenyl)-8-(tetrahydrofuran-2-ylmethoxy)-1H-quinolin-4-one

Pale yellow powder (ethyl acetate)
Melting point 108-110° C.
¹H-NMR (DMSO-d₆) δppm:
1.67-1.75 (1H, m), 1.81-1.90 (2H, m), 2.02-2.09 (1H, m), 3.65-3.83 (2H, m), 3.75 (3H, s), 4.10 (2H, d, J=4.6 Hz), 4.25-4.29 (1H, m), 6.84-6.95 (3H, m), 7.17 (1H, dd, J=3.8 Hz, J=8.8 Hz), 7.53 (2H, d, J=8.7 Hz), 7.82 (1H, s), 11.20 (1H, brs)

EXAMPLE 40

5-Fluoro-3-(4-methoxyphenyl)-8-propylsulfanyl-1H-quinolin-4-one

White powder (ethyl acetate)
Melting point 173-174° C.
¹H-NMR (DMSO-d₆) δppm:
0.90 (3H, t, J=7.3 Hz), 1.40-1.52 (2H, m), 2.79 (2H, t, J=7.2 Hz), 3.77 (3H, s), 6.93-7.04 (3H, m), 7.51-7.55 (2H, m), 7.79-7.87 (2H, m), 11.24 (1H, brs)

EXAMPLE 41

8-Cyclobutylmethoxy-5-fluoro-3-(4-methoxyphenyl)-1H-quinolin-4-one

Pale yellow powder (ethyl acetate)
Melting point 193-194° C.
¹H-NMR (DMSO-d₆) δppm:
1.79-1.93 (4H, m), 2.04-2.09 (2H, m), 2.76-2.81 (1H, m), 3.74 (3H, s), 4.08 (2H, d, J=6.8 Hz), 6.83-6.93 (3H, m), 7.11 (1H, dd, J=3.8 Hz, J=8.8 Hz), 7.52 (2H, d, J=8.6 Hz), 7.82 (1H, s), 11.20 (1H, brs)

EXAMPLE 42

8-tert-Butoxy-5-fluoro-3-(4-methoxyphenyl)-1H-quinolin-4-one

Pale brown powder (ethyl acetate-diethyl ether)
Melting point 206-208° C.
¹H-NMR (DMSO-d₆) δppm:
1.40 (9H, s), 3.76 (3H, s), 6.84-6.96 (3H, m), 7.31 (1H, dd, J=4.3 Hz, J=8.8 Hz), 7.54 (2H, d, J=8.8 Hz), 7.82 (1H, s), 10.95 (1H, brs)

EXAMPLE 43

5-Fluoro-8-methoxy-3-(4-methoxyphenyl)-1H-quinolin-4-one

Pale dark brown powder (ethyl acetate)
¹H-NMR (DMSO-d₆) δppm:
3.76 (3H, s), 3.95 (3H, s), 6.87-6.95 (3H, m), 7.15 (1H, dd, J=3.8 Hz, J=8.8 Hz), 7.54 (2H, d, J=8.7 Hz), 7.76 (1H, s), 11.50 (1H, brs)

EXAMPLE 44

5-Fluoro-8-methoxymethoxy-3-(4-methoxyphenyl)-1H-quinolin-4-one

Pale dark brown powder (dichloromethane-methanol)
¹H-NMR (CDCl₃) δppm:
3.44 (3H, s), 3.76 (3H, s), 5.20 (2H, s), 6.76-6.87 (3H, m), 7.18-7.23 (1H, m), 7.52 (2H, d, J=7.8 Hz), 7.69 (1H, s), 9.68 (1H, brs)

EXAMPLE 45

8-(3-Benzyloxypropoxy)-5-fluoro-3-(4-methoxyphenyl)-1H-quinolin-4-one

Dark brown amorphous solid
¹H-NMR (DMSO-d₆) δppm:
2.08-2.13 (2H, m), 3.68 (2H, t, J=6.2 Hz), 3.77 (3H, s), 4.22 (2H, t, J=6.0 Hz), 4.48 (2H, s), 6.84-6.97 (3H, m), 7.13-7.18 (1H, m), 7.21-7.29 (5H, m), 7.55 (2H, d, J=8.7 Hz), 7.76 (1H, s), 11.25 (1H, brs)

EXAMPLE 46

8-(2-Benzyloxypropoxy)-5-fluoro-3-(4-methoxyphenyl)-1H-quinolin-4-one

Dark brown amorphous solid
¹H-NMR (DMSO-d₆) δppm:
1.32 (3H, d, J=6.2 Hz), 3.76 (3H, s), 3.98-4.24 (3H, m), 4.54-4.69 (2H, m), 6.84-6.96 (3H, m), 7.16-7.30 (6H, m), 7.54 (2H, d, J=8.7 Hz), 7.78 (1H, s), 11.19 (1H, brs)

EXAMPLE 47

8-Cyclopropylmethoxy-5-fluoro-3-(4-methoxyphenyl)-2-methyl-1H-quinolin-4-one

Amberlyst 15 (350 mg, a product of Sigma Aldrich Corp.) was added to a benzene solution (40 ml) of 2-cyclopropylmethoxy-5-fluoroaniline (760 mg, 4.2 mmol) and ethyl α-acetyl-4-methoxyphenyl acetate (1.0 g, 4.2 mmol), and the mixture was heated under reflux for 19 hours while using a Dean-Stark trap and being stirred. The reaction mixture was cooled to room temperature, the resin was removed by filtration, and the filtrate was concentrated under reduced pressure. Diphenyl ether (2.2 ml) was added to the residue, and the mixture was heated using a mantle heater and then stirred for 1 hour under reflux. The reaction mixture was cooled to room temperature and purified directly by silica gel column chromatography (dichloromethane:methanol=80:1→60:1). The purified product was concentrated under reduced pressure, and the residue was recrystallized from ethyl acetate to thereby obtain 120 mg of powdery pale yellow 8-cyclopropylmethoxy-5-fluoro-3-(4-methoxyphenyl)-2-methyl-1H-quinolin-4-one (yield: 8%).
Melting point 167-169° C.
¹H-NMR (DMSO-d₆) δppm:
0.35-0.39 (2H, m), 0.54-0.61 (2H, m), 1.31-1.37 (1H, m), 2.23 (3H, s), 3.76 (3H, s), 4.02 (2H, d, J=7.0 Hz), 6.80-6.94 (3H, m), 7.08-7.18 (3H, m), 10.62 (1H, brs)

The compound of the following Example 48 was prepared in the same manner as the above Example 47, using corresponding starting materials.

EXAMPLE 48

2-Ethyl-5-fluoro-3-(4-methoxyphenyl)-8-propoxy-1H-quinolin-4-one

Pale brown powder (ethyl acetate-n-hexane)
Melting point 169-171° C.
$^1$H-NMR (DMSO-$d_6$) δppm:
0.98-1.05 (6H, m), 1.80-1.89 (2H, m), 2.56 (2H, t, J=7.5 Hz), 3.77 (3H, s), 4.13 (2H, t, J=6.6 Hz), 6.81-6.95 (3H, m), 7.05-7.17 (3H, m), 10.40 (1H, brs)

EXAMPLE 49

5-Fluoro-8-propoxy-3-pyridin-3-yl-1H-quinolin-4-one

5-Fluoro-3-iodo-8-propoxy-1H-quinolin-4-one (600 mg, 1.73 mmol) was suspended in 1,2-dimethoxyethane (12 ml). 3-pyridine boronic acid (752 mg), 1,1'-bis(diphenylphosphino)ferrocene dichloro palladium(II)-dichloromethane complex (PdCl$_2$(DPPF)) (76 mg, 0.093 mmol), and 2N sodium carbonate aqueous solution (2.54 ml) were added to the resulting suspension in that order. The mixture was stirred at 90° C. for 2 hours under a nitrogen atmosphere. After the reaction mixture was cooled to room temperature, water was added, and the resulting mixture was extracted with ethyl acetate. The organic layer was concentrated under reduced pressure, and the residue was then purified by silica gel column chromatography (dichloromethane:methanol=15:1). The purified product was concentrated under reduced pressure, and then recrystallized from ethanol to thereby obtain 185 mg of powdery pale brown 5-fluoro-8-propoxy-3-pyridin-3-yl-1H-quinolin-4-one (yield: 36%).
Melting point 234-236° C.
$^1$H-NMR (DMSO-$d_6$) δppm:
1.01 (3H, t, J=7.3 Hz), 1.77-1.86 (2H, m), 4.08 (2H, t, J=6.4 Hz), 6.93 (1H, dd, J=8.8 Hz, J=12.0 Hz), 7.13-7.18 (1H, m), 7.37-7.42 (1H, m), 7.97 (1H, s), 8.01-8.05 (1H, m), 8.44-8.46 (1H, m), 8.77 (1H, d, J=2.1 Hz), 11.55 (1H, brs)

The compounds of the following Examples 50 to 66 were prepared in the same manner as the above Example 49, using corresponding starting materials.

EXAMPLE 50

3-(4-Ethoxy-3-fluorophenyl)-5-fluoro-8-propoxy-1H-quinolin-4-one

Pale yellow powder (ethanol)
Melting point 176-177° C.
$^1$H-NMR (DMSO-$d_6$) δppm:
1.02 (3H, t, J=7.3 Hz), 1.33 (3H, t, J=6.9 Hz), 1.75-1.89 (2H, m), 4.05-4.14 (4H, m), 6.90 (1H, dd, J=8.7 Hz, J=12.1 Hz), 7.09-7.16 (2H, m), 7.32-7.36 (1H, m), 7.52-7.58 (1H, m), 7.87 (1H, s), 11.45 (1H, s)

EXAMPLE 51

5-Fluoro-8-propoxy-3-pyridin-4-yl-1H-quinolin-4-one

Pale brown powder (ethanol)
Melting point 259-261° C.
$^1$H-NMR (DMSO-$d_6$) δppm:
1.02 (3H, t, J=7.3 Hz), 1.78-1.86 (2H, m), 4.09 (2H, t, J=6.4 Hz), 6.96 (1H, dd, J=8.8 Hz, J=12.0 Hz), 7.19 (1H, dd, J=3.8 Hz, J=8.8 Hz), 7.71 (2H, d, J=6.1 Hz), 8.06 (1H, s), 8.52 (2H, d, J=6.1 Hz), 11.50 (1H, brs)

EXAMPLE 52

5-Fluoro-3-(4-phenoxyphenyl)-8-propoxy-1H-quinolin-4-one

Pale brown powder (ethanol)
Melting point 228-230° C.
$^1$H-NMR (DMSO-$d_6$) δppm:
1.01 (3H, t, J=7.3 Hz), 1.77-1.85 (2H, m), 4.07 (2H, t, J=6.2 Hz), 6.90 (1H, dd, J=8.8 Hz, J=12.1 Hz), 6.97-7.02 (4H, m), 7.10-7.15 (2H, m), 7.34-7.63 (4H, m), 7.88 (1H, s), 11.40 (1H, brs)

EXAMPLE 53

3-(4-Ethylphenyl)-5-fluoro-8-propoxy-1H-quinolin-4-one

White powder (ethyl acetate)
Melting point 153-154° C.
$^1$H-NMR (DMSO-$d_6$) δppm:
1.02 (3H, t, J=7.3 Hz), 1.17 (3H, t, J=7.5 Hz), 1.78-1.86 (2H, m), 2.59 (2H, q, J=7.5 Hz), 4.08 (2H, t, J=6.4 Hz), 6.89 (1H, dd, J=8.8 Hz, J=12.1 Hz), 7.10-7.21 (3H, m), 7.50 (2H, d, J=8.0 Hz), 7.83 (1H, s), 11.40 (1H, brs)

EXAMPLE 54

3-(4-Acetylphenyl)-5-fluoro-8-propoxy-1H-quinolin-4-one

Pale red powder (ethyl acetate)
Melting point 180-181° C.
$^1$H-NMR (DMSO-$d_6$) δppm:
0.95 (3H, t, J=7.5 Hz), 1.71-1.83 (2H, m), 2.51 (3H, m), 4.02 (2H, t, J=6.6 Hz), 6.84-6.91 (1H, m), 7.10-7.14 (1H, m), 7.72 (2H, d, J=8.4 Hz), 7.87-7.90 (3H, m), 11.40 (1H, brs)

EXAMPLE 55

Methyl 4-(5-fluoro-4-oxo-8-propoxy-1,4-dihydroquinolin-3-yl) benzoate

White powder (ethyl acetate)
Melting point 201-202° C.
$^1$H-NMR (DMSO-$d_6$) δppm:
1.01 (3H, t, J=7.3 Hz), 1.77-1.91 (2H, m), 3.86 (3H, s), 4.09 (2H, t, J=6.5 Hz), 6.90-6.99 (1H, m), 7.17-7.22 (1H, m), 7.80 (2H, d, J=8.5 Hz), 7.94-7.98 (3H, m), 11.48 (1H, brs)

EXAMPLE 56

5-Fluoro-8-propoxy-3-[4-(pyrrolidine-1-carbonyl)phenyl]-1H-quinolin-4-one

Pale red powder (ethyl acetate)
Melting point 236-237° C.
$^1$H-NMR (DMSO-$d_6$) δppm:
1.02 (3H, t, J=7.4 Hz), 1.79-1.89 (6H, m), 3.43-3.49 (4H, m), 4.08 (2H, t, J=6.5 Hz), 6.89-6.97 (1H, m), 7.15-7.20 (1H, m), 7.51 (2H, d, J=8.6 Hz), 7.67 (2H, d, J=8.6 Hz), 7.90 (1H, s), 11.40 (1H, brs)

EXAMPLE 57

4-(5-Fluoro-4-oxo-8-propoxy-1,4-dihydroquinolin-3-yl)-N,N-dimethylbenzamide

Pale brown powder (ethyl acetate)
Melting point 235-237° C.
$^1$H-NMR (DMSO-$d_6$) δppm:
1.02 (3H, t, J=7.4 Hz), 1.80-1.89 (2H, m), 2.97 (6H, s), 4.08 (2H, t, J=6.4 Hz), 6.89-6.93 (1H, m), 7.15-7.20 (1H, m), 7.39 (2H, d, J=8.0 Hz), 7.67 (2H, d, J=8.0 Hz), 7.90 (1H, s), 11.41 (1H, brs)

EXAMPLE 58

5-Fluoro-3-furan-2-yl-8-propoxy-1H-quinolin-4-one

Pale brown powder (ethyl acetate)
Melting point 210-212° C.
$^1$H-NMR (DMSO-$d_6$) δppm:
1.02 (3H, t, J=7.4 Hz), 1.78-1.90 (2H, m), 4.10 (2H, t, J=6.6 Hz), 6.54-6.56 (1H, m), 6.90-6.99 (1H, m), 7.15-7.21 (2H, m), 7.64-7.65 (1H, m), 8.20 (1H, s), 11.47 (1H, brs)

EXAMPLE 59

5-Fluoro-8-propoxy-3-thiophen-2-yl-1H-quinolin-4-one

Pale red powder (ethyl acetate)
Melting point 211-213° C.
$^1$H-NMR (DMSO-$d_6$) δppm:
1.02 (3H, t, J=7.5 Hz), 1.78-1.90 (2H, m), 4.10 (2H, t, J=6.5 Hz), 6.92-7.20 (3H, m), 7.41-7.59 (2H, m), 8.34 (1H, s), 11.63 (1H, brs)

EXAMPLE 60

3-(5-Fluoro-4-oxo-8-propoxy-1,4-dihydroquinolin-3-yl)thiophene-2-carbaldehyde

White powder (ethyl acetate)
Melting point 190-191° C.
$^1$H-NMR (DMSO-$d_6$) δppm:
1.01 (3H, t, J=7.4 Hz), 1.79-1.88 (2H, m), 4.08 (3H, t, J=6.5 Hz), 6.92-7.00 (1H, m), 7.18-7.23 (1H, m), 7.32 (1H, d, J=5.0 Hz), 7.98 (1H, s), 8.04-8.06 (1H, m), 9.73 (1H, s), 11.40 (1H, brs)

EXAMPLE 61

3-(4-Dimethylaminophenyl)-5-fluoro-8-propoxy-1H-quinolin-4-one

White powder (ethyl acetate)
Melting point 206-207° C.
$^1$H-NMR (DMSO-$d_6$) δppm:
1.01 (3H, t, J=7.4 Hz), 1.79-1.88 (2H, m), 2.90 (6H, s), 4.07 (2H, t, J=6.4 Hz), 6.71 (2H, d, J=9.0 Hz), 6.82-6.90 (1H, m), 7.09-7.14 (1H, m), 7.45 (2H, d, J=9.0 Hz), 7.76 (1H, s), 11.18 (1H, brs)

EXAMPLE 62

3-(3,4-Dimethoxyphenyl)-5-fluoro-8-propoxy-1H-quinolin-4-one

Pale red powder (ethyl acetate)
Melting point 217-218° C.
$^1$H-NMR (DMSO-$d_6$) δppm:
1.02 (3H, t, J=7.5 Hz), 1.78-1.88 (2H, m), 3.76 (6H, s), 4.07 (2H, t, J=6.4 Hz), 6.85-6.97 (2H, m), 7.08-7.16 (2H, m), 7.30 (1H, s), 7.82 (1H, s), 11.28 (1H, brs)

EXAMPLE 63

5-Fluoro-3-(6-methoxypyridin-3-yl)-8-propoxy-1H-quinolin-4-one

White powder (ethyl acetate)
Melting point 215-216° C.
$^1$H-NMR (DMSO-$d_6$) δppm:
1.02 (3H, t, J=7.5 Hz), 1.77-1.91 (2H, m), 3.86 (3H, s), 4.08 (2H, t, J=6.3 Hz), 6.81-6.96 (2H, m), 7.14-7.19 (1H, m), 7.77-7.99 (2H, m), 8.35 (1H, s), 11.39 (1H, brs)

EXAMPLE 64

3-(2,6-Dimethoxypyridin-3-yl)-5-fluoro-8-propoxy-1H-quinolin-4-one

Pale red powder (ethyl acetate)
Melting point 198-199° C.
$^1$H-NMR (DMSO-$d_6$) δppm:
1.01 (3H, t, J=7.3 Hz), 1.76-1.90 (2H, s), 3.83 (3H, s). 3.89 (3H, s), 4.07 (2H, t, J=6.3 Hz), 6.39 (1H, d, J=7.1 Hz), 6.86-6.94 (1H, m), 7.13-7.17 (1H, m), 7.68 (1H, d, J=7.1 Hz), 7.81 (1H, s), 11.23 (1H, brs)

EXAMPLE 65

3-(2,5-Dimethoxyphenyl)-5-fluoro-8-propoxy-1H-quinolin-4-one

Pale red powder (ethyl acetate)
Melting point 156-157° C.
$^1$H-NMR (DMSO-$d_6$) δppm:
1.03 (3H, t, J=7.3 Hz), 1.80-1.90 (2H, m), 3.65 (3H, s), 3.71 (3H, s), 4.09 (2H, t, J=6.3 Hz), 6.87-6.91 (4H, m), 6.94-6.95 (1H, m), 7.73 (1H, s), 11.18 (1H, brs)

EXAMPLE 66

8-Cyclopropylmethoxy-1-ethyl-5-fluoro-3-(4-methoxyphenyl)-1H-quinolin-4-one

Brown powder (ethyl acetate-n-hexane)
Melting point 150-152° C.
$^1$H-NMR (DMSO-$d_6$) δppm:
0.34-0.38 (2H, m), 0.57-0.64 (2H, m), 1.27-1.39 (4H, m), 3.75 (3H, s), 3.92 (2H, d, J=7.2 Hz), 4.60 (2H, q, J=6.8 Hz), 6.91-6.99 (3H, m), 7.17 (1H, dd, J=4.5 Hz, J=8.9 Hz), 7.60 (2H, d, J=8.7 Hz), 7.98 (1H, s)

EXAMPLE 67

5-Fluoro-3-(4-methoxyphenyl)-2-methyl-8-propoxy-1H-quinolin-4-one

5-Fluoro-3-iodo-2-methyl-8-propoxy-1H-quinolin-4-one (400 mg, 1.11 mmol), 4-methoxyphenyl boronic acid (504 mg, 3.3 mmol), 1,1'-bis(diphenylphosphino)ferrocene dichloro palladium (II)-dichloro methane complex (PdCl$_2$ (DPPF)) (100 mg, 0.12 mmol) and a 2N sodium carbonate aqueous solution (1 ml) were added to 1,2-dimethoxyethane (3 ml), and the mixture was heated at 170° C. for 10 minutes (microwave reactor). The reaction mixture was cooled to room temperature, and filtration with Celite was carried out. The filtrate was extracted with dichloromethane, and washed with water. The organic layer was dried over anhydrous magnesium sulfate, and then concentrated under reduced pressure. The residue was then purified by silica gel column chromatography (dichloromethane:methanol=100:0→40:1). The purified product was concentrated under reduced pressure, and the residue was recrystallized from ethyl acetate to thereby obtain 230 mg of powdery white 5-fluoro-3-(4-methoxyphenyl)-2-methyl-8-propoxy-1H-quinolin-4-one (yield: 61%).
Melting point 211-212° C.
$^1$H-NMR (DMSO-d$_6$) δppm:
0.98 (3H, t, J=7.3 Hz), 1.79-1.90 (2H, m), 2.23 (3H, s), 3.76 (3H, s), 4.10 (2H, t, J=6.5 Hz), 6.93-6.95 (2H, m), 7.07-7.09 (2H, m), 7.72-7.73 (1H, m), 7.83 (1H, s), 10.50 (1H, brs)

The compounds of the following Examples 68 to 85 were prepared in the same manner as the above Example 67, using corresponding starting materials.

EXAMPLE 68

5-Fluoro-2-methyl-8-propoxy-3-pyridin-3-yl-1H-quinolin-4-one

White powder (ethyl acetate)
Melting point 190-192° C.
$^1$H-NMR (DMSO-d$_6$) δppm:
0.99 (3H, t, J=7.5 Hz), 1.77-1.89 (2H, m), 2.27 (3H, s), 4.12 (2H, t, J=6.7 Hz), 6.85-6.93 (1H, m), 7.16-7.21 (1H, m), 7.38-7.43 (1H, m), 7.63-7.67 (1H, m). 8.40-8.50 (2H, m), 10.70 (1H, brs)

EXAMPLE 69

5-Fluoro-2-methyl-8-propoxy-3-pyridin-4-yl-1H-quinolin-4-one

White powder (ethyl acetate)
Melting point 265-266° C.
$^1$H-NMR (DMSO-d$_6$) δppm:
0.99 (3H, t, J=7.5 Hz), 1.78-1.92 (2H, m), 2.28 (3H, s), 4.12 (2H, t, J=6.8 Hz), 6.86-6.94 (1H, m), 7.17-7.21 (1H, m), 7.25 (2H, d, J=6.0 Hz), 8.55 (2H, d, J=6.0 Hz), 10.72 (1H, brs)

EXAMPLE 70

5-Fluoro-2-methyl-8-propoxy-3-(4-trifluoromethoxyphenyl)-1H-quinolin-4-one

Pale yellow powder (ethyl acetate)
Melting point 167-168° C.
$^1$H-NMR (DMSO-d$_6$) δppm:
0.99 (3H, t, J=7.3 Hz), 1.78-1.92 (2H, m), 2.25 (3H, s), 4.10 (2H, t, J=6.6 Hz), 6.83-6.92 (1H, m), 7.15-7.20 (1H, m), 7.31-7.38 (4H, m), 10.64 (1H, brs)

EXAMPLE 71

3-(4-Ethylphenyl)-5-fluoro-2-methyl-8-propoxy-1H-quinolin-4-one

Pale red powder (ethyl acetate)
Melting point 221-222° C.
$^1$H-NMR (DMSO-d$_6$) δppm:
0.99 (3H, t, J=7.3 Hz), 1.18 (3H, t, J=7.5 Hz), 1.80-1.89 (2H, m), 2.23 (3H, s), 2.58 (2H, q, J=7.5 Hz), 4.10 (2H, t, J=6.6 Hz), 6.82-6.89 (1H, m), 7.08-7.22 (5H, m), 10.53 (1H, brs)

EXAMPLE 72

5-Fluoro-2-methyl-8-propoxy-3-thiophen-2-yl-1H-quinolin-4-one

White powder (ethyl acetate)
Melting point 233-234° C.
$^1$H-NMR (DMSO-d$_6$) δppm:
0.98 (3H, t, J=7.3 Hz), 1.77-1.89 (2H, m), 2.46 (3H, s), 4.11 (2H, t, J=6.8 Hz), 6.86-7.20 (4H, m), 7.52-7.55 (1H, m), 10.70 (1H, brs)

EXAMPLE 73

3-(4-Dimethylaminophenyl)-5-fluoro-2-methyl-8-propoxy-1H-quinolin-4-one

White powder (ethyl acetate)
Melting point 255-257° C.
$^1$H-NMR (DMSO-d$_6$) δppm:
1.00 (3H, t, J=7.5 Hz), 1.80-1.90 (2H, m), 2.26 (3H, s), 2.91 (6H, s), 4.11 (2H, t, J=6.6 Hz), 6.72 (2H, d, J=8.7 Hz), 6.80-6.89 (1H, m), 7.00 (2H, d, J=8.7 Hz), 7.11-7.17 (1H, m), 10.45 (1H, brs)

EXAMPLE 74

5-Fluoro-3-(4-fluorophenyl)-2-methyl-8-propoxy-1H-quinolin-4-one

Pale brown powder (ethyl acetate)
Melting point 196-197° C.
$^1$H-NMR (DMSO-d$_6$) δppm:
1.00 (3H, t, J=7.3 Hz), 1.80-1.91 (2H, m), 2.25 (3H, s), 4.12 (2H, t, 6.8 Hz), 6.84-6.92 (1H, m), 7.15-7.29 (5H, m), 10.06 (1H, brs)

EXAMPLE 75

3-(2,4-Dimethoxyphenyl)-5-fluoro-2-methyl-8-propoxy-1H-quinolin-4-one

Pale brown powder (ethyl acetate)
Melting point 100-101° C.
$^1$H-NMR (DMSO-d$_6$) δppm:
0.99 (3H, t, J=7.5 Hz), 1.80-1.86 (2H, m), 2.11 (3H, s), 3.65 (3H, s), 3.78 (3H, s), 4.10 (2H, t, J=6.8 Hz), 6.51-6.59 (2H, m), 6.80-6.94 (2H, m), 7.11-7.17 (1H, m), 10.47 (1H, brs)

EXAMPLE 76

5-Fluoro-3-furan-2-yl-2-methyl-8-propoxy-1H-quinolin-4-one

Pale brown powder (ethyl acetate)
Melting point 203-204° C.
$^1$H-NMR (DMSO-d$_6$) δppm:
0.99 (3H, t, J=7.5 Hz), 1.78-1.89 (2H, m), 2.47 (3H, s), 4.10 (2H, t, J=6.8 Hz), 6.52-6.54 (1H, m), 6.67-6.69 (1H, m), 6.86-6.95 (1H, m), 7.15-7.20 (1H, m), 7.67-7.68 (1H, m), 10.66 (1H, m)

EXAMPLE 77

5-Fluoro-3-(4-methoxyphenyl)-8-propoxy-2-trifluoromethyl-1H-quinolin-4-one

White powder (n-hexane-ethyl acetate)
Melting point 170-171° C.
$^1$H-NMR (DMSO-$d_6$) δppm:
1.00 (3H, t, J=7.3 Hz), 1.76-1.90 (2H, m), 3.80 (3H, s), 4.11 (2H, t, J=6.5 Hz), 6.98 (2H, d, J=8.7 Hz), 7.15-7.25 (4H, m), 10.11 (1H, brs)

EXAMPLE 78

5-Fluoro-3-furan-2-yl-8-propoxy-2-trifluoromethyl-1H-quinolin-4-one

Pale yellow powder (n-hexane-ethyl acetate)
Melting point 134-136° C.
$^1$H-NMR (DMSO-$d_6$) δppm:
0.99 (3H, t, J=7.5 Hz), 1.76-1.90 (2H, m), 4.11 (2H, t, J=6.6 Hz), 6.59-6.65 (2H, m), 7.21-7.33 (2H, m), 7.81 (1H, m), 10.08 (1H, brs)

EXAMPLE 79

3-(4-Dimethylaminophenyl)-5-fluoro-8-propoxy-2-trifluoromethyl-1H-quinolin-4-one Pale yellow powder (n-hexane-ethyl acetate)
Melting point 176-177° C.
$^1$H-NMR (DMSO-$d_6$) δppm:
1.00 (3H, t, J=7.4 Hz), 1.76-1.91 (2H, m), 2.94 (6H, s), 4.11 (2H, t, J=6.6 Hz), 6.75 (2H, d, J=8.8 Hz), 7.03 (2H, d, J=8.8 Hz), 7.21-7.24 (2H, m), 10.00 (1H, brs)

EXAMPLE 80

3-(4-Ethylphenyl)-5-fluoro-8-propoxy-2-trifluoromethyl-1H-quinolin-4-one

White powder (n-hexane-ethyl acetate)
Melting point 187-188° C.
$^1$H-NMR (DMSO-$d_6$) δppm:
1.00 (3H, t, J=7.3 Hz), 1.20 (3H, t, J=7.5 Hz), 1.77-1.91 (2H, m), 2.62-2.71 (2H, q, J=7.5 Hz), 4.12 (2H, t, J=6.6 Hz), 7.13-7.29 (6H, m), 10.23 (1H, brs)

EXAMPLE 81

5-Fluoro-3-(4-fluorophenyl)-8-propoxy-2-trifluoromethyl-1H-quinolin-4-one

Brown powder (n-hexane-ethyl acetate)
Melting point 154-155° C.
$^1$H-NMR (DMSO-$d_6$) δppm:
1.02 (3H, t, J=7.3 Hz), 1.81-1.89 (2H, m), 4.13 (2H, t, J=6.5 Hz), 7.10-7.31 (4H, m), 7.80-7.86 (1H, m), 8.08 (1H, s), 10.24 (1H, brs)

EXAMPLE 82

5-Fluoro-8-propoxy-3-(4-trifluoromethoxyphenyl)-2-trifluoromethyl-1H-quinolin-4-one Pale red powder (n-hexane-ethyl acetate)
Melting point 143-144° C.
$^1$H-NMR (DMSO-$d_6$) δppm:
1.00 (3H, t, J=7.3 Hz), 1.77-1.91 (2H, m), 4.12 (2H, t, J=6.6 Hz), 7.19-7.54 (6H, m), 10.44 (1H, brs)

EXAMPLE 83

5-Fluoro-2-isopropyl-3-(4-methoxyphenyl)-8-propoxy-1H-quinolin-4-one

White powder (ethyl acetate-n-hexane)
Melting point 195-197° C.
$^1$H-NMR (DMSO-$d_6$) δppm:
1.00 (3H, t, J=7.3 Hz), 1.16 (6H, d, J=7.0 Hz), 1.78-1.92 (2H, m), 2.86-2.97 (1H, m), 3.77 (3H, s), 4.13 (2H, t, J=6.4 Hz), 6.84-7.22 (6H, m), 8.98 (1H, brs)

EXAMPLE 84

5-Fluoro-3-furan-2-yl-2-isopropyl-8-propoxy-1H-quinolin-4-one

White powder (ethyl acetate-n-hexane)
Melting point 113-114° C.
$^1$H-NMR (DMSO-$d_6$) δppm:
0.99 (3H, t, J=7.5 Hz), 1.21 (6H, d, J=7.0 Hz), 1.80-1.89 (2H, m), 3.11-3.16 (1H, m), 4.12 (2H, t, J=6.4 Hz), 6.48-6.54 (2H, m), 6.90-6.98 (1H, m), 7.20-7.25 (1H, m), 7.69-7.70 (1H, m), 9.29 (1H, brs)

EXAMPLE 85

5-Fluoro-8-propoxy-3-thiophen-2-yl-2-trifluoromethyl-1H-quinolin-4-one

Pale yellow powder (ethyl acetate-n-hexane)
Melting point 149-150° C.
$^1$H-NMR (DMSO-$d_6$) δppm:
1.00 (3H, t, J=7.4 Hz), 1.76-1.90 (2H, m), 4.11 (2H, t, 6.4 Hz), 7.10-7.30 (4H, m), 7.72-7.75 (1H, m), 10.52 (1H, brs)

EXAMPLE 86

5-Fluoro-8-furan-2-yl-3-(4-methoxyphenyl)-1H-quinolin-4-one 8-bromo-5-fluoro-3-(4-methoxyphenyl)-1H-quinolin-4-one (150 mg, 0.43 mmol), 2-furan boronic acid (145 mg, 1.3 mmol), 1,1'-bis(diphenylphosphino)ferrocene dichloro palladium (II)-dichloromethane complex (PdCl$_2$(DPPF)) (35 mg, 0.04 mmol) and a 2N sodium carbonate aqueous solution (1 ml) were added to 1,2-dimethoxyethane (3 ml), and the mixture was heated at 180° C. for 10 minutes (microwave reactor). After the reaction mixture was cooled to room temperature, dichloromethane was added, and then filtration with Celite was carried out. The filtrate was extracted with dichloromethane and washed with water. The organic layer was dried over anhydrous magnesium sulfate, and then concentrated under reduced pressure. The residue was then purified by silica gel column chromatography (dichloromethane). The purified product was concentrated under reduced pressure, and the residue was recrystallized from n-hexane-ethyl acetate to thereby obtain 100 mg of powdery slightly orange 5-fluoro-8-furan-2-yl-3-(4-methoxyphenyl)-1H-quinolin-4-one (yield: 70%).
Melting point 209-211° C.
$^1$H-NMR (DMSO-d$_6$) δppm:
3.79 (3H, s), 6.74-6.77 (1H, m), 6.96-7.00 (3H, m), 7.07-7.15 (1H, m), 7.55-7.59 (2H, m), 7.81-7.93 (3H, m), 11.00 (1H, brs)

The compounds of the following Examples 87 and 88 were prepared in the same manner as the above Example 86, using corresponding starting materials.

EXAMPLE 87

5-Fluoro-3-(4-methoxyphenyl)-8-thiophen-3-yl-1H-quinolin-4-one

Pale yellow powder (ethyl acetate)
Melting point 183-184° C.
$^1$H-NMR (DMSO-d$_6$) δppm:
3.76 (3H, s), 6.93-7.09 (3H, m), 7.30-7.32 (1H, m), 7.49-7.54 (3H, m), 7.76-7.80 (3H, m), 10.64 (1H, brs)

EXAMPLE 88

8-Benzo[b]thiophen-2-yl-5-fluoro-3-(4-methoxyphenyl)-1H-quinolin-4-one

Pale yellow powder (ethyl acetate)
Melting point 276-277° C.
$^1$H-NMR (DMSO-d$_6$) δppm:
3.76 (3H, s), 6.84-6.92 (3H, m), 7.30-7.40 (2H, m), 7.62-7.66 (2H, m), 7.84-7.99 (5H, m), 11.03 (1H, brs)

EXAMPLE 89

4-(5-Fluoro-4-oxo-8-propoxy-1,4-dihydroquinolin-3-yl)benzoic acid

Methyl 4-(5-fluoro-4-oxo-8-propoxy-1,4-dihydroquinolin-3-yl)benzoate (330 mg, 0.93 mmol) was suspended in a mixed solvent of ethanol (3 ml) and THF (3 ml). A 1.24N lithium hydroxide aqueous solution (2 ml) was added, and the mixture was stirred at room temperature for 3 hours. Water was added to the reaction mixture, and then the resulting mixture was extracted with dichloromethane. The organic layer was washed with water, dried over magnesium sulfate, and concentrated to dryness under reduced pressure to thereby obtain 300 mg of powdery white 4-(5-fluoro-4-oxo-8-propoxy-1,4-dihydroquinolin-3-yl)benzoic acid (yield: 95%).
$^1$H-NMR (DMSO-d$_6$) δppm:
1.01-1.07 (3H, t, J=7.3 Hz), 1.80-1.91 (2H, m), 4.09-4.14 (2H, t, J=6.4 Hz), 6.85-7.24 (3H, m), 7.75-7.78 (2H, m), 7.92-7.95 (2H, m), 11.51 (1H, brs), 12.84 (1H, brs)

EXAMPLE 90

5-Fluoro-3-[4-(morpholine-4-carbonyl)phenyl]-8-propoxy-1H-quinolin-4-one 4-(5-Fluoro-4-oxo-8-propoxy-1,4-dihydroquinolin-3-yl) benzoic acid (260 mg, 0.76 mmol), morpholine (99.5 mg, 1.14 mmol), WSC (189 mg, 0.99 mmol) and HOBT (151 mg, 0.99 mmol) were added to DMF (10 ml), and the mixture was stirred at room temperature for 15 hours. The reaction mixture was concentrated under reduced pressure, and the residue was then purified by silica gel column chromatography (dichloromethane:methanol=30:1). The purified product was concentrated under reduced pressure, and the residue was recrystallized from ethyl acetate to thereby obtain 80 mg of powdery white 5-fluoro-3-[4-(morpholine-4-carbonyl)phenyl]-8-propoxy-1H-quinolin-4-one (yield: 26%).
Melting point 234-236° C.
$^1$H-NMR (DMSO-d$_6$) δppm:
1.02 (3H, t, J=7.4 Hz), 1.80-1.89 (2H, m), 3.40-3.60 (8H, m), 4.09 (2H, t, J=6.5 Hz), 6.89-6.98 (1H, m), 7.16-7.21 (1H, m), 7.41 (2H, d, J=8.3 Hz), 7.69 (2H, d, J=8.3 Hz), 7.91 (1H, s), 11.41 (1H, brs)

EXAMPLE 91

5-Fluoro-3-(4-methoxyphenyl)-1-methyl-8-propoxy-1H-quinolin-4-one

Sodium hydride (60% in oil, 76 mg, 1.9 mmol) was added to a DMF solution (10 ml) of 5-fluoro-3-(4-methoxyphenyl)-8-propoxy-1H-quinolin-4-one (400 mg, 1.22 mmol). The mixture was stirred at room temperature for 15 minutes. Methyl iodide (225 mg, 1.6 mmol) was added thereto, and then the resulting mixture was stirred at room temperature for 19 hours. Water and ethyl acetate were added to the reaction mixture to separate the mixture into two layers. The organic layer was washed with water, dried over anhydrous sodium sulfate, and then concentrated under reduced pressure. The residue was then purified by silica gel column chromatography (n-hexane:ethyl acetate=1:1). The purified product was concentrated under reduced pressure, and the residue was recrystallized from ethyl acetate to thereby obtain 365 mg of powdery pale yellow 5-fluoro-3-(4-methoxyphenyl)-1-methyl-8-propoxy-1H-quinolin-4-one (yield: 72%).
Melting point 147-148° C.
$^1$H-NMR (DMSO-d$_6$) δppm:
0.98 (3H, t, J=7.5 Hz), 1.77 (2H, m), 3.76 (3H, s), 3.98 (2H, t, J=6.4 Hz), 4.08 (3H, s), 6.91-7.01 (3H, m), 7.19-7.24 (1H, m), 7.57-7.61 (2H, m), 7.96 (1H, s)

The compounds of the following Examples 92 to 94 were prepared in the same manner as the above Example 91, using corresponding starting materials.

EXAMPLE 92

1-Ethyl-5-fluoro-3-(4-methoxyphenyl)-8-propoxy-1H-quinolin-4-one

White powder (ethyl acetate)
Melting point 123-125° C.
$^1$H-NMR (DMSO-d$_6$) δppm:
1.00 (3H, t, J=7.3 Hz), 1.29 (3H, t, J=6.8 Hz), 1.79-1.88 (2H, m), 3.76 (3H, s), 4.03 (2H, t, J=6.5 Hz), 4.52 (2H, q, J=6.8 Hz), 6.91-7.02 (3H, m), 7.22-7.27 (1H, m), 7.60 (2H, d, J=8.7 Hz), 8.00 (1H, s)

EXAMPLE 93

1-(2-Ethoxyethyl)-5-fluoro-3-(4-methoxyphenyl)-8-propoxy-1H-quinolin-4-one

White powder (ethyl acetate)
Melting point 108-109° C.
$^1$H-NMR (DMSO-d$_6$) δppm:
0.96-1.09 (6H, m), 1.77-1.89 (2H, m), 3.65 (2H, t, J=5.0 Hz), 3.78 (3H, s), 4.02 (2H, t, J=6.8 Hz), 4.72 (2H, t, J=5.0 Hz), 6.94-7.04 (3H, m), 7.23-7.29 (1H, m), 7.57 (2H, d, J=8.7 Hz), 7.93 (1H, s)

EXAMPLE 94

1-Cyclopropylmethyl-5-fluoro-3-(4-methoxyphenyl)-8-propoxy-1H-quinolin-4-one Pale yellow powder (n-hexane)
Melting point 60-62° C.
$^1$H-NMR (DMSO-$d_6$) δppm:
0.36-0.51 (4H, m), 1.07 (3H, t, J=7.4 Hz), 1.26-1.30 (1H, m), 1.86-1.94 (2H, m), 4.09 (2H, t, J=6.5 Hz), 6.96-7.08 (3H, m), 7.28-7.33 (1H, m), 7.61-7.66 (2H, m), 8.05 (1H, s)

EXAMPLE 95

5-Fluoro-3-(4-hydroxyphenyl)-8-propoxy-1H-quinolin-4-one

A dichloromethane solution (5 ml) of 5-fluoro-3-(4-methoxyphenyl)-8-propoxy-1H-quinolin-4-one (249 mg, 0.76 mmol) was cooled to −10° C. in a methanol-ice bath. A 1N boron tribromide (4.08 ml) was added thereto, and the mixture was stirred at room temperature for 6 hours. Ice water and dichloromethane were added to the reaction mixture, and the resultant insoluble matter was collected by filtration. The filtrate was separated and the organic layer was concentrated under reduced pressure. The residue and the substance remaining on the filter were mixed, and the mixture was purified by silica gel column chromatography (dichloromethane:methanol=60:1→25:1). The purified product was concentrated under reduced pressure. Ethyl acetate was added to crystallize the residue. The crystals were collected by filtration, washed with ethyl acetate, and then dried to thereby obtain 220 mg of powdery pale yellow 5-fluoro-3-(4-hydroxyphenyl)-8-propoxy-1H-quinolin-4-one (yield: 92%).
Melting point 271-272° C.
$^1$H-NMR (DMSO-$d_6$) δppm:
1.03 (3H, t, J=7.3 Hz), 1.78-1.87 (2H, m), 4.08 (2H, t, J=6.4 Hz), 6.77 (2H, d, J=8.6 Hz), 6.87 (1H, dd, J=8.8 Hz, J=12.1 Hz), 7.12 (1H, dd, J=3.9 Hz, J=8.8 Hz), 7.41 (2H, d, J=8.6 Hz), 7.77 (1H, s), 9.43 (1H, brs), 11.20 (1H, brs)

EXAMPLE 96

5-Fluoro-8-hydroxy-3-(4-hydroxyphenyl)-1H-quinolin-4-one

5-Fluoro-8-methoxy-3-(4-methoxyphenyl)-1H-quinolin-4-one (1.0 g, 3.34 mmol) was suspended in dichloromethane (40 ml), and the suspension was cooled to −10° C. in a methanol-ice bath. A 1N boron tribromide (17 ml) was added thereto, and the resulting mixture was stirred at room temperature for 15 hours. Ice water and dichloromethane were added to the reaction mixture, and the resultant insoluble matter was collected by filtration. The substance remaining on the filter was washed with water, dried and purified by silica gel column chromatography (dichloromethane:methanol=20:1→8:1→ethyl acetate:methanol=4:1). The purified product was concentrated under reduced pressure and ethyl acetate was then added to crystallize the residue. The crystals were collected by filtration, washed with ethyl acetate, and dried to thereby obtain 360 mg of powdery pale gray 5-fluoro-8-hydroxy-3-(4-hydroxyphenyl)-1H-quinolin-4-one (yield: 40%).
Melting point 303-305° C. (decomposition)
$^1$H-NMR (DMSO-$d_6$) δppm:
6.74-6.82 (3H, m), 6.94 (1H, dd, J=4.1 Hz, J=8.5 Hz), 7.41 (2H, d, J=8.3 Hz), 7.74 (1H, s), 9.46 (1H, brs), 10.70 (1H, brs), 11.32 (1H, brs)

EXAMPLE 97

5-Fluoro-3-(4-hydroxy-2-methoxyphenyl)-8-propoxy-1H-quinolin-4-one

Aluminum chloride (108 mg, 0.81 mmol) was added to a dichloromethane solution (5 ml) of 5-fluoro-3-(4-isopropoxy-2-methoxyphenyl)-8-propoxy-1H-quinolin-4-one (120 mg, 0.31 mmol). The mixture was stirred at room temperature for 1 hour. Water and dichloromethane were added to the reaction mixture, and separated. The organic layer was then washed with water. The washed organic layer was dried over anhydrous magnesium sulfate, and concentrated under reduced pressure. The residue was then purified by silica gel column chromatography (dichloromethane:methanol=10:1). The purified product was concentrated under reduced pressure, and the residue was recrystallized from ethyl acetate to thereby obtain 100 mg of powdery white 5-fluoro-3-(4-hydroxy-2-methoxyphenyl)-8-propoxy-1H-quinolin-4-one (yield: 90%).
Melting point 251-253° C.
$^1$H-NMR (DMSO-$d_6$) δppm:
1.01-1.07 (3H, t, J=7.4 Hz), 1.77-1.88 (2H, m), 3.63 (3H, s), 4.07-4.12 (2H, t, J=6.6 Hz), 6.33-6.43 (2H, m), 6.84-6.90 (1H, m), 7.02-7.11 (2H, m), 7.61-7.64 (1H, m), 9.39 (1H, s), 11.07 (1H, brs)

The compound of the following Example 98 was prepared in the same manner as the above Example 97, using corresponding starting materials.

EXAMPLE 98

5-Fluoro-3-(2-hydroxy-4-methoxyphenyl)-8-propoxy-1H-quinolin-4-one

White powder (ethyl acetate)
Melting point 208-209° C.
$^1$H-NMR (DMSO-$d_6$) δppm:
1.02 (3H, t, J=7.5 Hz), 1.81-1.90 (2H, m), 3.73 (3H, s), 4.11 (2H, t, J=6.5 Hz), 6.43-6.51 (2H, m), 6.98-7.06 (1H, m), 7.16-7.25 (2H, m), 7.95 (1H, s), 10.23 (1H, s), 11.93 (1H, brs)

EXAMPLE 99

5-Fluoro-8-hydroxy-3-(4-methoxyphenyl)-1H-quinolin-4-one

2N Hydrochloric acid (6.0 ml) was added to an ethanol solution (18 ml) of 5-fluoro-8-methoxymethoxy-3-(4-methoxyphenyl)-1H-quinolin-4-one (350 mg, 1.06 mmol). The mixture was stirred at 55° C. for 1 hour. The stirred mixture was cooled to room temperature, and 1N sodium hydrate (11.6 ml) was added thereto to obtain a pH of 3 to 4. The mixture in which pH was adjusted was concentrated under reduced pressure, and the residue was then purified by silica gel column chromatography (dichloromethane:methanol=50:1→20:1). The purified product was concentrated under reduced pressure, and the residue was crystallized from ethanol, collected by filtration, washed with ethanol, and dried to thereby obtain 165 mg of powdery pale dark brown 5-fluoro-8-hydroxy-3-(4-methoxyphenyl)-1H-quinolin-4-one (yield: 54%).
Melting point 270-272° C.
¹H-NMR (DMSO-d₆) δppm:
3.75 (3H, s), 6.79 (1H, dd, J=8.5 Hz, J=12.1 Hz), 6.90-6.97 (3H, m), 7.53 (2H, d, J=8.6 Hz), 7.77 (1H, s), 10.60 (1H, brs), 11.40 (1H, brs)

EXAMPLE 100

5-Fluoro-3-(2-hydroxymethylthiophen-3-yl)-8-propoxy-1H-quinolin-4-one 3-(5-Fluoro-4-oxo-8-propoxy-1,4-dihydroquinolin-3-yl)thiophene-2-carbaldehyde (120 mg, 0.39 mmol) was suspended in ethanol (5 ml), and sodium borohydride (19.24 mg) was added to the suspension. The resulting mixture was stirred at room temperature for 1 hour. Dichloromethane was added to the reaction mixture, which was washed with water. The organic layer was dried over anhydrous magnesium sulfate and concentrated under reduced pressure. The residue was then purified by silica gel column chromatography (dichloromethane:methanol=30:1). The purified product was concentrated under reduced pressure, and the residue was recrystallized from ethyl acetate to thereby obtain 110 mg of powdery white 5-fluoro-3-(2-hydroxymethylthiophen-3-yl)-8-propoxy-1H-quinolin-4-one (yield: 82%).
Melting point 181-184° C.
¹H-NMR (DMSO-d₆) δppm:
1.01 (3H, t, J=7.3 Hz), 1.79-1.88 (2H, m), 4.07 (2H, t, J=6.4 Hz), 4.47 (2H, d, J=5.4 Hz), 5.48 (1H, t, J=5.4 Hz), 6.87-6.96 (1H, m), 7.11-7.19 (2H, m), 7.39-7.40 (1H, m), 7.88 (1H, s), 11.36 (1H, brs)

EXAMPLE 101

5-Fluoro-8-(3-hydroxypropoxy)-3-(4-methoxyphenyl)-1H-quinolin-4-one 8-(3-Benzyloxypropoxy)-5-fluoro-3-(4-methoxyphenyl)-1H-quinolin-4-one (1.95 g, 4.49 mmol) and a 10% palladium carbon (720 mg) were added to ethanol (50 ml). The mixture was stirred at 50° C. for 7.5 hours under a hydrogen atmosphere (1 atmosphere) and subjected to a catalytic reduction. The reaction mixture was cooled to room temperature, and filtration with Celite was conducted to remove the solvent. The filtrate was concentrated under reduced pressure. The residue was then purified by silica gel column chromatography (dichloromethane:methanol=80:1→20:1). The purified product was concentrated under reduced pressure, and the residue was concentrated to dryness to thereby obtain 820 mg of pale dark brown amorphous solid 5-fluoro-8-(3-hydroxypropoxy)-3-(4-methoxyphenyl)-1H-quinolin-4-one (yield: 53%).
¹H-NMR (DMSO-d₆) δppm:
1.92-2.02 (2H, m), 3.65 (2H, t, J=5.9 Hz), 4.20 (2H, t, J=6.2 Hz), 4.59 (1H, brs), 6.84-6.95 (3H, m), 7.14 (1H, dd, J=3.9 Hz, J=8.8 Hz), 7.55 (2H, d, J=8.7 Hz), 7.80 (1H, s), 11.27 (1H, brs)

The compound of the following Example 102 was prepared in the same manner as the above Example 101, using corresponding starting materials.

EXAMPLE 102

5-Fluoro-8-(2-hydroxypropoxy)-3-(4-methoxyphenyl)-1H-quinolin-4-one

White powder (ethyl acetate)
Melting point 216-218° C.
¹H-NMR (DMSO-d₆) δppm:
1.19 (3H, d, J=6.2 Hz), 3.76 (3H, s), 3.82-4.12 (3H, m), 5.25 (1H, brs), 6.84-6.96 (3H, m), 7.12 (1H, dd, J=3.9 Hz, J=8.8 Hz), 7.56 (2H, d, J=8.8 Hz), 7.86 (1H, s), 11.20 (1H, brs)

The compounds of the following Examples 103 and 104 were prepared in the same manner as the above Example 1, using corresponding starting materials.

EXAMPLE 103

5-Chloro-3-(4-methoxyphenyl)-8-propoxy-1H-quinolin-4-one

Pale brown powder (ethyl acetate)
Melting point 194-196° C.
¹H-NMR (DMSO-d₆) δppm:
1.03 (3H, t, J=7.3 Hz), 1.80-1.87 (2H, m), 3.76 (3H, s), 4.11 (2H, t, J=6.4 Hz), 6.93 (2H, d, J=8.6 Hz), 7.12 (1H, d, J=8.5 Hz), 7.17 (1H, d, J=8.5 Hz), 7.54 (2H, d, J=8.6 Hz), 7.80 (1H, s), 11.23 (1H, brs)

EXAMPLE 104

5-Bromo-8-cyclopentyloxy-3-(4-methoxyphenyl)-1H-quinolin-4-one

Pale brown powder (ethanol)
Melting point 213-215° C.
¹H-NMR (DMSO-d₆) δppm:
1.59-1.70 (2H, m), 1.71-2.00 (6H, m), 3.75 (3H, s), 4.97-5.00 (1H, m), 6.94 (2H, d, J=8.7 Hz), 7.04 (1H, d, J=8.5 Hz), 7.40 (1H, d, J=8.4 Hz), 7.53 (2H, d, J=8.7 Hz), 7.81 (1H, s), 11.20 (1H, brs)
Pharmacological Test 1
Evaluation of Improvement of Mitochondrial Dysfunction Using Human Neuroblastoma Cell Lines SH-SY5Y Treated with 1-methyl-4-phenylpyridinium (MPP⁺)

In human neuroblastoma cell lines SH-SY5Y in which mitochondrial activity was injured by MPP⁺ treatment (Bolimuntha S. et al., J Biol Chem, 280, 2132-2140 (2005) and Shang T. et al., J Biol Chem, 280, 34644-34653 (2005)), improvement of the mitochondrial dysfunction was evaluated on the basis of the measurement value of the mitochondrial oxidation reduction activity using Alamar Blue fluorescent dye after the compound addition (Nakai M. et al, Exp Neurol, 179, 103-110 (2003)).

The human neuroblastoma cell lines SH-SY5Y were cultured in Dulbecco's Modified Eagle's Medium containing 10% fetal bovine serum (DMEM containing 50 units/ml penicillin and 50 μg/ml streptomycin as antibiotics) at 37° C. in the presence of 5% carbon dioxide. Cells were scattered on a poly-D-lysine-coated 96-well black plate at a concentration of 3–6×10⁴ cells/cm² (medium amount: 100 μl/well), and cultured in the above medium for two days. Further, the medium was changed to a DMEM containing a 1% N2 supplement (N2-DMEM) or to a medium (100 μl/well) in which 1.5 mM MPP⁺ was dissolved. The cells were cultured therein for 39 to 48 hours, and then subjected to a mitochondrial oxidation reduction activity measurement system. A sample compound that had been previously dissolved in dimethyl sulfoxide (DMSO) was diluted with N2-DMEM, and added in a volume of 10 μl/well 24 hours before the activity measurement (final compound concentration: 0.01 to 1 μg/ml).

After removal of the medium by suction, a balanced salt solution containing 10% Alamar Blue (154 mM sodium chloride, 5.6 mM potassium chloride, 2.3 mM calcium chloride, 1.0 mM magnesium chloride, 3.6 mM sodium bicarbonate, 5 mM glucose, 5 mM HEPES, pH 7.2) was added in a volume of 100 ill/well, and reacted in an incubator at 37° C. for 1 hour. The fluorescent intensity was detected using a fluorescence detector (a product of Hamamatsu Photonics K.K., excitation wavelength 530 nm, measurement wavelength 580 nm) to thereby measure the mitochondrial oxidation reduction activity.

The fluorescent intensity of the well of the cells cultured in a medium containing MPP$^+$ and in each of the sample compounds was relatively evaluated based on a 100% fluorescent intensity of the well of the cells cultured in a medium containing DMSO alone (final concentration: 0.1%). When the MPP$^+$-induced cell groups exhibited higher florescent intensity than the cell groups cultured in DMSO alone, the test compound was judged to have the improved activity of the mitochondrial dysfunction.

TABLE 1

Evaluation of improvement of mitochondrial dyfunction using human neuroblastoma cell lines SH-SY5Y treated with 1-methyl-4-phenylpyridinium (MPP$^+$)

| Test Compound Concentration | Fluorescence Intensity (%) | | | | | |
|---|---|---|---|---|---|---|
| (μg/ml) | 0 | 0.01 | 0.03 | 0.1 | 0.3 | 1 |
| Compound of Example 1 | 50 | 51 | 62 | 70 | 66 | 64 |
| Compound of Example 3 | 51 | 54 | 63 | 70 | 78 | 74 |
| Compound of Example 4 | 47 | 56 | 61 | 70 | 72 | 59 |
| Compound of Example 6 | 53 | 59 | 71 | 85 | 88 | 83 |
| Compound of Example 21 | 46 | 52 | 59 | 63 | 74 | 57 |
| Compound of Example 24 | 54 | 60 | 70 | 82 | 78 | 84 |
| Compound of Example 25 | 41 | 46 | 56 | 66 | 50 | 24 |
| Compound of Example 30 | 46 | 50 | 54 | 69 | 64 | 56 |
| Compound of Example 31 | 38 | 45 | 45 | 57 | 59 | 48 |
| Compound of Example 34 | 60 | 69 | 74 | 77 | 78 | 87 |
| Compound of Example 35 | 63 | 75 | 88 | 99 | 95 | 65 |
| Compound of Example 36 | 59 | 63 | 65 | 74 | 71 | 91 |
| Compound of Example 37 | 57 | 64 | 73 | 78 | 70 | 61 |
| Compound of Example 38 | 54 | 66 | 67 | 86 | 81 | 78 |
| Compound of Example 40 | 53 | 60 | 64 | 76 | 70 | 72 |
| Compound of Example 47 | 49 | 51 | 58 | 71 | 73 | 82 |
| Compound of Example 53 | 48 | 53 | 56 | 67 | 60 | 67 |
| Compound of Example 59 | 50 | 53 | 56 | 67 | 66 | 54 |
| Compound of Example 61 | 61 | 70 | 65 | 85 | 80 | 86 |

TABLE 1-continued

Evaluation of improvement of mitochondrial dyfunction using human neuroblastoma cell lines SH-SY5Y treated with 1-methyl-4-phenylpyridinium (MPP$^+$)

| Test Compound Concentration | Fluorescence Intensity (%) | | | | | |
|---|---|---|---|---|---|---|
| (μg/ml) | 0 | 0.01 | 0.03 | 0.1 | 0.3 | 1 |
| Compound of Example 62 | 55 | 66 | 62 | 79 | 84 | 80 |
| Compound of Example 63 | 56 | 58 | 65 | 74 | 75 | 85 |
| Compound of Example 64 | 56 | 55 | 65 | 74 | 72 | 77 |
| Compound of Example 66 | 57 | 66 | 72 | 83 | 77 | 60 |
| Compound of Example 70 | 53 | 56 | 57 | 67 | 71 | 63 |
| Compound of Example 71 | 50 | 56 | 61 | 73 | 78 | 72 |
| Compound of Example 86 | 46 | 52 | 59 | 68 | 61 | 39 |
| Compound of Example 87 | 58 | 63 | 66 | 79 | 63 | 51 |
| Compound of Example 91 | 55 | 65 | 69 | 81 | 82 | 83 |
| Compound of Example 92 | 55 | 63 | 75 | 77 | 69 | 55 |
| Compound of Example 93 | 58 | 66 | 79 | 86 | 80 | 69 |
| Compound of Example 94 | 51 | 56 | 67 | 69 | 59 | 41 |
| Compound of Example 100 | 53 | 56 | 56 | 71 | 73 | 84 |

Pharmacological Test 2

Evaluation of Dopaminergic Neuronal Protective Activity Using C57BL/6 Mouse Treated with 1-methyl-4-phenyl 1,2,3,6-tetrahydro pyridine (MPTP)

Using a mouse having MPTP-injured dopaminergic neurons (Chan P. et al., J Neurochem, 57, 348-351 (1991)), the dopamine neuroprotective activity was evaluated based on dopamine contents and protein levels of tyrosine hydroxylase (TH) and dopamine transporter (DAT) (i.e., dopaminergic neuronal marker proteins) in the brain corpus striatum region after the compound administration (Mori A. et al., Neurosci Res, 51, 265-274 (2005)).

A male C57BL/6 mouse (provided by Japan Charles River Inc., 10 to 12 weeks) was used as a test animal. MPTP was dissolved in a physiological salt solution so that the concentration became 4 mg/ml, and then administered to the mouse subcutaneously in a volume of 10 ml/kg. The test compound was suspended in a 5% gum arabic/physiological salt solution (w/v) so that a compound having a concentration of 1 mg/ml could be obtained. Each of the test compounds or solvents thereof was orally administered to the mouse after 30 minutes, 24 hours, and 48 hours of the MPTP administration. The mouse was decapitated after 72 hours of the MPTP administration, the brain was removed, and each side of the striatum was dissected.

The left striatum was used as a sample to detect the protein level by Western blot analysis. Each tissue was homogenized in a HEPES buffer sucrose solution (0.32 M sucrose, 4 μg/ml pepstatin, 5 μg/ml aprotinin, 20 μg/ml trypsin inhibitor, 4 μg/ml leupeptin, 0.2 mM phenylmethanesulfonyl fluoride, 2 mM ethylenediaminetetraacetic acid (EDTA), 2 mM ethylene glycol bis (β aminoethyl ether) tetraacetic acid, 20 mM HEPES, pH 7.2), and assayed for protein using a bicinchoninic acid kit for protein assay (provided by Pierce Corporation). Each homogenized sample, having an equal amount of protein which had been dissolved in a Laemmli sample buffer solution, was subjected to electrophoresis through sodium dodecyl sulfurate polyacrylamide gels. The protein separated by electrophoresis was electrically transferred to polyvinylidene fluoride membranes. The membranes were reacted with specific primary antibody for TH, DAT, and housekeeping proteins, i.e., the α1 subunit of $Na^+/K^+$-ATPase and actin ($Na^+/K^+$-ATPase, a product of UpState Biotechnology Inc.; others are products of Chemi-Con Corporation). Subsequently, a horseradish peroxidase-labeled secondary antibody (a product of Amersham K.K.) for each primary antibody was fixed, and the chemiluminescence associated with enzyme activity of peroxidase was detected using X-ray film. The density of the protein band on the film was analyzed using a densitometer (a product of Bio-rad Laboratories Inc.) to obtain the TH value relative to $Na^+/K^+$-ATPase and the DAT value relative to actin.

The right striatum, the tissue weight of which was measured immediately after dissection, was used as an analysis sample for determining the dopamine content. Each tissue was homogenized in a 0.1 N perchloric acid solution containing isoproterenol as an internal standard substance of the measurement, using an ultrasonic homogenizer while being cooled with ice. The supernatant obtained from 20,000 g of homogenate that had been centrifuged at 4° C. for 15 minutes was subjected to a high performance liquid chromatography with a reversed phase column (a product of Eicom Corporation). A mobile phase 15% methanol 0.1 M citric acid/0.1 M sodium acetate buffer solution (containing 190 mg/l 1-sodium octane sulfonate, 5 mg/l EDTA, pH 3.5) was flowed at a rate of 0.5 ml/min, and the dopamine peak of each sample was detected using an electrochemical detector (applied voltage +750 mV vs. Ag/AgCl, a product of Eicom Corporation). With reference to the identified dopamine peak, the dopamine content per tissue weight was calculated in each sample using analysis software (a product of Gilson Inc.).

In both analyses, the value of the sample derived from the MPTP-induced mice in which only the test compound or the solvent was administered was expressed relative to the value of the sample derived from the mice without MPTP treatment (100%). Values were analyzed statistically using a nonclinical statistical analysis system. Values of significance probability <0.05 were defined as statistically significant. In the MPTP-induced mice, when the test drug group showed an increase in protein level compared to the solvent group, and a significant difference was observed between these groups at t-assay, the test drug was judged to have dopamine neuroprotective activity.

The invention claimed is:
1. A method for treating Parkinson's disease, comprising administering a quinolone compound of General Formula (1) or a salt thereof to a human or an animal:

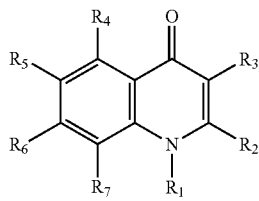

(1)

wherein $R_1$ represents a hydrogen atom, a lower alkyl group, a cyclo $C_{3-8}$ alkyl lower alkyl group, or a lower alkoxy lower alkyl group;

$R_2$ represents a hydrogen atom, a lower alkyl group, or a halogen-substituted lower alkyl group;

$R_3$ represents a phenyl group, a furyl group, a thienyl group, or a pyridyl group, each of the groups optionally being substituted with one or more groups selected from the group consisting of the following (1) to (16) on the aromatic or heterocyclic ring represented by the above $R_3$:
(1) lower alkyl groups,
(2) lower alkoxy groups,
(3) halogen-substituted lower alkoxy groups,
(4) a phenoxy group,
(5) lower alkylthio groups,
(6) a hydroxy group,
(7) hydroxy lower alkyl groups,
(8) halogen atoms,
(9) lower alkanoyl groups,
(10) lower alkoxycarbonyl groups,
(11) amino groups optionally substituted with one or more lower alkyl groups,
(12) carbamoyl groups optionally substituted with one or more lower alkyl groups,
(13) cyclo $C_{3-8}$ alkyl lower alkoxy groups,
(14) pyrrolidinyl carbonyl groups,
(15) morpholinyl carbonyl groups, and
(16) a carboxyl group;
$R_4$ represents a halogen atom;
$R_5$ represents a hydrogen atom or a halogen atom;
$R_6$ represents a hydrogen atom; and
$R_7$ represents any one of groups (1) to (15) below;
(1) a hydroxy group,
(2) a halogen atom,
(3) a lower alkoxy group,
(4) a halogen-substituted lower alkoxy group,
(5) a hydroxy lower alkoxy group,
(6) a lower alkoxy lower alkoxy group,
(7) an amino group optionally substituted with one or more members selected from the group consisting of lower alkyl groups, lower alkoxy lower alkyl groups, and cyclo $C_{3-8}$ alkyl groups,
(8) an amino lower alkoxy group optionally substituted on the amino group with one or more members selected from the group consisting of lower alkyl groups, lower alkanoyl groups, lower alkyl sulfonyl groups, and carbamoyl groups optionally substituted with one or more lower alkyl groups,
(9) a cyclo $C_{3-8}$ alkyloxy group,
(10) a cyclo $C_{3-8}$ alkyl lower alkoxy group,
(11) a tetrahydrofuryl lower alkoxy group,
(12) a lower alkylthio group,
(13) a heterocyclic group selected from the group consisting of morpholinyl groups, pyrrolidinyl groups, furyl groups, thienyl groups, and benzothienyl groups,
(14) a phenyl lower alkoxy lower alkoxy group, and
(15) a pyrrolidinyl carbonyl group.

2. The method for treating Parkinson's disease according to claim 1,
wherein $R_1$ represents a hydrogen atom or a lower alkyl group;
$R_2$ represents a hydrogen atom or a lower alkyl group;
$R_3$ represents a phenyl group or a pyridyl group, each of the groups optionally being substituted with one or two groups selected from the group consisting of the following (1), (2), (6), and (8) on the aromatic or heterocyclic ring represented by the above $R_3$:
(1) lower alkyl groups,
(2) lower alkoxy groups, (6) a hydroxy group, and
(8) halogen atoms;
R₄ represents a halogen atom;
R₅ represents a hydrogen atom;
R₆ represents a hydrogen atom; and
R₇ represents any one of groups (3), (4), and (7) below:
(3) a lower alkoxy group,
(4) a halogen-substituted lower alkoxy group, and
(7) an amino group optionally substituted with one or two lower alkyl groups.

3. The method for treating Parkinson's disease according to claim 1 selected from the group consisting of:
- 5-fluoro-3-(4-methoxyphenyl)-2-methyl-8-propoxy-1H-quinolin-4-one,
- 5-fluoro-3-(4-methoxyphenyl)-1-methyl-8-propoxy-1H-quinolin-4-one,
- 3-(2,4-dimethoxyphenyl)-5-fluoro-8-propoxy-1H-quinolin-4-one,
- 5-fluoro-8-isopropoxy-3-(4-methoxyphenyl)-1H-quinolin-4-one,
- 3-(2,4-dichlorophenyl)-5-fluoro-8-propoxy-1H-quinolin-4-one,
- 8-ethoxy-5-fluoro-3-(4-methoxyphenyl)-1H-quinolin-4-one,
- 5-fluoro-3-(4-methoxy-2-methylphenyl)-8-propoxy-1H-quinolin-4-one,
- 5-fluoro-3-(4-methoxyphenyl)-8-propoxy-1H-quinolin-4-one,
- 5-fluoro-3-(2-fluoro-4-methoxyphenyl)-8-propoxy-1H-quinolin-4-one,
- 5-fluoro-3-(4-hydroxyphenyl)-8-propoxy-1H-quinolin-4-one,
- 8-cyclopropylmethoxy-5-fluoro-3-(4-methoxyphenyl)-1H-quinolin-4-one,
- 5-fluoro-8-propoxy-3-pyridin-4-yl-1H-quinolin-4-one,
- 5-fluoro-3-(4-methoxyphenyl)-8-(N-methyl-N-propylamino)-1H-quinolin-4-one, and
- 5-fluoro-3-(4-methoxyphenyl)-8-(4,4,4-trifluorobutoxy)-1H-quinolin-4-one.

\* \* \* \* \*